(12) United States Patent
Remuzzi

(10) Patent No.: US 6,576,652 B2
(45) Date of Patent: Jun. 10, 2003

(54) USE OF AN ANGIOTENSIN II RECEPTOR ANTAGONIST FOR THE PREPARATION OF DRUGS TO INCREASE THE SURVIVAL RATE OF RENAL TRANSPLANT PATIENTS

(75) Inventor: Giuseppe Remuzzi, Bergamo (IT)

(73) Assignee: Merck Sharp & Dohme (Italia) S.p.A., Rome (IT)

( * ) Notice: Subject to any disclaimer, the term of this patent is extended or adjusted under 35 U.S.C. 154(b) by 0 days.

(21) Appl. No.: 10/076,396

(22) Filed: Feb. 19, 2002

(65) Prior Publication Data

US 2002/0115702 A1 Aug. 22, 2002

Related U.S. Application Data

(63) Continuation of application No. 09/509,791, filed on Mar. 30, 2000, now abandoned.

(30) Foreign Application Priority Data

Sep. 30, 1997 (IT) ....................................... RM97A0586

(51) Int. Cl.⁷ ........................................... A61K 31/415
(52) U.S. Cl. ...................................................... 514/396
(58) Field of Search ........................................ 514/396

(56) References Cited

U.S. PATENT DOCUMENTS

| | | | |
|---|---|---|---|
| 3,772,315 | A | 11/1973 | Regel et al. |
| 4,207,324 | A | 6/1980 | Matsumura et al. |
| 4,226,878 | A | 10/1980 | Iizuka et al. |
| 4,340,598 | A | 7/1982 | Furukawa et al. |
| 4,355,040 | A | 10/1982 | Furukawa et al. |
| 4,379,927 | A | 4/1983 | Vorbrüggen et al. |
| 4,448,781 | A | 5/1984 | Cross et al. |
| 5,130,439 | A | 7/1992 | Lo et al. |
| 5,138,069 | A | 8/1992 | Carini et al. |
| 5,219,856 | A | 6/1993 | Olsen |
| 5,492,904 | A | 2/1996 | Wong |

FOREIGN PATENT DOCUMENTS

| | | |
|---|---|---|
| EP | 0 103 647 | 3/1984 |
| EP | 0 125 033 | 11/1984 |
| EP | 0 146 228 | 6/1985 |
| EP | 0 401 030 | 12/1990 |
| EP | 0 505 098 | 9/1992 |
| WO | WO 93/10106 | 5/1993 |
| WO | WO 94/03435 | 2/1994 |
| WO | WO 94/28896 | 12/1994 |
| WO | WO 97/13513 | 4/1997 |
| WO | WO 97/21436 | 6/1997 |

OTHER PUBLICATIONS

Blasingham et al., "Differential renal effects of cyclooxygenase inhibition in sodium–replete and sodium–deprived dog", *J. Physiol*, (1980), vol. 239, pp. F360–F365.

Collins et al., "Blood pressure, Strokes, and Coronary Heart Disease", *The Lancet*, (1990), vol. 335, pp. 827–838.

Dunn, M. J., "Clinical Effects of Prostaglandins in Renal Disease", *Hospital Practice*, p. 19–99, Mar. 1984.

Ferrannini et al., "Insulin Resistance in Essential Hypertension", *The New England Journal of Medicine*, (1987), vol. 317, pp. 350–357.

Fuller et al., "p–Iodoamphetamine as a Serotonin Depletor in Rats", *The Journal of Pharmacology and Experimental Therapeutics*, (1980), vol. 212, No. 1, pp. 115–119, USA.

Julius et al., "The hemodynamic link between insulin resistance and hypertension", *Journal of Hypertension*, (1991), vol. 9, No. 11, pp. 983–986.

Keeton et al, "The Pharmacologic Alteration of Renin Release"; *Pharmacological Reviews*; , (1981), pp. 81–227; vol. 31, No. 2.

Landsberg, "Diet, Obesity and Hypertension: An Hypothesis Involving Insulin, the Sympathetic Nervous System, and Adaptive Thermogenesis", *Quarterly Journal of Medicine, New Series*, (1986), vol. 61, No. 236, pp. 1081–1090.

Modan et al., "Hyperinsulineamia: A Link Between Hypertension Obesity and Glucose Intolerance", *J. Clin. Invest.*, (1985), vol. 75, pp. 809–817.

Pals et al., "Role of the Pressor Action of Angiotensin II in Experimental Hypertension", *Circulation Research*, Dec. 1971, pp. 673–681; vol. 29.

Satoh et al., "Influence of the Renin–Angiotensin System on the Effect of Prostaglandin Synthesis Inhibitors in the Renal Vasculature", *Circulation Research*, (Suppl. 1):1–89, vols. 36 and 37, Jun. 1975.

Streeten, et al, "8. Angiotensin–receptor blocking drugs", *Handbook of Hypertension*, pp. 246–271, vol. 5, Clinical Pharmacology of Antihypertensive Drugs; (1984).

Torn et al., "Metabolism and Disposition of 4OChloro–1–(4–methoxy–3–methylbenzyl)–2phenylimidazole–5–acetic Acid (CV–2973,a New Hypotensive Agent with Dinretic Activity, in Rats and Dogs", *J. Takeda Rea. Lab.* (1982), vol. 41, No. ¾, pp. 180–191.

Weinberger, M. H., "Angiotensin–Converting Enzyme Inhibitors", *Medical Clinics N. America*; pp. 979–990, vol. 71, No. 5, Sep. 1987.

.Klaassen et al., "Losartan, An Angiotensin–II Receptor Antagonist, Reduces Hematocrits in Kidney Transplant Recipients with Posttransplant Erythrocytosis," Transplantation, vol. 64, No. 5, Sep. 15, 1997.

(List continued on next page.)

Primary Examiner—Kevin E. Weddington
(74) Attorney, Agent, or Firm—Browdy & Neimark PLLC

(57) ABSTRACT

The present invention relates to the use, for the preparation of drugs to increase the survival rate of transplant patients, including renal and heart transplant patients, of a therapeutically effective amount of an angiotension II receptor antagonist compound, such as the class of substituted imidazoles represented by formula (I) and in particular by losartan potassium, 2-butyl-4-chloro-[(2'-tetrazol-5-yl) biphenyl-4-il]methyl]-5-(hydroxymethyl)imidazole potassium salt.

21 Claims, No Drawings

OTHER PUBLICATIONS

Sanders et al., "Role of Hypertension in Chronic Renal Allograft Dysfunction," Kidney International, vol. 48, suppl. 52 (1995), pp. s–43–s–47.

Benediktsson et al., "Antihypertensive Drug Treatment in Chronic Renal Allograft Rejection in the Rat," Transplantation, vol. 62, No. 11, Dec. 15, 1996, 1634–1642.

Amuchastegui et al., "Chronic Allograft Nephropathy in the Rat is Improved by Angiotension II Receptor Blockade but not by Calcium Channel Antagonism," Jour. Amer. Soc. of Nephrology, vol. 9, pp. 1998, 1948–1955.

Navarro et al., "Control of Severe Proteinuria with Losartan After Renal Transplantation," Am. Jour. of Nephrology, 18:261–262, 1998.

Ducloux et al., "Treatment of Posttransplant Erythrocytosis with Losartan," Transplantation Proceedings, 29, 2407–2408 (1997).

Ziai et al, "Renal Protective Effects of Losartan in F344–LEW Rats," Jour. Amer. Soc. Of Nephrology, vol. 8, pp. 670A Sep. 1997.

Glicklich et al, "Efficacy of Losartan (L) Therapy for Hypertension (HTN) in Renal Transplant (RT) Patients," Jour. Amer. Soc. of Nephrology, vol. 7, No. 9, pp. 1909.

Abstract of Glicklich et al, "Efficacy of Losartan (L) Therapy for Hypertension (HTN) in Renal Transplant (RT) Patients," Jour. Amer. Soc. of Nephrology, vol. 7, No. 9, pp. 1909.

Wong, et al., "Mechanism Of Captopril–Induced Renal Vasodilatationin Anesthetized Dogs After Nonhypotensive Hemorrhage," Journal of Pharmacology and Experimental Therapeutics, vol. 215, No. 1 (1980):104–109.

USE OF AN ANGIOTENSIN II RECEPTOR ANTAGONIST FOR THE PREPARATION OF DRUGS TO INCREASE THE SURVIVAL RATE OF RENAL TRANSPLANT PATIENTS

This is a continuation of application Ser. No. 09/509,791, filed Mar. 30, 2000, now abandoned.

FIELD OF THE INVENTION

This invention relates to the use of an angiotensin II receptor antagonist, such as substituted imidazole compounds, for the treatment of Post-transplant hypertension. The invention also relates to use of an angiotensin II receptor antagonist, such as substituted imidazole compounds, for the preparation of drugs to increase the survival rate of transplant patients, including renal transplant patients. The invention also relates to a method of using an angiotensin II receptor antagonist, such as substituted for increasing the survival rate of transplant patients, including renal transplant patients.

Substituted imidazoles of formula I are known to inhibit the action of the octapeptide hormone angiotensin II (AII) and are useful therefore in alleviating angiotensin induced hypertension. The enzyme renin acts on a blood plasma α2-globulin, angiotensinogen, to produce angiotensin I, which is then converted by angiotensin converting-enzyme to AII. The latter substance is a powerful vasopressor agent which has been implicated as a causitive agent, for producing high blood pressure in various mammalian species, such as the rat, dog, and man. The compounds disclosed in this application inhibit the action of AII at its receptors on target cells and thus prevent the increase in blood pressure produced by this hormone-receptor interaction. The present application discloses a method for the improvement of insulin sensitivity by administering an angiotensin II receptor antagonist, such as a substituted imidazole of formula I, to a species of mammal with hypertension due to angiotensin II. Administration of an angiotensin II receptor antagonist, such as a substituted imidazole of formula I, with a diuretic, such as furosemide or hydrochlorothiazide; either as a stepwise combined therapy (diuretic first) or as a physical mixture, enhances the antihypertensive effect of the compound, while also improving the insulin sensitivity of the patient.

K. Matsumura, et al., in U.S. Pat. No. 4,207,324 issued Jun. 10, 1980, discloses 1,2-disubstituted-4-haloimidazole-5-acetic acid derivatives of the formula:

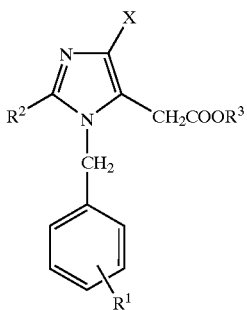

wherein R1 is hydrogen, nitro or amino; R2 is phenyl, furyl or thienyl optionally substituted by halogen, lower alkyl, lower alkoxy or di-lower alkylamino; R3 is hydrogen or lower alkyl and X is halogen; and their physiologically acceptable salts. These compounds have diuretic and hypotensive actions.

Furukawa, et al., in U.S. Pat. No. 4,355,040 issued Oct. 19, 1982, discloses hypotensive imidazole-5-acetic acid derivatives having the formula:

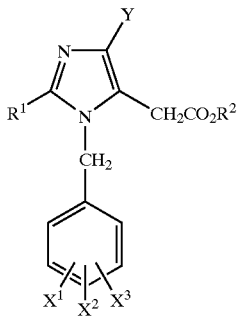

wherein R1 is lower alkyl, cycloalkyl, or phenyl optionally substituted; X1, X2, and X3 are each hydrogen, halogen, nitro, amino, lower alkyl, lower alkoxy, benzyloxy, or hydroxy, Y is halogen and R2 is hydrogen or lower alkyl; and salts thereof.

Furukawa, et al., in U.S. Pat. No. 4,340,598, issued Jul. 20, 1982, discloses hypotensive imidazole derivatives of the formula:

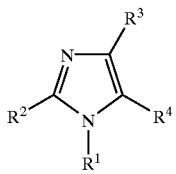

wherein R1 is lower alkyl or, phenyl C1–2 alkyl optionally substituted with halogen or nitro; R2 is lower alkyl, cycloalkyl or phenyl optionally substituted; one of R3 and R4 is —(CH2)nCOR5 where R5 is amino, lower
  alkoxyl or hydroxyl and n is 0, 1, 2 and the other of R3 and R4 is hydrogen or halogen; provided that RI is lower alkyl or phenethyl when R3 is hydrogen, n=1 and R5 is lower alkoxyl or hydroxyl; and salts thereof.

Furukawa, et al., in EP 103,647 discloses 4-chloro-2-phenylimidazole-5-acetic acid derivatives useful for treating edema and hypertension of the formula:

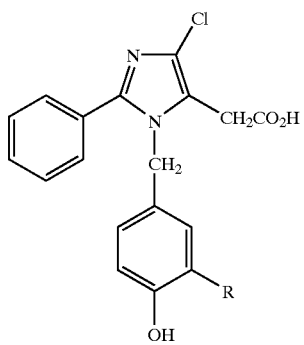

where R represents lower alkyl and salts thereof.

The metabolism and disposition of hypotensive agent 4-chloro-1-(4-methoxy-3-methylbenzyl)-2-phenyl-imidazole-5-acetic acid is disclosed by H. Torfii in Takeda Kenkyushoho, 41, No 3/4,180–191 (1982).

Frazee, et al., in EP 125,033-A discloses 1-phenyl(alkyl)-2-(alkyl)-thioimidazole derivatives which are inhibitors of dopamine-β-hydroxylase and are useful as antihypertensives, diuretics and cardiotonics.

Published European Patent Application EP 146,228-A filed Oct. 16, 1984, by S. S. L. Parhi discloses a process for the preparation of 1-substituted-5-hydroxymethyl-2-mercaptoimidazoles.

A number of references disclose 1-benzyl-imidazoles such as U.S. Pat. No. 4,448,781 to Cross and Dickinson (issued May 15, 1984); U.S. Pat. No. 4,226,878 to Ilzuka, et al. (issued Oct. 7, 1980); U.S. Pat. No. 3,772,315 to Regel, et al. (issued Nov. 13, 1973); U.S. Pat. No. 4,379,927 to Vorbruggen, et al. (issued Apr. 12, 1983); amongst others.

Pals, et al., Circulation Research 29,673 (1971) describe the introduction of a sarcosine residue in position 1 and alanine in position 8 of the endogenous vasoconstrictor hormone AII to yield an (octa)peptide that blocks the effects of AII on the blood pressure of pithed rats. This analog, [Sar1, Ala8] AII, initially called "P-113" and subsequently "Saralasin," was found to be one of the most potent competitive antagonists of the actions of AII, although, like most of the so-called peptide-AII-antagonists, it also possesses agonistic actions of its own. Saralasin has been demonstrated to lower arterial pressure in mammals and man when the (elevated) pressure is dependent on circulating AII (Pals et al., Circulation Research 29,673 (1971); Streeten and Anderson, Handbook of Hypertension, Vol. 5, Clinical Pharmacology of Antihypertensive Drugs, A. E. Doyle (Editor), Elsevier Science Publishers B. V., p. 246 (1984). However, due to its agonistic character, Saralasin generally elicits, pressor effects when the pressure is not sustained by AII. Being a peptide, the pharmacological effects of saralasin are relatively short-lasting and are only manifest after parenteral administration, oral doses being ineffective. Although the therapeutic uses of peptide AII-blockers like saralasin, are severely limited due to their oral ineffectiveness and short duration of action, their major utility is as a pharmaceutical standard.

Currently there are several A II antagonists in development. Among these development candidates, is Losartan which is disclosed in a U.S. Pat. No. 5,138,069 issued to DuPont on Aug. 11, 1992. Losartan has been demonstrated to be an orally active A II antagonist, selective for the-AT1 receptor subtype.

Some known non-peptide antihypertensive agents act by inhibiting an enzyme, called angiotensin converting enzyme (ACE), which is responsible for conversion of angiotensin I to AII. Such agents are thus referred to as ACE inhibitors, or converting enzyme inhibitors (CEI's). Captopril and enalapril are commercially available CEI's.

Based on experimental and clinical evidence, about 40% of hypertensive patients are non-responsive to treatment with CEI's. But when a diuretic such as furosemide or hydrochlorothiazide is given together with a CEI, the blood pressure of the majority of hypertensive patients is effectively normalized Diuretic treatment converts the non-renin dependent state in regulating blood pressure to a renin-dependent state. Although the imidazoles of this invention act by a different mechanism, i.e., by blocking the AII receptor rather than by inhibiting the angiotensin converting enzyme, both mechanisms involve interference with the renin-angiotensin cascade. A combination of the CEI enalapril mialeate and the diruetic hydrochlorothiazide is commercially available under the trademark Vaseretic® from Merck & Co. Publications which relate to the use of diuretics with CEI's to treat hypertension, in either a diuretic-first, stepwise approach or in physical combination, include Keeton, T. K. and Campbell, W. B., Pharmacol. Rev., 31:81 (1981) and Weinberger, M. H., Medical Clinics N. America, 71:979 (1987). Diuretics have also been administered in combination with saralasin to enhance the antihypertensive effect.

Non-steroidal anti-inflammatory drugs (NSAID's) have been reported to induce renal failure in patients with renal under perfusion and high plasma level of AII. (Dunn, M. J., Hospital Practice, 19–99, 1984). Administration of an AII blocking compound of this invention in combination with an NSAID (either stepwise or in physical combination) can prevent such renal failure. Saralasin has been shown to inhibit the renal vasoconstrictor effect of indomethacin and meclofenamate in dogs (Satoh, et al., Circ. Res. 36/37 (Suppl. 1): 1–89, 1975; Blasingham, et al., Am J. Physiol 239-(F360,1980). The CEI captopril has been demonstrated to reverse the renal vasoconstrictor effect of indomethacin in dogs with non-hypotensive hemorrhage. (Wong, er al., J. Pharmacol. Exp.Ther 219:104,1980).

Insulin resistance is defined as a reduced biological effect of insulin, and has been shown to be an independent risk factor for cardiovascular disease, and to be associated with hypertension, obesity and diabetes. Modan M, Halkin H, Almog S., et al.: Hyperinsulineamia: a link between hypertension, obesity and glucose intolerance. J. Clin Invest 1985, 75:809–817; Landberg L: Diet, obesity, and hypertension: an hypothesis involving insulin, the sympathetic nervous system, and adaptive thermogenesis. Q. J. Med. 1986, 236: 1081–1090; Ferranini E, Buzzigoli G, Giorico M A., et al.: Insulin resistance in essential hypertension. 9. Engl. J. Med. 1987, 317:350–357.

Pharmacological treatment of hypertension has reduced the incidence of stroke to the level expected from epidemiological studies, but has shown considerably less of an effect on coronary heart disease. Collins R., Peto R., MacMahon, S., Hebert P. Fiebach N. H., Eberlein K. A., et al. "Blood Pressure, Stroke and Coronary Heart Disease. Part 2, short term reductions in Blood pressure: overview of randomized drug trials in their epidemiological context." Lancet 1990; 9: 983–986. The reason for this is unclear, but one of the, possible explanations is the use of beta-blockers and diuretics negatively influence lipid balance and insulin sensitivity. Studies of other vasodilatatory drugs, such as calcium-channel blockers, ACE-inhibitors and alpha-blockers, these drugs have been found to be neutral or improve insulin resistance. A mechanism has been suggested by Julius S. Gudbrandsson T, Jamerson. K et al., "The hemodynamic link between insulin resistance and hypertension." J. Hypertens 1991; 9:983–986 and others, that it is possibly a hemodynamic determinator of insulin resistance.

DETAILED DESCRIPTION OF THE INVENTION

The use for the preparation of drugs for and a method of increasing the survival rate of transplant patients, including renal and heart transplant patients, of a therapeutically effective amounts of an angiotensin II receptor antagonist compound of formula I:

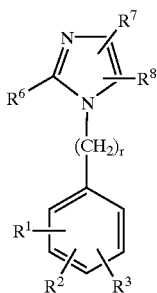

wherein:

R¹ is:

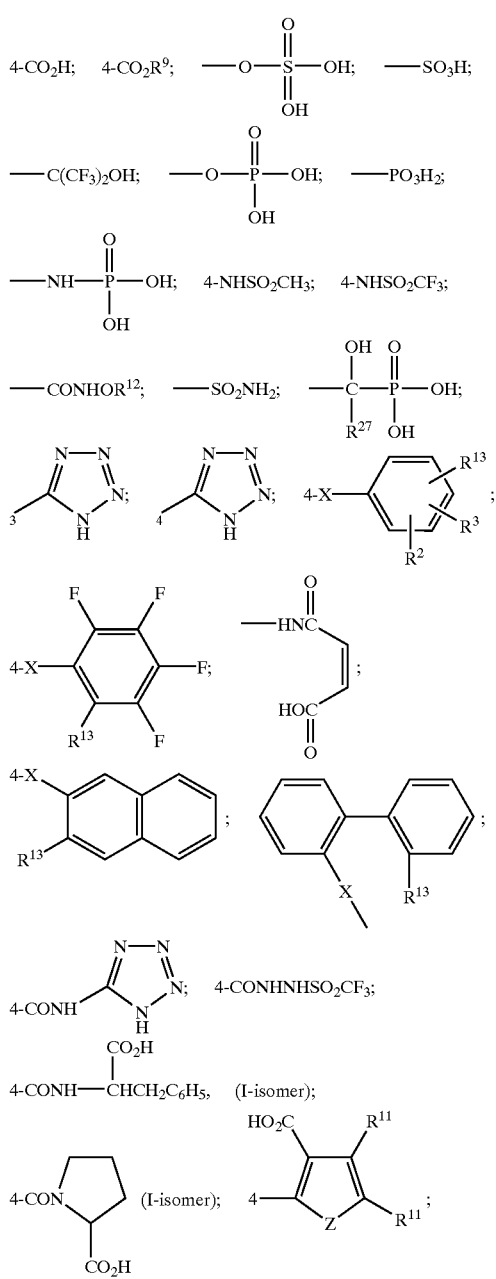

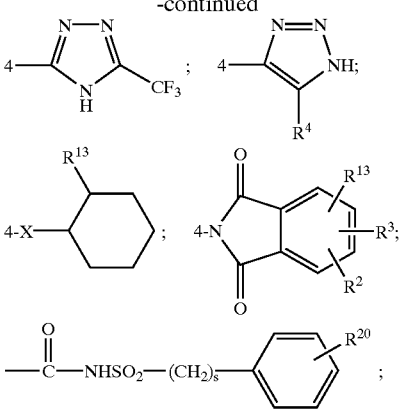

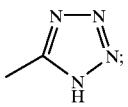

$R^2$ is H; Cl; Br; I; F; $NO_2$; CN; alkyl of 1 to 4 carbon atoms; acyloxy of 1 to 4 carbon atoms; alkoxy of 1 to 4 carbon atoms; $CO_2H$; $CO_2R^9$; $HNSO_2CH_3$; $NHSO_2CF_3$; $CONHOR^{12}$; $SO_2NH_2$;

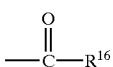

aryl; or furyl;

R3 is H; Cl, Br, I or F; alkyl of 1 to 4 carbon atoms or alkoxy of 1 to 4 carbon atoms;

R4 is CN, $NO_2$ or $CO_2R^{11}$;

R5 is H; alkyl of 1 to 6 carbon atoms, cycloalkyl of 3 to 6 carbon atoms, alkenyl or alkynyl of 2 to 4 carbon atoms;

R6 is alkyl of 2 to 10 carbon atoms, alkenyl or alkynyl of 3 to 10 carbon atoms or the same groups substituted with F or CO2RI4; cycloalkyl of 3 to 8 carbon atoms, cycloalkylalkyl, of 4 to 10 carbon atoms; cycloalkylalkenyl or cycloalkylalkynyl 5 to 10 carbon atoms; (CH2)sZ(CH2)mR5 optionally substituted with F or CO2R14; benzyl substituted on the phenyl ring with 1 or 2 halogens, alkoxy of 1 to 4 carbon atoms, alkyl of 1 to 4 carbon atoms or nitro;

R7 is H⁻; F, Cl, Br, I, NO2, CvF2v+1, where v=1–6, C6F5; CN;

$$-\overset{O}{\underset{}{C}}-R^{16}$$

straight or branched alkyl of 1 to 6 carbon atoms; phenyl or phenylalkyl, where alkyl is 1 to 3 carbon atoms; or substituted phenyl or substituted phenylalkyl, where alkyl is 1 to 3 carbon atoms, substituted with one or two substituents selected from alkyl of 1 to 4 carbon atoms, F, Cl, Br, OH, OCH3, CF3, and COOR, where R is H, alkyl of 1 to 4 carbon atoms, or phenyl;

R8 is H, CN, alkyl of 1 to 10 carbon atoms, alkenyl of 3 to 10 carbon atoms, or the same groups substituted with F; phenylalkenyl wherein the aliphatic portion is 2 to 6 carbon atoms; —(CH2)m-imidazole-1-yl; —(CH2)m-1,2,3-triazolyl optionally substituted with one or two groups selected from CO2CH3 or alkyl of 1 to 4 carbon atoms; (CH2)s tetrazolyl;

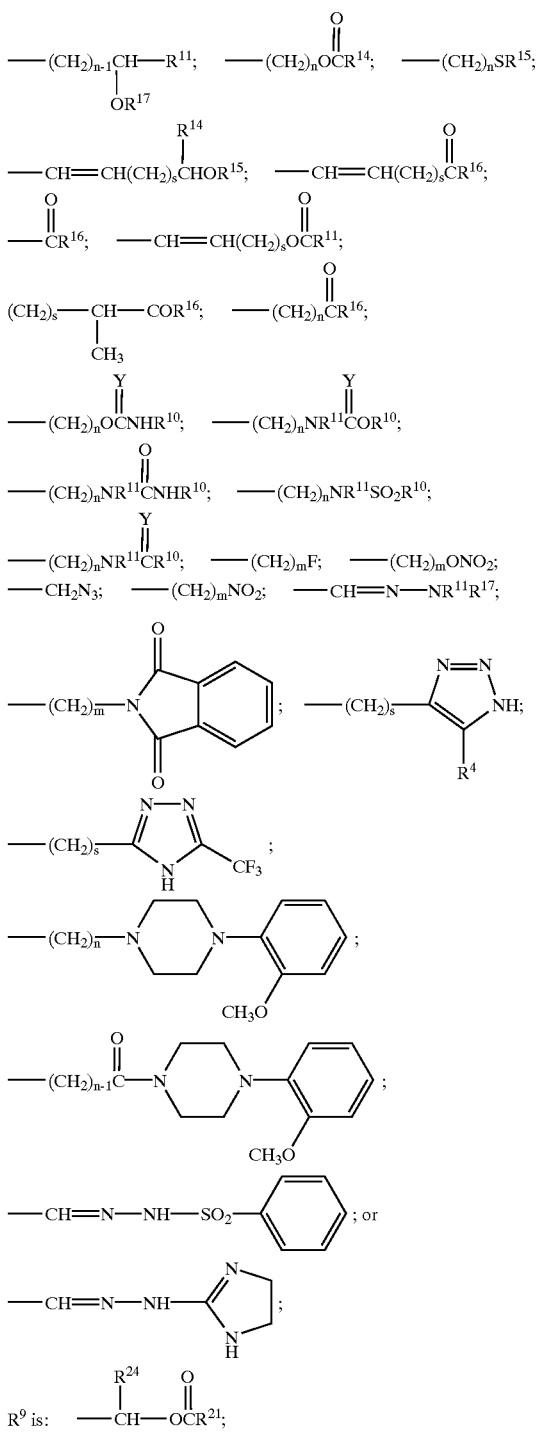

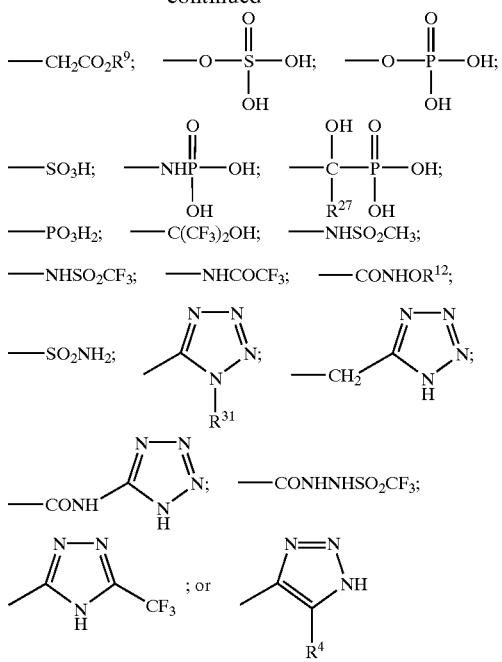

R10 is alkyl of 1 to 6 carbon atoms or perfluoroalkyl of 1 to 6 carbon atoms, 1-adamantyl, 1-naphthyl, 1-(1-naphthyl)ethyl, or (CH2)pC6H5;

R11 is H, alkyl of 1 to 6 carbon atoms, cycloalkyl of 3 to 6 carbon atoms, phenyl or benzyl;

R12 is H, methyl or benzyl;

R13 is 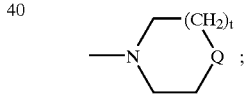

$R^{14}$ is H, alkyl or perfluoroalkyl of 1 to 8 carbon atoms, cycloalkyl of 3 to 6 carbon atoms, phenyl or benzyl;

$R^{15}$ is H, alkyl of 1 to 6 carbon atoms, cycloalkyl of 3 to 6 carbon atoms, phenyl, benzyl, acyl of 1 to 4 carbon atoms, phenacyl;

$R^{16}$ is H, alkyl of 1 to 6 carbon atoms, cycloalkyl of 3 to 6 carbon atoms, $(CH_2)pC_6H_5$, $OR^{17}$, or $NR^{18}R^{19}$;

$R^{17}$ is H, alkyl of 1 to 6 carbon atoms, cycloalkyl of 3 to 6 carbon atoms, phenyl or benzyl;

$R^{18}$ and $R^{19}$ independently are H, alkyl of 1 to 4 carbon atoms, phenyl, benzyl, α-methylbenzyl, or taken together with the nitrogen form a ring of the formula

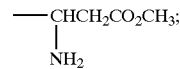

Q is $N^{20}$, O or $CH_2$;

$R^{20}$ is H, alkyl of 1–4 carbon atoms, or phenyl;

$R^{21}$ is of 1 to 6 carbon atoms, $-NR^{22}R^{23}$, or $$-\underset{\underset{NH_2}{|}}{CH}CH_2CO_2CH_3;$$

$R^{22}$ and $R^{23}$ independently are H, alkyl of 1 to 6 carbon atoms, benzyl, or are taken together as $(CH_2)u$, where u is 3–6;

$R^{24}$ is H, $CH_3$ or $-C_6H_5$;

$R^{25}$ is $NR^{27}R^{28}$, $OR^{28}$, $NHCONH_2$, $NHCSNH_2$,

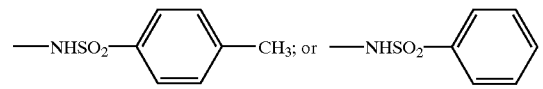

$R^{26}$ is hydrogen, alkyl with from 1 to 6 carbon atoms, benzyl, or allyl;

$R^{27}$ and $R^{28}$ are independently hydrogen, alkyl with from 1 to 5 carbon atoms, or phenyl;

$R^{29}$ and $R^{30}$ are independently alkyl of 1–4 carbon atoms or taken together are —$(CH_2)_q$—;

$R^{31}$ is H, alkyl or 1 to 4 carbon atoms, —$CH_2CH=CH_2$ or $CH_2C_6H_4R^{32}$;

X is a carbon—carbon single bond,

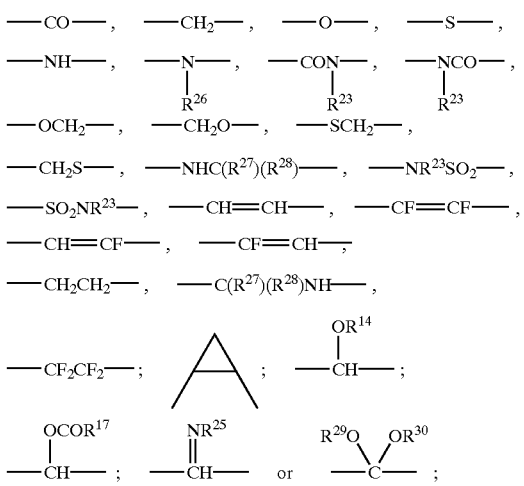

Y is O or S;
Z is O, NR11, or S;
m is 1 to 5;
n is 1 to 10;
p is 0 to 3;
q is 2 to 3;
r is 0 to 2;
s is 0 to 5;
and pharmaceutically acceptable salts of these compounds;
provided that:
(1) the $R^1$ group is not in the ortho position.
(2) when $R^1$ is

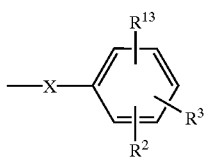

X is a single bond, and $R^{13}$ is $CO_2H$, or

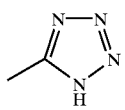

then R13 must be in the ortho or meta position; or
when R1 and X are as above and R13 is NHSO2CF3 or NHSO2CH3, R13 must be ortho;
(3) when R1 is

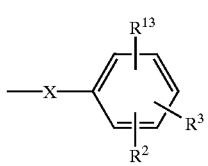

and X is other than a single bond, then R13 must be ortho except when X=$NR^{23}CO$ and $R^{13}$ is $NHSO_2CF_3$ or $NHSO_2CH_3$, then R13 must be ortho or meta;

(4) when, $R^1$ is 4-$CO_2H$ or a salt thereof, $R^6$ cannot be 8-alkyl;
(5) when $R^1$ is 4-$CO_2H$ or a salt thereof, the substituent on the 4-position of the imidazule cannot be $CH_2OH$, $CH_2OCOCH_3$, or $CH_2CO_2H$;
(6) when $R^1$ is

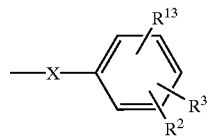

X is —$OCH_2$—, and $R^{13}$ is 2-$CO_2H$, and $R^7$ is H then $R^6$ is not $C_2H_5S$;
(7) when R1 is

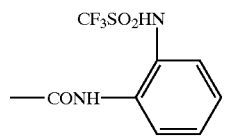

and R6 is n-hexyl then R7 and R8 are not both hydrogen;
(7) when R1 is

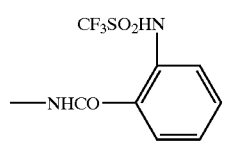

R6 is not methoxybenzyl;
(9) the R6 group is not

or $CH_2OH$;
(10) When r=0, $R^1$ is

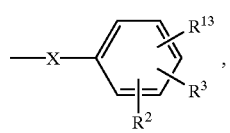

X is

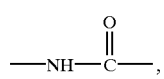

$R^{13}$ is 2-$NHSO_2CF_3$, and $R^6$ is n-propyl, then R7 and $R^8$ are not —$CO_2CH_3$;
(11) when r=0, $R^1$ is:

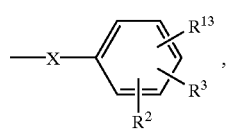

X is

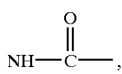

$R^{13}$ is 2-COOH, and $R^6$ is n-propyl; then $R^7$ and $R^8$ are not —CO$_2$CH$_3$;

(12) when r=1, $R^1$ is:

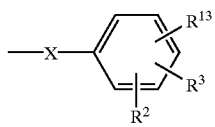

X is a single bond, $R^7$ is Cl, and $R^8$ is —CHO, then $R^{13}$ is not 3-(tetrazol-5-yl).

(13) when r=1, $R^1$ is:

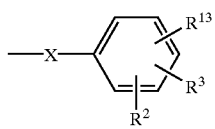

X is a single bond, $R^7$ is Cl, and $R^8$ is —CHO, then $R^{13}$ is not 4-(tetrazol-5-yl).

The following variations of the invention also form an object of the present invention.

The use for the preparation of drugs and a method for treating and preventing chronic rejection in renal transplant patients, using a therapeutically effective amount of an angiotensin II receptor antagonist compound of formula I as above.

The use for the preparation of drugs and a method for reducing proteinuria in renal transplant, using a therapeutically effective amount of an angiotensin II receptor antagonist compound of formula I as recited above.

The use for the preparation of drugs and a method for treating post-transplant hypertension in renal transplant patients, using a therapeutically effective amount of an angiotensin II receptor antagonist compound of formula I as above.

An embodiment of the invention is the use for the preparation of drugs and a method for increasing the survival rate of transplant patients, including renal and heart transplant patients, using a therapeutically effective amount of an angiotensin II receptor antagonist compound of formula II:

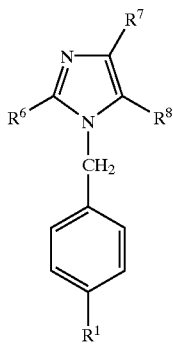

wherein:

$R^1$ is CO$_2$H; —NS$_2$CF$_3$;

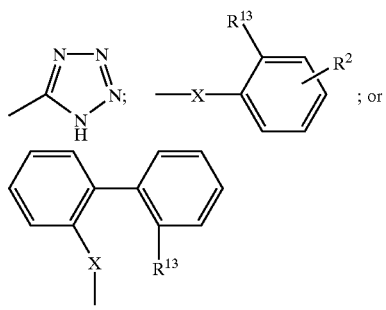

$R^6$ is alkyl of 3 to 10 carbon atoms, alkenyl of 3 to 10 carbon atoms, alkynyl of 3 to 10 carbon atoms, cycloalkyl of 3 to 8 carbon atoms, benzyl substituted on the phenyl ring with up to two groups selected from alkoxy of 1 to 4 carbon atoms, halogen, alkyl of 1 to 4 carbon atoms, and nitro;

$R^8$ is phenylalkenyl wherein the aliphatic portion is 2 to 4 carbon atoms, —(CH$_2$)$_m$-imidazol-1yl, —(CH$_2$)$_m$ 1,2,3-triazolyl optionally substituted with one or two groups selected from CO$_2$CH$_3$ or alkyl of 1 to 4 carbon atoms,

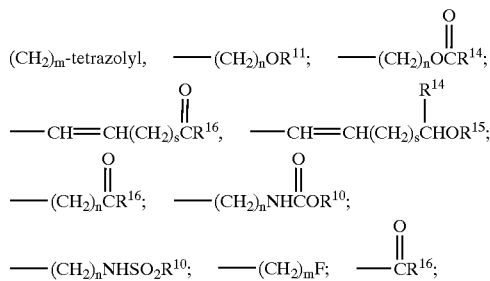

$R^{13}$ is —CO$_2$H, —CO$_2$R$^9$, NHSO2CF$_3$; SO$_3$H;

or 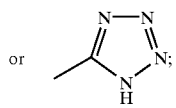

$R^{16}$ is H, alkyl of 1 to 5 carbon atoms, OR$^{17}$, or NR$^{18}$R$^{19}$;
X is carbon—carbon single bond, —CO—,

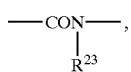

—CH$_2$CH$_2$—,

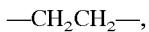

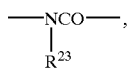

—OCH$_2$—, —CH$_2$O—, —SCH$_2$—, —CH$_2$S—, —NHCH$_2$—, —CH$_2$NH— or —CH=CH—; and pharmaceutically acceptable salts of these compounds.

An embodiment of the invention is the use for the preparation of drugs and a method for treating and preventing chronic rejection in. renal transplant patients, using a therapeutically effective amount of an angiotensin II receptor antagonist compound of formula II as recited above.

An embodiment of the invention is the use for the preparation of drugs and a method for reducing proteinuria in renal transplant, using a therapeutically effective amount of an angiotensin II receptor antagonist compound of formula II as recited above.

An embodiment of the invention is the use for the preparation of drugs and a method for treating post-transplant hypertension in renal transplant patients, using a therapeutically effective amount of an angiotensin II receptor antagonist compound of formula II as recited above.

A preferred embodiment of the invention is the use for the preparation of drugs ans a mehod for increasing the survival rate of transplant patients, including renal and heart transplant patients, using a therapeutically effective amount of an angiotensin II receptor antagonist compound of formula III:

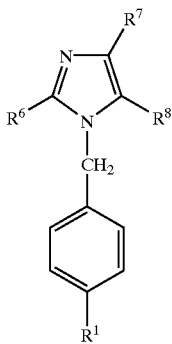

wherein:
$R^2$ is H, alkyl of 1 to 4 carbon atoms, halogen, or alkoxy of 1 to 4 carbon atoms;
$R^6$ is alkyl, alkenyl or alkynyl of 3 to 7 carbon atoms;
$R^7$ is H, Cl, Br, $C_vF_{2v+1}$, where v=1–3, or 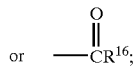

$R^8$ is —(CH$_2$)$_m$OR$^{11}$; —(CH$_2$)$_m$OCR$^{14}$;

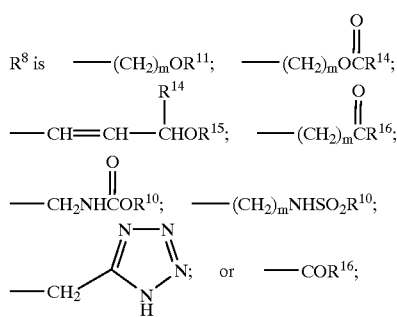

$R^{10}$ is CF$_3$, alkyl of 1 to 6 carbon atoms or phenyl;
$R^{11}$ is H, or alkyl of 1 to 4 carbon atoms;
$R^{13}$ is CO$_2$H; CO$_2$CH$_2$OCOC(CH$_3$)$_3$; NHSO$_2$CF$_3$;

and 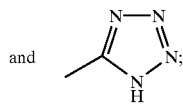

$R^{14}$ is H, or alkyl of 1 to 4 carbon atoms;

$R^{15}$ is H, alkyl of 1 to 4 carbon atoms, or acyl of 1 to 4 carbon atoms;
$R^{16}$ is H, alkyl of 1 to 5 carbon atoms; OR$^{17}$; or

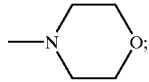

m is 1 to 5
X is single bond; —O—; —CO—; NHCO—; or —OCH$_2$—;
and pharmaceutically acceptable salts thereof.

An embodiment of the invention is the use for the preparation of drugs and a method for treating and preventing chronic rejection in renal transplant patients using a therapeutically effective amount of an angiotensin II receptor antagonist compound of formula III as recited above.

An embodiment of the invention is the use for the preparation of drugs and a method for reducing proteinuria in renal transplant using a therapeutically effective amount of an angintensin II receptor antagonist compound of formula III as recited above.

An embidoment of the invention is the use for the preparation of drugs and a method for treating post-transplant hypertension in renal transplant patients, using a therapeutically effective amount of an angiotensin II receptor antagonist compound of formula III as recited above.

A more preferred embodiment of the invention is the use for the preparation of drugs nd a method for increasing the survival rate of transplant patients, including renal and heart transplant patients, using a therapeutically effective amount of an angiotensin II receptor antagonist selected from the group consisting of:
2-Butyl-4-chloro-1-[(2'-(1H-tetrazol-Syl).yl)biphenyl-4yl) methyl]-5-(hydroxymethyl) imidazole;
2-butyl-4-chloro-1-[(2'-carboxybiphenyl-4-yl)methyl)-5-(hydroxy-methyl) imidazole
2-Butyl-4-chloro-1-[(2'-carboxybiphenyl-4-yl)methyl]-5-L (methoxy-carbonyl)aminomethyl]imidazole
2-Butyl-4-chloro-1-[(2-carboxybiphenil-4-yl)methyl]-5-[(propoxy-carbonyl)aminomethyl]imidazole
2-Butyl-4-chloro-1-[(2'-carboxybiphenyl-4-yl)methyl] imidazole-5-carboxaldehyde;
2-Butyl-1-[(2'-carboxybiphenyl-4-yl)methyl]-imidazole-5-carboxaldehyde;
2-(1E-Butenyl)-4-chloro-1-[(2'-carboxybiphenyl-4-yl) methyl]-5(hydroxymethyl)imidazole;
2-(1E-Butenyl)-4-chloro-1-[(2'-carboxybiphenyl-4-yl) methyl]-imidazole 5-carboxaldehyde;
2-Propyl-1-chloro-1-[(2'-(1H-tetrazol-5-yl)biphenyl-4-yl) methyl]-5-(hydroxymethyl) imidazole;
2-Propyl-4-chloro-1[(2'-(1H-tetrazol-5-yl)biphenyl-4-yl) methyl]-imidazole-5-carboxaldehyde;
2-Butyl-4-chloro-1-[2'-(1H-tetrazol-5-yl)biphenyl-4-yl) methyl]-imidazole-5-carboxaldehyde;
2-(1E-Butenyl)-4-chloro-1-[(2'-(1H-tetrazol-5-yl)biphenyl-4-yl)methyl]-5-hydroxymethyl) imidazole;
2-(1E-Butenyl)-4-chloro-1-[(2'-(1H-tetrazol-5-yl)biphenyl-4-yl)methyl]imidazole-5-carboxaldehyde;
2-Butyl-4-chloro-1-[(2'-(1H-tetrazol-5-yl)-biphenyl-4-yl) methyl]-imidazole-5-carboxylic acid;
2-Propyl-4-chloro-1-[(2'-(1H-tetrazol-5-yl)-biphenyl-4-yl) methyl]-imidazole-5-carboxylic acid;
2-Propyl-4-trifluoromethyl-1-[(2'-(1H-tetrazol-5-yl) biphenyl-4-yl)methyl]imidazole-5-carboxylic acid;
2-Propyl-4-trifluoromethyl-1-[(2'-(1H-tetrazol-5-yl) biphenyl-4-yl)methyl]-5-(hydroxylmethyl)imidazole;

2-Butyl-4-trifluoromethyl-1-[2'-(1H-tetrazol-5-yl)biphenyl-4-yl)methyl]imidazole-5-carboxylic acid;
2-Propyl-4-trifluoromethyl-1-[(2'-(carboxybiphenyl-4-yl)methyl]-imidazole-5-carboxaldehyde;
2-Propyl-4-pentafluoroethyl-1-[(2'-(1H-tetrazol-5-yl)biphenyl-4-yl)methyl]-5-(hydroxymethyl)imidazole;
2-Propyl-1-[(2-(1H-tetrazol-5-yl)biphenyl-4-yl)methyl]imidazole-4,5,-dicarboxylic acid;
2-Propyl-4-pentafluoroethyl-1-[(2'-(1H-tetrazol-5-yl)biphenyl-4-yl)methyl]imidazole-5-carboxylic acid;
2-Propyl-4-pentafluoroethyl-[(2'-(1H-tetrazol-5-yl)biphenyl-4-yl)methyl]imidazole-5-carboxaldehyde; and
or a pharmaceutically acceptable salt thereof.

A more preferred embodiment of the invention is the use for the preparation of drugs and a method for treating and preventing chronic rejection in renal transplant patients, using a therapeutically effective amount of an angiotensin II receptor antagonist compound to as recited above.

A more preferred embodiment of the invention is the use for the preparation of drugs and a method for reducing proteinuria in renal transplant, using a therapeutically effective amount of an angiotensin II receptor antagonist as recited above.

A more preferred embodiment of the invention is the use for the preparation of drugs and a method for treating post-transplant hypertension in renal transplant patients, using a therapeutically effective amount of an angiotensin II receptor antagonist as recited above.

A most preferred embodiment of the invention is the use for the preparation of drugs and a mehtod for increasing the survival rate of transplant patients, including renal and heart transplant patients, using a therapeutically effective amount of an angiotensin II receptor antagonist selected from the group consisting of:
2-Butyl-4-chloro-1-[(2'-tetrazol-5-yl)biphenyl-4-yl]methyl3-5-(hydroxy-methyl) imidazole; and
2-Butyl-4-chloro-1-[(2'-tetrazol-5-yl)biphenyl-4-yl]methylimidazole-5-carboxylic acid or a pharmaceutically acceptable salt thereof.

A most preferred embodiment of the invention is the use for the preparation of drugs and a method for treating and preventing chronic rejection in renal transplant patients, using a therapeutically effective amount of an angiotensin II receptor antagonist compound as recited above.

A most preferred embodiment of the invention is the use for the preparation of drugs and a method for reducing proteinuria in renal transplant, of a therapeutically effective amount of an angiotensin II receptor antagonist as recited above.

A most preferred embodiment of the invention is the use for the preparation of drugs and a method for treating post-transplant hypertension in renal transplant patients, using a therapeutically effective amount of an angiotensin II receptor antagonist as recited above.

Note that throughout the text when an alkyl substituent is mentioned, the normal alkyl structure is meant (i.e., butyl is n-butyl) unless otherwise specified.

Pharmaceutically suitable salts include both the metallic (inorganic) salts and organic salts; a list of which is given in Remington's Pharmaceutical Sciences 1–7th Edition, pg. 1418 (1985). It is well known to one skilled in the art that an appropriate salt form is chosen based on physical and chemical stability, flowability, hydro-scopicity and solubility. Preferred salts of this invention for the reasons cited above include potassium, sodium, calcium, and ammonium salts.

It should be noted in the foregoing structural formula, when a radical can be a substituent in more than one previously defined radical, that first radical can be selected independently in each previously defined radical. For example, $R^1$, $R^2$ and $R^3$ can each be $CONHOR_{12}$. $R^{12}$ need not be the same substituent in. each of $R^1$, $R^2$ and $R^3$ but can be selected independently for each of them.

Synthesis

The novel compounds of Formula (1) may be prepared using the reactions and techniques described in U.S. Pat. No. 5,138,069 and WO 93/10106 or one of its three U.S. counterparts, U.S. Pat. No. 5,130,439issued Jul. 14, 1992, U.S. Pat No. 5,206,374 issued Apr. 27, 1993, and U.S. Ser. No. 07/911,813 filed Jul. 10, 1992.

EXAMPLE I

Losartan Potassium [DUP 753]
Step A: Preparation of 4'-methylbiphenyl-2-carboxylic Acid
Methyl 4-methylbiphenyl-2-carboxylate (10.0 g, 44.2 mmol, 1 eq), 0.5 N KOH in methanol (265.5 ml, 133 mmol, 3 eq), and water (50 mL) were mixed and refluxed under N2. After 5 hours, the solvent was removed in ml and water (200 mL) and ethyl acetate (200 mL) added. The aqueous layer was acidified with concentrated hydrochloric acid to a pH of 3 and the layers were separated. The aqueous phase was extracted with ethyl acetate (2×200 mL), the organic layers collected, dried ($M_gSO4$) and the solvent removed in y3=to yield 8.71 g of a white solid; m.p. 140.0°–145.0° NMR (206 MHz, DMSO-$d_6$ δ 7.72 (d, 1H, J=7 Hz); 7.56 (t, 1H, J=7 Hz); 7.45 (d, 1H, J=7 Hz); 7.40 (t, 1H, J=7 Hz); 7.25 (9, 411); 2.36 (s, 3H). Anal. Calcd. for C14H12O2; C, 79.23; H, 5.70. Found: C, 79.22; H, 5.47.

Step B: Preparation of 4'-Methyl-2-cyanobiphenyl
4'-Methylbiphenyl-2-carboxylic acid (8.71 g, 41 mmol, 1 eq) and thionyl chloride (30.0 mL, 411 nmmol, 19 eq) were mixed and refluxed for 2 hours. The excess thionyl chloride was removed it vacuo and the residue was taken up in toluene. The toluene was removed by rotary evaporation and this toluene evaporation procedure was repeated to ensure that all of the thionyl chloride was removed. The crude-acidchloride was then added slowly to cold (0°) concentrated $NH_4OH$ (50 mL) so that the temperature was kept below 16°. After 15 minutes of stirring, water (100 mL) was added and solids precipitated. These were collected, washed well with water and dried under high vacuum over $P_2O_5$ in a dessicator overnight to yield 7.45 g of white solid; m.p. 126.0°-128.5°. NMR (200 MHz, DMSO-$d_6$) δ 7.65–7.14 (m, 10H), 2.32 (s, 3H). Anal. Calcd. for $C_{14}H_{13}NO$: C, 79.59; H, 6.20; N, 6.63. Found C, 79.29; H, 6.09; N, 6.52.

The above product amide (7.45 g, 35 mmol, 1 eq) and thionyl chloride (25.7 mL, 353 mmol, 10 eq) were mixed and refluxed for 3 hours. The thionyl chloride was removed using the same procedure as described above. The residue was washed with a little hexane which partly solubilized the product, but removed the impurity as well to yield 6.64 g of white solid, m.p. 44.0°–47.0°. NMR (200 MHz, DMS0-$d_6$) δ. 7.95 (d, 1H, J=8 Hz); 7.78 (t, 1H, J.7 Hz); 7.69–7.32 (m, 61-1); 2.39 (s, 3H). Anal Calcd. for $C_{14}K_{11}NC$, 87.01; 1–1, 5.74. Found C, 86.44; H, 5.88.

Step C: Preparation of 4'-bromomethyl-2-cyanobiphenyl
A solution of 5.59 g of 4'-methyl-2-cyanobiphenyl, 29 immol of N-bromosuccinimide, 9 mmol of benzoylperoxide and 500 mL of carbontetrachloride was refluxed for 3 hours. After cooling to room temperature, the resulting suspension was filtered and then concentrated in vacuo to provide the crude 4'-bromornethyl-2-cyanobiphenyl. The product was recrystallized from ether to yield 4.7 g of product; mp. 114.5°–120.0°. NMR (200 MHz, $CDCl_3$)δ 7.82–7.37 (m, 8H); 4.50 (s, 2H). Anal. Calcd. for $C_{14}H10B_rN$: C, 61.79, H, 3.70; N, 5.15. Found: C, 62.15; H, 3.45; N, 4.98.

Step D: Preparation of 2-n-butyl-4-chloro-1-[2'-cyanobiphenyl-4-yl)methyl]-5-(hydroxymethyl)-imidazole To a suspension of 1.43 g of sodium methoxide in 20 mL of dimethylformaqmide at 25° was added a solution of 15.3 mmol of 2-butyl 4(5)-chloro-5(4)-hydroxymethyl imidazole (prepared as described in U.S. Pat. No. 4,355,040) in 15 mL of DMF. The resulting mixture was stirred at 25° for 0.25 hours, and then to this mixture 4.6 g, 16.9 mmol of 4'bromomethyl-2-cyanobiphenyl in 15 mL of DMF. Finally, the reaction mixture was stirred at 40' for 4 hours. After cooling to 25% the solvent was removed in vacuo. The residue was dissolved in 1:1 hexane/ethyl acetate, and this solution was washed with water and brine, dried over anhydrous sodium sulfate, filtered, and concentrated. The crude product contains two regioisomers, the faster moving one by TLC, being the more potent isomer. Flash chromatography in 1:1 hexane/ethylacetate over silica gel to separate the regioisomeric products yielded 2.53 g of the faster eluting isomer. Recrystallization from acetonitrile yielded 1.57 g of analytically pure product; mp. 153.51°–155.5°. NMR (200 Mhz, $CDCl_3$)δ 7.82–7.43 (m, 6); 7.12 (d, 2, J=8 Hz); 5.32 (s, 2); 4.52 (s, 2); 2.62 (t, 2, J=7 Hz); 1.70 (t. of t, 2, J=7.7 Hz); 1.39 (t of q, 2, J=7.7 Hz); 0.90 (t, 3, J=7. Hz). Anal. Calcd. for $C_{22}H_{22}ClN_{3O}$: C, 69.56; H, 5.84; N, 11.06. Found: Q 69.45; 1–1, 5.89; N, 10.79.

Step E: Preparation of 2-n-butyl-4-chloro-5-hydroxymothyl-1-[(2'-(1H-tetrazol-5-yl) biphenil-4-yl) methyl]imidazole 2-n-Butyl-4-chloro-1-[(2-cyanobiphenyl-4 yl)methyl]-5-(hydroxymethyl) imidazole (11.93 g, 1.0 eq), sodium azide (3eq), and ammonium, chloride (3 eq) were mixed and stirred in DMF (150 mL) in a round bottom connected to a reflux condenser under $N_2$. An oil bath with a temperature controller was then used to heat the reaction at 100° C. for 2 days, after which the temperature was raised to 120° C., for 6 days. The reaction was cooled and 3 more equivalents of ammonium, chloride and sodium azide were added. The reaction was again heated for 5 more days at 120° C. The reaction was cooled, the inorganic salts filtered, and the filtrate solvent-removed in vacuo. Water (200 mL) and ethyl acetate (200 mL) were added to the residue and the layers were separated. The aqueous layer was extracted with ethyl acetate (2×200 mL), the organic layers were collected, dried ($M_gSO_4$) and the solvent removed in vacuo to yield a dark yellow oil. The product was purified by flash chromatography in 100% ethyl acetate to 100% ethanol over silica gel to yield 5.60 g of a light yellow solid. Recrystallization from acetonitrile yielded 4.36 g of light yellow crystals which still melted broadly. The crystals were taken up in 100 mL of hot acetonitrile. The solid that did not dissolve was filtered off to yield 1.04 g of product as a light yellow solid; m.p. 183.5°–184.5°. Upon cooling, the mother liquor yielded an additional 1.03 g of product as a light yellow solid; m.p. 179.0°–180.0°. NMR (200 MHz, DMSO-$d_6$ δ 7.75–7.48 (m., 4H); 7.07 (d, 2H, J=9 Hz); 7.04 (d, 2H, J=9 Hz); 5.24 (s, 2H); 5.24 (bs, 1H); 4.34 (s, 2H); 2.48 (t, 2H, J=7 Hz); 1.48 (t of t, 2H, J=7.7 Hz); 1.27 (t of q, 2H, J=7.7 Hz); 0.81 (t, 3H, J=7 Hz). Anal. Calcd. for $C_{22}H_{23}ClN_6O$: C, 62.48; H, 5.48; Cl, 8.38. Found for the solids which did not dissolve in 100 mL of acetonitrile: C, 62.73; 11, 5.50; Cl, 8.26. Found for the solids obtained from the mother liquor: C, 62.40; H, 5.23; Cl, 8.35.

EXAMPLE 2

2-butyl-1-[2'-[1H-tetrazol-5-yl)-biphenyl-4-yl)methy]-4-chloro-imidazole-5-carboxylic acid (EXP-3174)

A mixture of 2-butyl-S-hydroxymethyl-4-chloro-1-[2'-triphenylmethyltetrazol-5-il)-biphenyl-4-yl)methyl] imidazole and activated manganese dioxide in. 50 mL of methylene chloride was stirred at 25° C. At 24 hours into the reaction 2.00 g of manganese dioxide was added. After a total of 100 hours the reaction mixture was filtered with methylene chloride. The solids then were washed with methanol, and the methanol filtrate concentrated. The residue was dissolved in water. The resulting aqueous solution was adjusted to pH 3 using 10% hydrochloric acid and then extracted with 4:1 chloroformli-propanol. The combined organic phases were washed with brine, dried over anhydrous sodium sulfate, filtered, and concentrated. Column chromatography (elution(95:5:0.5 chloroform/methanol/acetic acid) furnished 2-butyl-1-[(2'-(1H-tetrazol-5-yl)-biphenyl-4-yl)methyl]-4-chloroimidazole-5-carboxylic acid as an amorphous solid. NMR (200 MHz, $DMSOd_6$): δ 7.46–7.63 (m, 4H), 7.05 (d, 2H, J=8 Hz), 6.93 (d, 2H, J=8 Hz), 5.56 (s, 2H), 4.10 (s, 12H), 2.55 (t, 2H , J=7.5 Hz), 1.44–1.52 (m, 2H), 1.17–1.28 (m, 2H), 0.78 (t, 311, J=7 Hz).

EXAMPLE 3

Step A: 2-(2'-Triphenylmethyl-2'H-tetrazol-5-yl) phenylboronic Acid

Alternative 1

To a 22 L flask under nitrogen purge was charged 8.25 L acetone, followed by 1.1 Kg 5-phenyltetrazole. Triethylamine (800 g) was added in such a rate that the temperature was maintained below 35° C. with some cooling. Solid trytil chloride was charged to this light suspension in five 440 g portions. The temperature was maintained below 35° C. An additional 1.38 L acetone was added to the reaction which was then maintained at 25° to 30° with stirring for 2 hours. Water (2.2 L) was added and the mixture was chilled to 15° to 20° C. The solid was collected by filtration; the filter cake was rinsed with 1.65 L 50% acetone-water followed by excess amount of water. The wet cake was re-slurried in 8 L acetone and 8 L of water was added slowly. The suspension was stirred for 1 hour then filtered. The filter cake was rinsed with 3 to 5 L of water. The white solid was dried in a vacuum oven at 40–45° C. to a constant weight of 3.0 Kg. mp 158–160° C.

To a dry 12 L flask under nitrogen purge was charged 3.19 L of dry tetrahydrofuran (THF). With agitation, 398 g of 5-phenyl-2-trityl-tetrazole prepared above was charged. The system was evacuated and released to nitrogen three times and then cooled to −20° C. A solution of butyl lithium in heptane (1.6 M, 447 g) was then added to the reaction mixture while maintaining the temperature at −15° C. to −20° C. The resultant deep red solution was stirred at −5° C. for 1 hour during which time the lithium salt crystallized out. The solid suspension was cooled to −25° C. again and 333 g triisopropylborate was charged at a temperature range of −20° to −25° C. After the addition, the mixture was allowed to warm to 20° C. without heating. About 2.5 L of solvent was removed by vacuum distillation. The pot temperature was kept below 40° C. To the mixture was added 2.66 L of 3% acetic acid in water and the resultant suspension was stirred for 1 hour. The white solid was collected by filtration. The solid cake was rinsed with 1.5 L of 20% tetrahydrofuran in water, followed by 3 L of water. The solid was dried under vacuum at room temperature to a constant weight of 502.3 g, mp 142–146° C. (dec.).

Alternative 2

A preferred alternative procedure for preparing the title compound of this Example 1 is by means of the following procedure.

5-Phenyltetrazole (14.6 g, 100 mmol) was suspended in dry THF (120 ml under nitrogen and triethylamine (14.8 ml, 105 mmol) was added while the temperature at 15 to 20° C. Triphenylchloromethane (29.3 g, 105 mmol) in dry THF (60 ml) was then added slowly to the mixture at 15 to 20° C. After the addition was complete the mixture was warmed to 35° C. for 1 hour and then cooled at 0° C. for 1 hour. The precipitated triethylammonium chloride was filtered and the filtrate was degassed via vacuum/nitrogen purges (3×). The degassed solution was cooled to −20° C. and butyllithium (1.6 M in hexanes) was added until a pink color persisted for 2 minutes. The pink color indicated that the solution was completely dry. More butyllithium (65.6 ml, 105 mmol) was charged at ⇔−15° C. The deep red heterogeneous mixture was aged at −20 to −15° C. for 1 hour and triisopropylborate (30.6 ml, 130 nmol) was added while maintaining the temperature at −⇔−15° C.

The deep red solution was aged at −15° C. for 30 minutes and then warmed to 10° C. over 1 hour. The mixture volume was reduced by ~200 ml in vacuo at ⇔ 15° C. at which time <5% of hexanes (vs THF) remained. The residue was diluted with THF to a total volume of 160 ml and isopropanol (60 ml) was added. The solution was cooled to 0° C. and saturated aqueous ammonium choride (40 ml, 200 mmol) was charged within 15 minutes. The mixture was aged at 20 to 25° C. for 30 minutes and water (100 ml) was added over 30 to 45 minutes. After aging the mixture for 1 hour, the crystallized product was collected by filtration and washed with cold 80% aqueous isopropanol. The filter cake was airdried on the filter to give 69.7 g (86% yield, corrected for 82% purity) of product as the THF mono-solvate.

Step B: 2-n-butyl-4-chloro-5-hydroxymethyl-1-p-bromobenzyl-1H-imidazole

A suspension of 2-n-butyl-4-chloro-1H-imidazole-5-carboxyaldehyde (146.9 g, 0.78 mol) and p-bromobenzyl bromide (195 g, 0.78 mol) in dimethylacetamide (1.0 L) was cooled to 0° C. and potassium carbonate (1.38 g, 1.0 mol) was added. The mixture was aged for three hours at 0° C. and then at 20 to 25° C. or two to four hours. The mixture was diluted with dimethylacetamide (0.15 L) and then filtered. The filter cake was washed with dimethylacetamide (50 ml). The combined filtrates were diluted with methanol (0.66 L) and cooled to 0° C. Sodium borohydride (37.8 g, 1.0 mol) was added as a solid and the mixture was aged with stirring at 20 to 25° C. for two hours. Water (1.56 L) was added slowly to crystallize the product. The filter cake was washed carefully with water (1.56 L) and dried in vacuo at 60° C. The yield was 255 g (91%, corrected for 99.5% purity).

Step C: 2-n-butyl-4-chloro-1-[(2'-(2-triphenylmethyl-2H-tetrazol-5-yl)-1,1'-biphenyl-4-yl)methyl]1H-5-methanol All operations described for this example were performed under an atmosphere of nitrogen.
Catalyst Preparation To a mixture of palladium chloride (10.6 mg) and triphenylphosphine (31.5 mg) was added anhydrous toluene (4 ml). The heterogeneous solution was degassed by vacuum/nitrogen purges (3×) and then heated to 60° C. for 30 minutes. Triisopropylphosphite (30.0. microliters) was added and the mixture was further heated at 60° C. until a homogeneous solution was obtained (1 to 2 hours).
Coupling 2-(2'-triphenylmethyl-25-tetrazol-5'-yl)phenylboronic acid of Example 3, Step A (1.3 g) was suspended in toluene (4 ml) and water. (100 microliters) was added. The heterogeneous mixture was stirred at room temperature for 30 minutes and potassium carbonate (0.7 g) was then charged followed by the titled product of Example 3, Step B (0.7 g). The mixture was degassed via vacuum/nitrogen purges (3×) and the abovecatalyst solution was added. The temperature of the mixture was raised 80 to 86° C. and kept at this temperature for 2 hours. After the mixture was cooled to 40° C., water (5 ml) was added. The aqueous layer was removed and the organic phase was concentrated in vacuo at . . . 30° C. to a volume of ~3 ml Methyl i-butyl ketone (MIBK (8 ml) was added and the mixture was again reduced to ~3 ml. The mixture was diluted with, MIBK (4 ml) and water (36 microliters), heated to 6011C and then cooled and aged first at 0° C. for 30 minutes followed by aging at −10° C. with stirring for 2 hours. The crystallized product was collected by filtration as a mono-MIBK solvate (1.44 g, 94% yield). The crude product was dissolved in MIBK (2.1 ml) at 80° C., the solution was filtered hot at 80° C. and water (33.8 microliters) was added. The solution was cooled slowly to 0° C. over 1 hour and aged at 0° C. for 30 minutes followed by aging at −10° C. with stirring for 2 hours. After filtration 1.38 g of the mono-MIBK solvated product was recovered (90% yield).

EXAMPLE 4

2-n-Butyl-4-chloro-1-[(2"(2-triphenylmethyl-2H-tetrazol-5-yl)-1,1'-biphenyl-4-yl)methyl]-1H-imidazole-5-methanol All operations described for this example were performed under an atmosphere of nitrogen.
Step A: Catalyst Preparation The following two procedures can be used with similar results.
Alternative Procedure 1

To a mixture of palladium chloride (354 mg) and triphenylphosphine (2.1 g) was added anhydrous tetrahydrofuran (THF) (75 ml). The heterogeneous solution was degassed by vacuum/nitrogen purges (3×) and then refluxed for 4 hours.

Most of the palladium chloride changed over to bis(triphenylphosphine)palladium chloride during the reflux. Some insoluble black solids were still observed at this point.

The heterogeneous THF solution containing the phosphinated palladium chloride was cooled to room temperature and diethylzinc (4.0 ml, 1 M in hexanes) was added. Except for a small amount of black solids, the solution essentially became homogeneous after stirring for 30 minutes. This activated catalyst solution was used in the coupling step described below.
Alternative Procedure 2

To a mixture of palladium chloride (354 mg) and triphenylphosphine (2.1 g) was added anhydrous THF (75 ml). The heterogeneous solution was degassed by vacuum/nitrogen purges (3×) and then triisopropylphosphite (0.99 ml) was added. The mixture was maintained at room temperature until all the palladium chloride was dissolved and a homogeneous solution was obtained (0.5 to 1 hour).
Step B: Benzyltrimethylammonium Carbonate Preparation To a benzyltrimethylammonium hydroxide solution (42 g) was added ammonium carbonate (5.0 g) and the reaction was aged with stirring until all of the ammonium carbonate dissolved (30 minutes) The methanol solvent was removed in vacuo and further displaced with THF (3×10 ml). The residual carbonate was dissolved in THF (90 ml).
Step C: Coupling Step To the carbonate solution prepared in Example 4, Step B was charged the titled, product of Example 3 (24.0 g) and the titled product of Example 3, Step B (14.2 g). The mixture was degassed by vacuum/nitrogen purges (5×), followed by the addition of the catalyst solution prepared as recited in Example 4, Step A (procedure 1 or 2). The reaction mixture was heated to reflux, aged until completion (8 to 10 hours), cooled to room temperature and filtered through a pad Celite. The Celite was further is washed with-THF-(3×10 ml). The yield was 89 wt %.

EXAMPLE 5
2-n-Butyl-4-chloro-1-[(2'-(tetrazol-6-yl)-1,1'-biphenyl-4-yl)methyl]-1H-imidazole-5-methanol Potassium Salt 2-n-butyl-4-chloro-1-[((2'-2-triphenylmethyl-2H-tetrazol-5-yl)-1,1'-biphenyl-4-yl)methyl]-1H-imidazole-5-methanol (5.0 g, 6.54 mmol) was dissolved in THF (60 ml). 4 N Sulfuric acid (38 ml, 152 mmol) was added with stirring at 25 to 30° C. The solution was aged overnight at 20 to 25° C. and isopropyl acetate (60 ml) was then added The layers were separated and the organic phase was back-extracted with 4 N sulfuric 15 acid (19 ml). The aqueous layers were combined and the organic solvents (THF and isopropyl actate) were removed in vacuo. The remaining aqueous solution was diluted with THF (10% of THF by volume) and passed through a pad of Ecosorb_S 402 (5.0-g). The pad was rinsed with 1Q% THF in 4 N sulfuric acid. The filtrate was then passed through a column of SP-20.700 ml) and the column was washed with water (180 ml) followed with −1 M K2HPO4 (180 ml). The pH of the eluent was monitored to ensure complete potassium salt formation. Further washing with water (180 ml) removed the sulfate and excess phosphate. The potassium salt product was eluted with 20% aqueous THF. Concentration of the aqueous solution and dilution with isopropanol gave crystalline product. Alternatively, the product was isolated by spray drying. The yield was 2.56 g (85%).

EXAMPLE 6
1-Bromo-4-(2'-n-butyl-4'-chloro-5'-hydroxymethylimidazole-1'H-1'-yl)methylbenzene
Step A: Alkylation To 200 mL of dimethyl acetamide under a nitrogen atmosphere in a 1-liter 3-necked flask fitted with a mechanical stirrer and thermocouple is charged 30.8 g (0.163 mol) of 2-n-butyl-4-chloro-5 formyl-1H-imidazole and 43.7 g (0.16 mol) of 4-bromobenzyl bromide. The solution is cooled to −5T followed by portion wise addition of 27.1 g (0.19 mol) of powdered potassium carbonate over 1.0 min with rapid stirring while keeping the reaction temperature between −5–011C. The slurry is stirred at −5° C. for 2 h and room temperature for 2 h or until the alkylation is complete.
Step B: Filtration The slurry is filtered and the cake is washed with an anhydrous mixture of dimethyl acetamide (30 mL),and methanol (130 mL). The filtrate is used directly in the next step.
Step C: Reduction Under a nitrogen atmosphere, 1.85 g (48 mmol) of powdered sodium borohydride is added portionwise over 0.5 h to the filtrate at −15° C. in a 5-liter 3-necked flask with a mechanical stirrer and a thermocouple, keeping the reaction temperature between −15 to −5T. The mixture is warmed to room temperature and aged for 1 h or until the reduction is complete.
Step D: Crystallization Acetic acid (2.74 mL) in added dropwise: over 10 min with rapid stirring while keeping the temperature of the mixture at 20–25T. This mixture is aged at room temperature for 0.5 h, followed by the addition of water (160 mL) dropwise over 1' h. The solution is seeded with imidazole 0.4 and followed by the addition of water (160 mL) dropwise over 1 h. The product precipitated within 0.5 h. The slurry is aged at room temperature for 2 h, cooled to 100 C., aged for 0.5 h and the solid is filtered. The cake is washed with 320 mL of water, suction dried under nitrogen at room temperature for 2 h and oven dried under house vacuum (−24 psi) at <60° C. for 12 h to afford 54.3 g of titled imidazole as a white solid (HPLC assay: 98.8 A%, 97.2 W%, overall yield: 92.4%, 0.5 W% of the regioisomer).

EXAMPLE 7
2-n-Butyl-4-chloro-1-[(2'-(2-triphenylmethyl-2H-tetrazol-5-yl)-1,1'-biphenyl-4-yl)methyl]-1H-imidazole-5-methanol
Step A: Catalyst Preparation Triphenylphosphine (262 mg, 1.0 mmol is dissolved in THF (20 mL) and the solution is degassed by vacuum/nitrogen purges M). Palladium acetate (56 rag, 0.25 mmol) is added and the solution is degassed again (3×). The resulting solution is warmed to 60° C. for 30 min. and then cooled to 25° C.
Step B: Coupling Note: All solvents must he degassed.

2-(2'-triphonylmethyl-2'H-tetrazol-5'-yl)phenylboronic acid 15.4 g, 26.7 mmol, 75 wt % pure) is suspended in diethoxy-methane (DEM) (80 mL, KF-0.5 500 mg/ml)., Water (0.55 mL, 31 mmol) is added and the slurry is aged at ambient temperature for 30 min. After the age, another charge of water (0.55 mL, 31 mmol) is added to the boronic acid suspension under agitation. The slurry is then treated with powdered potassium carbonate (8.6 g, 62 mmol) and alkylated imidazole, the titled product of Example 22 (8.97 g, 25 mmol). The mixture is aged at 20–25° C. for 30 min then degassed well (M). (Note: in the pilot plant, degassing takes much longer and can be started immediately after the imidazole and carbonate are added). The catalyst solution is then charged and the mixture is heated to reflux (76–79° C.). The reaction is complete in 2–6 hours. When the imidazole has been consumed, water (30 mL) and THF (25 ml) are added and the mixture is stirred at 55–6011 C. The water layer is separated and the organic layer is washed with water (30 mL). The organic layer is concentrated in vacuo to a volume of 50 ml to remove most of the THF. More DEM (50 ml) is added and removed by distillation to further reduce THF to ⇔5 vol %. The residual organic solution is diluted with warm (60° C.) DEM (to a final volume of 75 ml) and water (0.5 ml, 28 mmol). The mixture 1 e is-then cooled slowly to −1211 C over 2 hours. After aging at −12° C. for 1 hour, the product is collected by filtration. The cake is washed with cold DEM (25 mL). Vacuum drying at 400C gave 15.59 (93%) of the titled product (non-solvated). [Pd 600 to 1000 ppm.]

EXAMPLE 8
2-n-Butyl-4-chloro-1-[(2-(2-triphenylmethyl-2H-tetrazol-5-yl)-1,1'-biphenyl-4-yl)methyl]-1H-imidazole-5-methanol
Step A: Catalyst Preparation Triphenylphosphine (262 mg, 1.0 mmol) is dissolved in THF (20 mL) and the solution is degassed by vacuum/nitrogen purges (3×). Palladium acetate (56 mg, 0.25 nmol) is added and the solution is degassed again=). The resulting solution is warmed to 60° C. for 30 min. and then cooled to 25T.
Step B: Coupling Note: All solvents must be degassed.

2-(2'-Triphenylmethyl-2'H-tetrazol-5'-yl) phenylboronic acid (15.4 g, 26.7 mmol, 75 wt % pure) is suspended in diethoxy-methane (DEM) (80 mL, NF £ 500 mg/ml). Water (0.55 mL, 31 mmol) is added and the slurry is aged at ambient temperature for 30 min. After the age, another charge of water (0.55 ml, 31 mmol) is added to the boronic acid suspension under agitation. The slurry is then treated with powdered potassium carbonate (8.6 g, 62 mmol) and the titled product of Example 22, the alkylated imidazole (8.97 g, 25 mmol). The mixture is aged at 20–25° C. for 30 min then degassed well (3×). (Note: in the pilot plant, degassing takes much longer and can be started immediately after the imidazole and carbonate are added) The catalyst solution is then charged and the mixture is heated to reflux (76–79° C.). The reaction is complete in 2–6 hours. When the imidazole has been consumed, water (30 mL) and THF (25 ml) are added and the mixture is stirred at 55–60° C. The water layer is separated and the organic layer is washed with water (30 ml). Tributylphosphine (0.62 ml, 10 mol %) is added and the organic layer is concentrated in vacuo to a volume of 50 ml to remove most of the THF. More DEM (50 ml) is added and removed by distillation to further reduce THF to ⇔5 vol, %. The residual organic solution is diluted with warm (60° C.) DEM (to a final volume of 75 ml) and water (0.5 ml, 28 mmol). The mixture is then cooled slowly to −120 C. over 2 hours. After aging at −12° C. for 1 hour, the product is collected by filtration. The cake is washed with cold DEM (25 mL). Vacuum drying at 40° C. gave 15.6 g (93%) of the titled product (non solvated). Pd-n 10 ppm].

EXAMPLE 9
2-n-Butyl-4-chloro-1-[(2-(2-triphenylmethyl-2H-tetrazol-5-yl)-1,1'-biphenyl-4-yl)methyl]-1H-imidazole-5-methanol as the Methyl Isobutyl Ketone Solvate A suspension of the titled product of Example 7 (5 g) in methyl isobutyl ketone (MIBK) (40 ml) is degassed (3×) and tributylphosphine (0.12 g, 8 mol %) is added. The mixture is heated to 85° C. at which time a homogeneous solution was, obtained. Degassed water (0.136 g, 100 mol %) is then added and the solution is cooled to −10° C. over 2 hours. The heterogeneous solution is aged at −10° C. for 2 hours, the crystallized product is collected by filtration and washed with cold MIBK (4011 C, 15 ml). The recovery was 5.40 g of the titled product (93.9 as the MIBK solvate).

EXAMPLE 10
2-n-butyl-4-chloro-1-[(2'-(tetrazol-5-yl)-1,1'-biphenyl-4-yl)-methyl]-1H-imidazole-5-methanol Potassium Salt
Step A: Deprotection Dissolve 2.50 g of the titled product of Example 8, the methyl isobutyl ketone solvate, by adding 10 mL of 0.75 M $H_2SO_4$ in 50:50 MeCN:-water. Age 2 hours 25 min, 23–25° C. Add 15 mL of water in 2 min (can be added in 30 min to an hour in larger scales), and age 1.75 hours, 23–25° C. Filter and wash with 6 mL of 20:80 MeCN:water. There was almost no starting material left in the trityl alcohol filter cake (<0.05 area%).

Step B: Free Acid Formation

Dilute the above filtrate with 13 mL of MeCN. The pH of the solution is 1.50. The temperature of the solution following neutralization and crystallization was 22–24° C. After adding 1.5 mL of 3 N NaOH (pH 1.75–1.65), the reaction is seeded with 20 mg of the free acid. Age 15 min. Slowly add the next 1 mL of 3 M NaOH to allow for o>0 good crystal growth (on this scale, the addition time was 5–10 min). Age 30 min. Add the remaining 3 M NaOH (pH 3.60–3.50). Age 1 hour. The white slurry is filtered and washed with 5 mL of 20:80 MeCN:water then 10 mL of water. A thorough water wash of the free acid filter cake is necessary to remove all the salts. The wash can be checked for $SO_4^{-2}$. The filter cake is dried in a vacuum oven at 35° C. for 18 hours with nitrogen purge. The yield of the free acid was 1.28 g (92.5%) and there was 54 mg-(4%) of the free acid in the mother liquors.

Step C: Salt Formation

To 4.0 g (9.46 mmoles) of the free acid is added 10.9 ml of 0.842N KOH solution all in one portion. The slurry is aged at room temperature for 30 minutes, during which time most of the solid dissolves. The cloudy solution is filtered and the solids collected on a sintered glass funnel. The pH of the filtrate is measured at 9.05. The aqueous solution is added slowly to a refluxing azeotropic: mixture of cyclohexane/isopropanol (69° C.) whereupon the ternary azeotrope cyclohexane/isopropanol/water (64° C.) begins to distill. When the solution is dry the temperature of the overhead rises to 69° and the potassium salt crystallizes. When the water content of the pot is <0.05% the distillation is halted and the white slurry is cooled to room temperature. The white crystalline solid is collected on a sintered glass funnel and washed with 10–15 ml of cyclohexane/isopropanol 67/33 and dried in a vacuum oven (wt 3.8 g yield 95%).

Utility

The hormone angiotensin II (AII) produces numerous biological responses (e.g. vasoconstriction) through stimulation of its receptors on cell membranes. For the purpose of identifying compounds such as AII antagonists which are capable of interacting with the AII receptor, a ligand-receptor binding assay was utilized for the initial screen. The assay was carried out according to the method described by [Glossmann, et al., J. Biol-Chem., 249, 825 (1974)], but with some modifications. The reaction mixture contained rat adrenal cortical microsomes (source of AII receptor) in Tris buffer and 2 nM of 3H-AII with or without potential AII antagonist. This mixture was incubated for 1 hour at room temperature and the reaction was subsequently terminated by rapid filtration and rinsing through glass micro-fibre filter. Receptor-bound 3H-AII trapped in filter was quantitiated by scintillation-counting. The inhibitory concentration (IC50) of potential AII antagonist which gives 50% displacement of the total specifically bound 3H-AII is presented as a measure of the affinity of such compound for the AII receptor (See Tables 1 and 2).

The potential antihypertensive effects of the compounds of this invention may be demonstrated by administering the compounds to awake rats made hypertensive by ligation of the left renal artery [Cangiano, at al., J. Pharmacol. Exp. Ther., 208, 310 (1979)]3. This procedure increases blood pressure by increasing renin production with consequent elevation of AII levels. Compounds are administered orally at 100 mg/kg and/or intravenously via a cannula in the jugular vein at 10 mg/kg. Arterial blood pressure is continuously measured directly through a carotid artery cannula and recorded using a pressure transducer and a polygraph. Blood pressure levels after treatment are compared to pretreatment levels to determine the antihypertensive effects of the compounds (See Table 1).

TABLE 1

| Ex No. | Angiotensin II Receptor Binding IC50 (μmolar) | Antihypertensive Effects in Renal Hypertensive Rats | |
|---|---|---|---|
| | | Intravenous Activity[1] | Oral Activity[2] |
| Losartan | 0.039 | + | + |

[1]Significant decrease in blood pressure at 10, mg/kg or less
[2]Significant decrease in blood pressure at 100 mg/kg or less Compounds listed in Table 2 were tested in the same manner as described for Table 1, except that in the test for anti hypertensive effects in renal hypertensive rats, the compounds were administered orally at 30 mg/kg and intravenously at 3 mg/kg.

TABLE 2

| Ex No. | Angiotensin II Receptor Binding IC50 (μmolar) | Antihypertensive Effects in Renal Hypertensive Rats | |
|---|---|---|---|
| | | Intravenous Activity[1] | Oral Activity[2] |
| EXP-3174 | 0.011 | + | + |

[1]Significant decrease in blood pressure at 3.0 mg/kg or less
[2]Significant decrease in blood pressure at 30 mg/kg or less The hypotensive effects of 2-butyl-4-chloro-1-[(2'-(1H-tetrazol-5-yl)biphenyl-4-yl)methyl]-5-hydroxymethylimidazole sodium salt were compared before and after furosemide administration to conscious Dogs. Cumulative intravenous injections of imidazole at 0.3 to 3 mg/kg did not lower blood pressure in normotensive conscious Dogs (n=4, FIG. 1) but they were effective in inhibiting the pressor response to AII (0.1 gg/kg IV) determined at 10 min post dose (FIG. 2). Plasma renin activity (PRA) in these animal was 1.5:L ,50.5 ng Al/ml/hr. Four days later, furosemide was given to three of these dogs at 10 mg/kg im at 18 and 2 hours before the experiment and increased PRA to 19.9 t 7.2 ng Al/ml/hr. Imidazole was then given cumulatively iv at the same doses and caused a significant decrease in blood 0 pressure in a dose-dependent manner (FIG. 1). It also inhibited the pressor response to AII at the two higher doses (FIG. 2). A similar hypotensive enhancement by furosemide was also observed with captopril at 0.3 mg/kg iv (FIG. 2). These results indicate that diuretics enhance the hypotensive efficacy of imidazole AII blockers. Thus a combined therapy of these two classes of drugs will be likely to increase the response rate to therapy among hypertensive patients.

The angiotensin II receptor antagonist compounds are useful at increasing the survival rate of transplant patients, including renal and heart transplant patients, using a therapeutically effective amount of a compound of Formula I. These compounds are also useful as a method for treating and preventing chronic rejection in renal transplant patients using a therapeutically effective amount of an angiotensin II receptor antagonist compound of Formula I. These compounds are useful for reducing proteinuria in renal transplant patients using a therapeutically effective amount of an angiotensin II receptor antagonist compound of Formula I. The compounds are useful for treating post-transplant hypertension in renal transplant patients using a therapeutically effective amount of an angiotensin II receptor antagonist as recited above.

Dosage Forms

The compounds of this invention can be administered for the treatment of hypertension according to the invention by any means that effects contact of the active ingredient compound with the site of action in the body of a warm blooded animal. For example, administration, can be parenteral, i.e., subcutaneous, intravenous, intramuscular or intra peritoneal. Alternatively, or concurrently in some cases administration can be by the oral routes.

The compounds can be administered by any conventional means available for use in conjunction with pharmaceuticals, either as individual therapeutic agents or in a combination of therapeutic agents. They can be administered alone, but are generally administered with a pharmaceutical carrier selected on the basis of the chosen route of administration and standard pharmaceutical practice.

For the purpose of this disclosure, a warm-blooded animal is a member of the animal kingdom possessed of a homeostatic mechanism and includes mammals and birds.

The dosage administered will be dependent on the age health and weight of the recipient, the extent of disease, kind of concurrent treatment, if any, frequency of treatment and the nature of the effect desired. Usually, a daily dosage of active ingredient compound will be from about 1–500 milligrams per day. Ordinarily, from 10 to 190 milligrams per day in one or more applications is effective to obtain desired results. These dosages are the effective amounts both for treatment of hypertension and for treatment of congestive heart failure, i.e., for lowering blood pressure and for correcting the hemodynamic burden on the heart to relieve the congestion.

The active ingredient can be administered orally in solid dosage forms, such as capsules, tablets, and powders, or in liquid dosage form, such as elixirs syrups, and suspensions. It can also be administered parenterally, in sterile liquid dosage forms.

Gelatin capsules contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols; are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. in addition, parenteral solutions can contain preservatives, such as benzalkonium chloride, methyl or propylparabon, and chlorobutanol.

Suitable pharmaceutical carriers are described in Remington's Pharmaceutical Sciences A. Osol, a standard reference text in this field.

Useful pharmaceutical dosage-forms for administration of the compounds of this invention can be illustrated as follows:

Capsules

A large number of unit capsules are prepared by filling standard two-piece hard gelatin capsules, each with 100 milligrams of powdered active ingredient, 150 milligrams of lactose, 50 milligrams of cellulose, and 6 milligrams magnesium stearate.

Soft Gelatin Capsules

A mixture of active ingredient in a digestible oil such as soybean oil, cottonseed oil or olive olil is prepared, and injected by means of a positive displacement pump into gelatin to form soft gelatin capsules containing 100 milligram of the active ingredient. The capsules are washed and dried.

Tablets

A large number of tablets are prepared by conventional procedures so that the dosage unit is 100 milligrams of active ingredient 0.2 milligrams of colloidal silicon dioxide, 5 milligrams of magnesium stearate, 275 milligrams of microcrystalline cellulose, 11 milligrams of starch, and 98.8 milligrams of lactose. Appropriate coatings may be applied to increase palatability or delay absorption.

Injectable

A parenteral composition suitable for administration by injection is prepared by stirring 1.5% by weight of active ingredient in 10% by volume propylene glycol. The solution is made to volume with water for injection and sterilized.

Suspension

An aqueous suspension is prepared for oral administration so that each 5 milliliters contain 100 milligrams of finely divided active ingredient, 100 milligram of sodium carboxymethyl cellulose, 5 milligrams of sodium benzoate, 1.0 grams of sorbitol solution, U.S.P., and 0.025 milliliters of vanillin.

The same dosage forms can generally be used when the compounds of this invention are administered stepwise in conjunction with another therapeutic agent. When drugs are administered in physical combination, the dosage form and administration route should be selected for compatibility with both drugs. Suitable dosages, dosage forms and administration routes are illustrated in Table 3.

TABLE 3

Examples of diuretics that can be combined with AII blockers of this invention:

| Drug | Dose | Formulation | Route |
|---|---|---|---|
| Benzothiadizides (e.g. hydrochlorothiazide) | 5–100 mg (daily) | Tablet | Oral |
| Loop diuretics (e.g. furosemide) | 50–80 mg (daily) | Tablet | Oral |

When used with diuretics, the initial dose of AII blocker can be less, e.g., 1–100 milligrams per day and for the more active compounds 1–10 milligrams per day. Angiotensin II (AII) Receptor Blockade, but Not Calcium Channel Antagonism, Limits Chronic Allograft Failure and Prolongs Life in a Rate Model, S. C. Amuchastegui, N. Azzolini, M. Mister/A. Pezzotta, N. Perico & G. Rumuzzi. Mario Negri Institute & Ospedali Riuniti di Bergamo, Italy.

Functional and structural changes of chronic renalallograft failure share similarities with other chronic nephropathies with low nephron numbers. Here we gave the type 1 AII receptor antagonist DUP 753 (30 mg/kg/day in the drinking water, n=6) or the calcium, (Ca) channel blocker lacidipine (1 mg/kg/day by gavage, n=6), or no treatment (n=5) to bilaterally nephrectomized Lewis, rats transplanted with kidney from Fisher 344 donor rat. Transplanted rats received cyclosporine (5 mg/kg/day i.m.) for the first 10 days to prevent acute rejection, and doses of antihypertensive drugs were adjusted to maintain blood pressure within the normal range.

Results at the end of the 6 month follow-up were as follows (mean ±SD, #P<0.03 vs, DUP 753 and isograft; *P<0.05 vs all other groups; ° P<0.05 vs DUP 753 and isograft):

| | Animal survival | SBP mm HG | Proteinuria mg/day | FSGS % (range) |
|---|---|---|---|---|
| A-None | 40% # | 152 ± 2* | 115 ± 12 | 50 (50–50) |
| A-DUP 753 | 100% | 114 ± 12 | 71 ± 46 | 3 (0–10) |
| A-Lacidipine | 34% | 125 ± 7 | 167 ± 26° | 15 (10–20) |
| Isograft | 100% | 115 ± 14 | 51 ± 21 | 0 (0–0) |

GFR, as inulin clearance, was higher in DUP 753 (1.89±13 ml/min) and in lacidipine (1.32±67 ml/min) than in untreated (0.61±0.21 ml/min) allograft rats surviving the 6 month follow-up. Thus at comparable level of SBP control DUP 753 but not lacidipine effectively protects animals from chronic allograft injury and allows long-term animal survival. These findings confirm previous human studies in chronic nephropathies and suggest that in the future AII or ACE inhibitors should probably replace Ca channel blockers, now the single most used anthypertensives in post-transplant hypertension.

What is claimed is:

1. A method for increasing the survival rate of transplant patients comprising administering to said patients a therapeutically effective amount of an angiotensin II receptor antagonist compound of formula I:

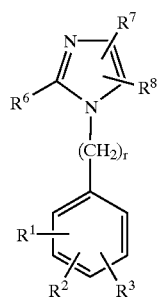

wherein $R^1$ is:

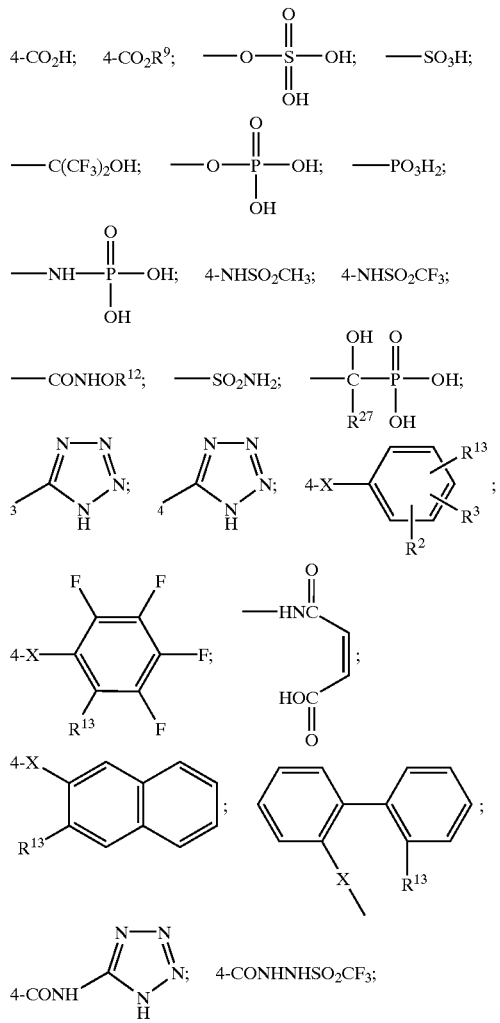

-continued

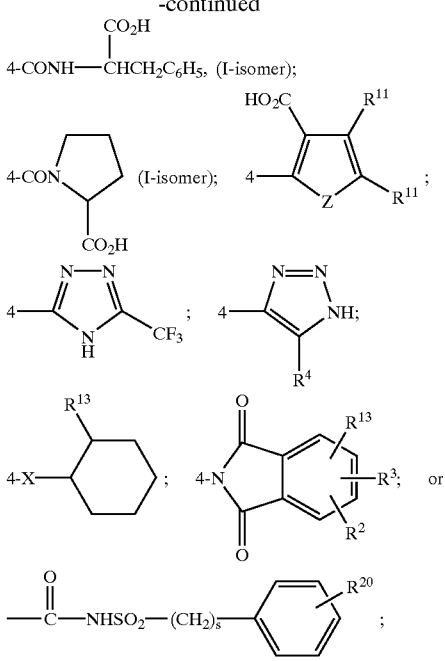

$R^2$ is H; Cl; Br; I; F; $NO_2$; CN; alkyl of 1 to 4 carbon atoms; acyloxy of 1 to 4 carbon atoms; alkoxy of 1 to 4 carbon atoms; $CO_2H$; $CO_2R^9$; $HNSO_2CH_3$; $NHSO_2CF_3$; $CONHOR^{12}$; $SO_2NH_2$;

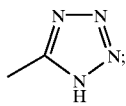

aryl; or furyl;

$R^3$ is H; Cl, Br, I or F; alkyl of 1 to 4 carbon atoms or alkoxy of 1 to 4 carbon atoms;

$R^4$ is CN, $NO_2$ or $CO_2R^{11}$, $R^5$ is H, alkyl of 1 to 6 carbon atoms, cycloalkyl of 3 to 6 carbon atoms alkenyl or alkynyl of 2 to 4 carbon atoms;

$R^6$ is alkyl of 2 to 10 carbon atoms, alkenyl or alkynyl of 3 to 10 carbon atoms or the same groups substituted with F or $CO_2R^{14}$; cycloalkyl of 3 to 8 carbon atoms, cycloalkylalkyl, of 4 to 10 carbon atoms; cycloalkylalkenyl or cycloalkylalkynyl 5 to 10 carbon atoms; $(CH_2)sZ(CH_2)MR^5$ optionally substituted with F or $CO_2R^{14}$; benzyl substituted on the phenyl ring with 1 or 2 halogens, alkoxy of 1 to 4 carbon atoms, alkyl of 1 to 4 carbon atoms or nitro;

R7 is H, F, Cl, Br, 1, $NO_2$, $C_vF_{2v}+1$, where v=1–6, $C_6F_5$; CN;

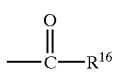

straight or branched alkyl of 1 to 6 carbon atoms; phenyl or phanylalkyl, where alkyl is 1 to 3 carbon atoms; or substituted phenyl or substituted phenylalkyl, where alkyl is 1 to 3 carbon atoms, substituted with one or two substituents selected from alkyl of 1 to 4 carbon atoms, F, Cl, Br, OH, $OCH_3$, $CF_3$, and COOR, where R is H, alkyl of 1 to 4 carbon atoms, or phenyl;

$R^8$ is H, CN, alkyl of 1 to 10 carbon atoms, alkenyl of 3 to 10 carbon atoms, or the same groups substituted with F; phenylalkenyl wherein the aliphatic portion is 2 to 6 carbon atoms; —$(CH_2)$m-imidazol-1-yl; —$(CH_2)$m-1,2,3-triazolyl optionally substituted with one or two group selected from $CO_2CH_3$ or alkyl of 1 to 4 carbon atoms; —$(CH_2)_s$ tetrazolyl;

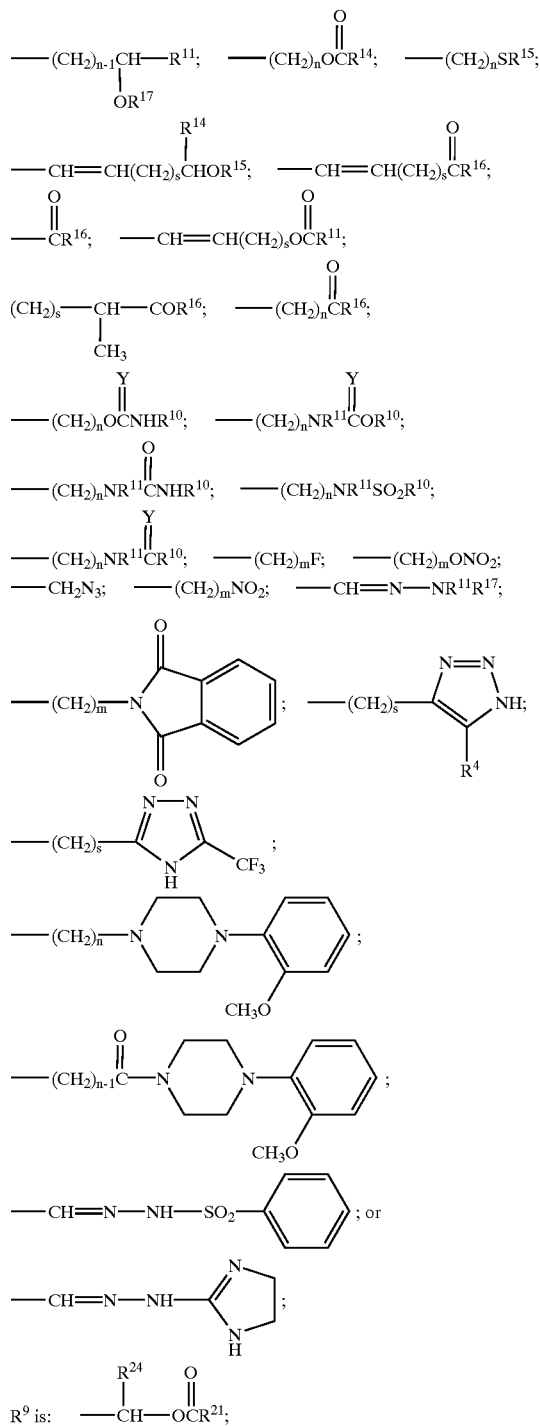

$R^{10}$ is alkyl of 1 to 6 carbon atoms or perfluoroalkyl of 1 to 6 carbon atoms, 1-adaman 1-naphthyl, 1-(1-naphthyl)ethyl, or $(CH_2)_pC_6H_5$;

$R^{11}$ is H, alkyl of 1 to 6 carbon atoms, cycloalkyl of 3 to 6 carbon atoms, phenyl or benzyl;

$R^{12}$ is H, methyl or benzyl;

R13 is —CO$_2$H; —CO$_2$R$^9$; —CH$_2$CO$_2$, CH$_2$CO$_2$R$^9$;

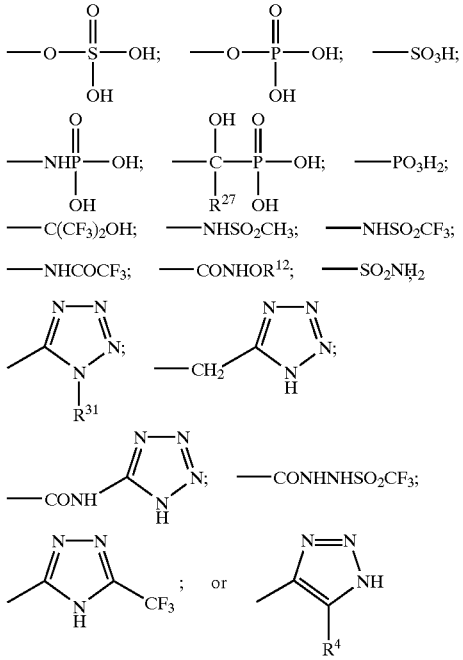

$R^{14}$ is H, alkyl or perfluoroalkyl of 1 to 8 carbon atoms, cycloalkyl of 3 to 6 carbon atoms, phenyl or benzyl;

$R^{15}$ is H, alkyl of 1 to 6 carbon atoms, cycloalkyl of 3 to 6 carbon atoms, phenyl, benzyl, acyl of 1 to 4 carbon atoms, phenacyl;

$R^{16}$ is H, alkyl of 1 to 6 carbon atoms, cycloalkyl of 3 to 6 carbon atoms, (CH$_2$)$_p$C$_6$H$_5$, OR$^{17}$, or NR$^{18}$R$^{19}$;

$R^{17}$ is H, alkyl of 1 to 6 carbon atoms, cycloalkyl of 3 to 6 carbon atoms, phenyl or benzyl;

$R^{18}$ and $R^{19}$ independently are H, alkyl of 1 to 4 carbon atoms, phenyl, benzyl, →-methylbenzyl, or taken together with the nitrogen form a ring, of the formula

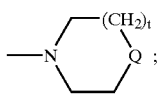

Q is NR20, O or CH2;

R20 is H, alkyl of 1–4 carbon atoms, or phenyl;

R21 is alkyl of 1 to 6 carbon atoms, —NR22R239 or

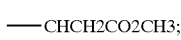

R22 and R23 independently are H, alkyl of 1 to 6 carbon atoms, benzyl:, or are taken together as (C112)u where u is 3–6;

$R^{24}$ is H, CH$_3$ or —C$_6$H$_5$;

$R^{25}$ is NR$^{27}$R$^{28}$, OR$^{28}$, NHCONH$_2$, NHCSNH$_2$,

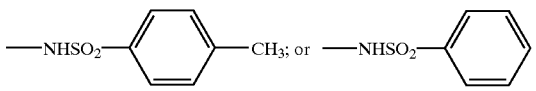

R26 is hydrogen, alkyl with from 1 to 6 carbon atoms, benzyl, or allyl;

R27 and R28 are independently hydrogen, alkyl with from 1 to 5 carbon atoms, or phenyl;

R29 and R30 are independently alkyl of 1–4 carbon atoms or taken together are —(CH2)q—;

R31 is H, alkyl or 1 to 4 carbon atoms, —CH2CH=CH2 or —CH2C6H4R32;

X is a carbon—carbon single bond,

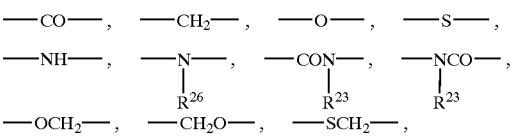

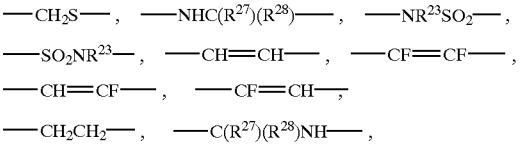

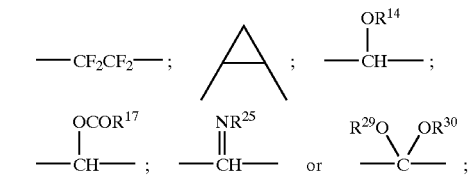

Y is O or S;

Z is O, NR11 or S;

m is 1 to 5;

n is 1 to 10;

p is 0 to 3;

q is 2 to 3;

r is 0 to 2;

s is 0 to 5;

t is 0 or 1;

and pharmaceutically acceptable salts of these compounds;

provided that:

(1) the R1 group is not in the ortho position;

(2) when R1 is

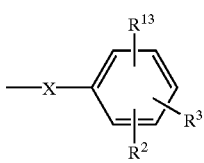

and X is a single bond, and R13 is CO2H, or

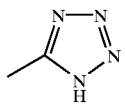

then R13 must be in the ortho or meta position; or when R1 and X are as above and R13 is NHSO2CF3 or NHSO2CH3, R13 must-be ortho, (3) when R1 is

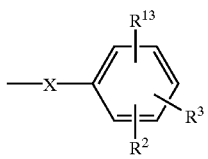

and X is other than a single bond, then R13 must be ortho except when X=NR23CO and R13 is NHSO2CF3 or NHSO2CH3 then R13 must be ortho, or meta;

(4) when R1 is 4-CO2H or a salt thereof, R6 cannot be S-alkyl;

(5) when R1 is 4-CO2H or a salt thereof, the substituent on the 4-position of the imidazole cannot be CI-120H, CH2OCOCH3, or CH2CO2H;

(6) when R1 is

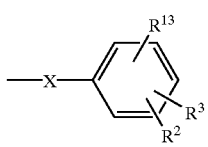

X is —OCH2—, and R13 is 2-CO2H, and R7 is H then R6 is not C2H5S;

(7) when R1 is

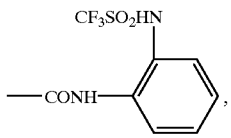

and R6 is n-hexyl then R7 and R8 are not both hydrogen;

(8) when R1 is

R6 is not methoxybenzyl;

(9) the R6 group is not

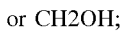

or CH2OH;

(10) when r=0, R1 is

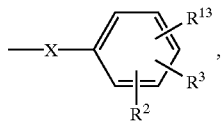

X is

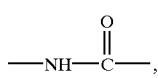

R13 is 2-NHSO2CF3, and R6 is n-propyl, then R7 and R8 are not —CO2CH3;

(11) when r=0, R1 is:

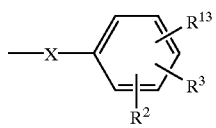

X is

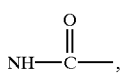

R13 is 2-COOH, and R6 is n-propyl, then R7 and R8 are not CO2CH3;

(12) when r=1, R¹ is:

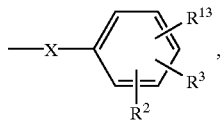

X is a single bond, R⁷ is Cl, and R⁸ is —CHO, then R¹³ is not 3-(tetrazol-5-yl);

(13) when r=1, R¹ is:

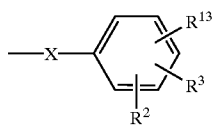

X is a single bond, R⁷ is Cl, and R⁸ is —CHO, then R¹³ is not 4-(tetrazol-5-yl).

2. The method according to claim 1 wherein the transplant patient is a renal transplant patient or a heart transplant patient.

3. The method according to claim 1 wherein the angiotensin II receptor is selected from the group consisting of 2-Butyl-4-chloro-1-[(2'-(1H-tetrazol-5-yl)biphenyl-4-yl)
methyl]-5-(hydroxymethyl)imidazole;

2-Butyl-4-chloro-1-[(2'-carboxybiphenyl-4-yl)methyl]-5-
(hydroxymethyl)imidazole;

2-Butyl-4-chloro-1-[(2'-carboxybiphenyl-4-yl)methyl]-5-
[(methoxy-carbonyl)aminomethyl]imidazole;

2-Butyl-4-chloro-1-[(2-carboxybiphenyl-4-yl)methyl]-5-
[(propoxycarbonyl)aminomethyl]imidazole;

2-Butyl-4-chloro-1-[(2'-carboxybiphenyl-4-yl)methyl]
imidazole-5-carboxaldehyde;

2-Butyl-1-[(2'-carboxybiphenyl-4-yl)methyl]-imidazole-
5-carboxy-aldehyde 2-(1E-Butenyl)-4-chloro-1-[(2'-carboxybiphenyl-4-yl)
methyl]-5-(hydroxymethyl)imidazole;

2-(1E-Butenyl)-4-chloro-1-[(2'-carboiybiphenyl-4-yl)
methyl]-imidazole-6-carboxaldehyde;

2-Propyl-4-chloro-1-[(2'-(1H-tetrazol-5-yl)biphenyl-4-yl)
methyl]-5-(hydroxymethyl)imidazole;

2-Propyl-4-chloro-1[(2'-(1H-tetrazol-5-yl)biphenyl-4-yl)
methyl]-imidazole-5-carboxaldehyde;

2-Butyl-4-chloro-1-[(2'-(1H-tetrazol-5-yl)biphenyl-4-yl)
methyl]-imidazole-5-carboxaldehyde;

2-(1E-Butenyl)-4-chloro-1-[(2'-(1H-tetrazol-5-yl)
biphenyl-4-yl)methyl]-5-hydroxymethyl)imidazole;

2(1E-Butenyl)-4-chloro-1-[(2'-(1H-tetrazol-5-yl)
biphenyl-4-yl)methyl]imidazole-5-carboxaldehyde;

2-Butyl-4-chloro-1-[(2'-(1H-tetrazol-5-yl)-biphenyl-4-yl)
methyl]-imidazole-5-carboxylic acid;

2-Propyl-4-chloro-1-[(2'-(1H-totrazol-5-yl)-biphenyl-4-
yl)methyl]-imidazole-5-carboxylic acid;

2-Propyl-4-trifluoromethyl-1-[(2'-(1H-tetrazol-5-yl)
biphenyl-4-yl)methyl]imidazole-5-carboxylic acid;

2-Propyl-4-trifluoromethyl-1-[(2'-(1H-1-tetrazol-5-yl)
biphenyl-4-yl)methyl]-5-(hydroxylmethyl)imidazole;

2-Butyl-4-trifluoromethyl-1-[(2'-(1H-tetrazol-5-yl)
biphenyl-4-yl)methyl]imidazole-5-carboxylic acid;

2-Propyl-4-trifluoromethyl-1-[(2'-(carboxybiphenyl-4-yl)
methyl]-imidazole-5-carboxaldehyde;

2-Propyl-4-pentafluoroethyl-1-[(2'-(1H-tetrazol-5-yl)
biphenyl-4-yl)methyl]-5-(hydroxymethyl)imidazole;

2-Propyl-1-[(2-(1H-tetrazol-5-yl)biphenyl-4-yl)methyl]
imidazole-4,5,-dicarboxylic acid;

2-Propyl-4-pentafluoroethyl-1-[(2'-(1H-tetrazol-5-yl)
biphenyl-4-yl)methyl]imidazole-5-carboxylic acid;

2-Propyl-4-pentafluoroethyl-[2'-1H-tetrazol-5-yl)
biphenyl-4-yl)menthyl]imidazole-5-carboxaldehyde;
and or a pharmaceutically acceptable salt thereof.

4. The method according to claim 1 wherein the angiotensin II receptor antagonist compound is selected from the group consisting of:

2-butyl-4-chloro-1-[(2'-tetrazol-5-yl) biphenyl-4-
ylmethyl-[5-(hydroxy-methyl]imidazole; and 2-butyl-4-chloro-1-[(2'-tetrazol-5-yl) biphenyl-4-
ylmethyl-[5-(hydroxy-methyl]imidazole-5-carboxylic
acid and pharmaceutically acceptable salts thereof.

5. A method for treating and preventing chromic rejection in renal transplant patients comprising administering to said patients a therapeutically effective amount of an angiotensin II receptor antagonist compound of formula I:

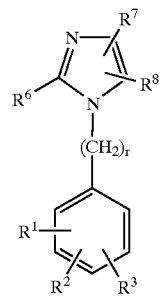

wherein:

$R^1$ is:

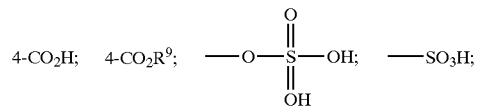

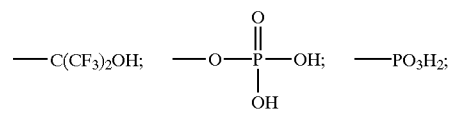

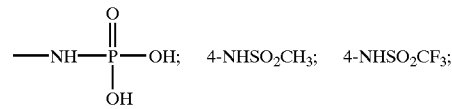

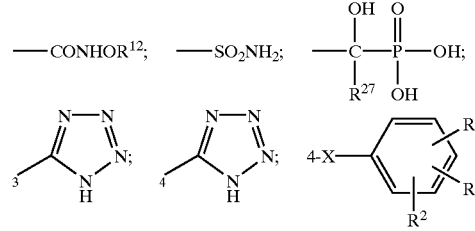

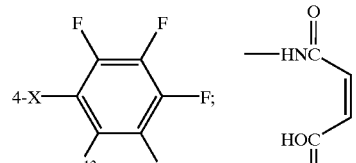

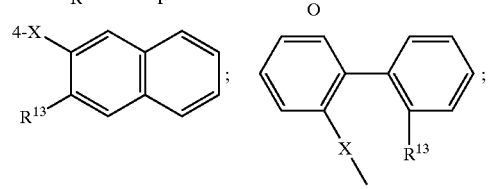

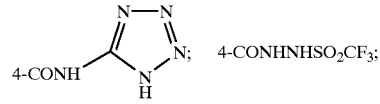

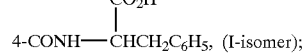

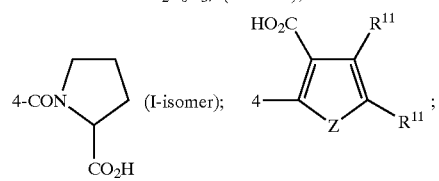

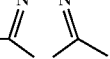

R² is H; Cl; Br; I; F; NO₂; CN; alkyl of 1 to 4 carbon atoms, acyloxy of 1 to 4 carbon atoms; alkoxy of 1 to 4 carbon atoms; CO₂H; CO₂R⁹; HNSO₂CH₃; NHSO₂CF₃; CONHOR¹²; SO₂NH₂;

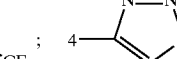

aryl; or furyl;

R³ is H; Cl, Br, I or F; alkyl of 1 to 4 carbon atoms or alkoxy of 1 to 4 carbon atoms;

R⁴ is CN, NO₂ or CO₂R¹¹,

R⁵ is H, alkyl of 1 to 6 carbon atoms, cycloalkyl of 3 to 6 carbon atoms alkenyl or alkynyl of 2 to 4 carbon atoms;

R⁶ is alkyl of 2 to 10 carbon atoms, alkenyl or alkynyl of 3 to 10 carbon atoms or the same groups substituted with F or CO₂R¹⁴; cycloalkyl of 3 to 8 carbon atoms, cycloalkylalkyl, of 4 to 10 carbon atoms; cycloalkylalkenyl or cycloalkylalkynyl 5 to 10 carbon atoms; (CH₂)sZ(CH₂)MR⁵ optionally substituted with F or CO₂R¹⁴; benzyl substituted on the phenyl ring with 1 or 2 halogens, alkoxy of 1 to 4 carbon atoms, alkyl of 1 to 4 carbon atoms or nitro;

R7 is H, F, Cl, Br, 1, NO₂, C$_v$F$_{2v+1}$, where v=1–6, C₆F₅; CN;

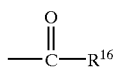

straight or branched alkyl of 1 to 6 carbon atoms; phenyl or phanylalkyl, where alkyl is 1 to 3 carbon atoms; or substituted phenyl or substituted phenylalkyl, where alkyl is 1 to 3 carbon atoms, substituted with one or two substituents selected from alkyl of 1 to 4 carbon atoms, F, Cl, Br, OH, OCH₃, CF₃, and COOR, where R is H, alkyl of 1 to 4 carbon atoms, or phenyl;

R⁸ is H, CN, alkyl of 1 to 10 carbon atoms, alkenyl of 3 to 10 carbon atoms, or the same groups substituted with F; phenylalkenyl wherein the aliphatic portion is 2 to 6 carbon atoms; —(CH₂)m-imidazol-1-yl; —(CH₂)$_m$-1,2,3-triazolyl optionally substituted with one or two group selected from CO₂CH₃ or alkyl of 1 to 4 carbon atoms; —(CH₂)$_s$ tetrazolyl;

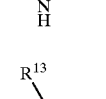

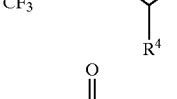

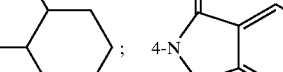

R⁹ is: 

R¹⁰ is alkyl of 1 to 6 carbon atoms or perfluoroalkyl of 1 to 6 carbon atoms, 1-adaman 1-naphthyl, 1-(1-naphthyl)ethyl, or (CH₂)$_p$C₆H₅;

R¹¹ is H, alkyl of 1 to 6 carbon atoms, cycloalkyl of 3 to 6 carbon atoms, phenyl or benzyl;

R¹² is H, methyl or benzyl;

R13 is —CO₂H; —CO₂R⁹; —CH₂CO₂H,

-continued

—CH₂CO₂R⁹;  —O—S(=O)(OH)—OH;  —O—P(=O)(OH)—OH;

—SO₃H;  —NHP(=O)(OH)—OH;  —C(OH)(R²⁷)—P(=O)(OH)—OH;

—PO₃H₂;  —C(CF₃)₂OH;  —NHSO₂CH₃;

—NHSO₂CF₃;  —NHCOCF₃;  —CONHOR¹²;

—SO₂NH₂;  [methyl-tetrazole N-R³¹];  —CH₂-[tetrazole NH];

—CONH-[tetrazole NH];  —CONHNHSO₂CF₃;

[methyl-triazole-CF₃]; or [methyl-R⁴-triazole-NH];

R¹⁴ is H, alkyl or perfluoroalkyl of 1 to 8 carbon atoms, cycloalkyl of 3 to 6 carbon atoms, phenyl or benzyl;
R¹⁵ is H, alkyl of 1 to 6 carbon atoms, cycloalkyl of 3 to 6 carbon atoms, phenyl, benzyl, acyl of 1 to 4 carbon atoms, phenacyl;
R¹⁶ is H, alkyl of 1 to 6 carbon atoms, cycloalkyl of 3 to 6 carbon atoms, (CH₂)$_p$C₆H₅, OR¹⁷, or NR¹⁸R¹⁹;
R¹⁷ is H, alkyl of 1 to 6 carbon atoms, cycloalkyl of 3 to 6 carbon atoms, phenyl or benzyl;
R¹⁸ and R¹⁹ independently are H, alkyl of 1 to 4 carbon atoms, phenyl, benzyl, →-methylbenzyl, or taken together with the nitrogen form a ring, of the formula

—N[(CH₂)ₜ]Q,

Q is NR20, O or CH2;
R20 is H, alkyl of 1–4 carbon atoms, or phenyl;
R21 is alkyl of 1 to 6 carbon atoms, —NR22R239 or

—CHCH2CO2CH3;
   |
   NH₂

R22 and R23 independently are H, alkyl of 1 to 6 carbon atoms, benzyl, or are taken together as (C112)u where u is 3–6;
R²⁴ is H, CH₃ or —C₆H₅;
R²⁵ is NR²⁷R²⁸, OR²⁸, NHCONH₂, NHCSNH₂, —NHSO₂-[phenyl]-CH₃; or —NHSO₂-[phenyl];

R26 is hydrogen, alkyl with from 1 to 6 carbon atoms, benzyl, or allyl;
R27 and R28 are independently hydrogen, alkyl with from 1 to 5 carbon atoms, or phenyl;

R29 and R30 are independently alkyl of 1–4 carbon atoms or taken together are —(CH2)q—;
R31 is H, alkyl or 1 to 4 carbon atoms, —CH2CH=CH2 or —CH2C6H4R32;
X is a carbon—carbon single bond,

—CO—, —CH₂—, —O—, —S—,

—NH—, —N(R²⁶)—, —CON(R²³)—, —NCO(R²³)—,

—OCH₂—, —CH₂O—, —SCH₂—,

—CH₂S—, —NHC(R²⁷)(R²⁸)—, —NR²³SO₂—,

—SO₂NR²³—, —CH=CH—, —CF=CF—,

—CH=CF—, —CF=CH—,

—CH₂CH₂—, —C(R²⁷)(R²⁸)NH—,

—CF₂CF₂—;  [cyclopropyl]; —CH(OR¹⁴)—;

—CH(OCOR¹⁷)—; —CH(=NR²⁵)— or —C(R²⁹O)(OR³⁰)—;

Y is O or S;
Z is O, NR11 or S;
m is 1 to 5;
n is 1 to 10;
p is 0 to 3;
q is 2 to 3;
r is 0 to 2;
s is 0 to 5;
t is 0 or 1;

and pharmaceutically acceptable salts of these compounds; provided that:

(1) the R1 group is not in the ortho position;
(2) when R1 is

—X-[phenyl with R¹³, R², R³]

X is a single bond, and R13 is CO2H, or

[methyl-tetrazole NH]

then R13 must be in the ortho or meta position; or when R1 and X are as above and R13 is NHSO2CF3 or NHSO2CH3, R13 must-be ortho, (3) when R1 is

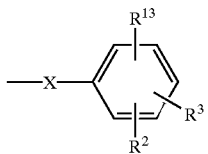

and X is other than a single bond, then R13 must be ortho except when X=NR23CO and R13 is NHSO2CF3 or NHSO2CH3 then R13 must b e ortho, or meta;

(4) when R1 is 4-CO2H or a salt thereof, R6 cannot be S-alkyl;

(5) when R1 is 4-CO2H or a salt thereof, the substituent on the 4-position of the imidazole cannot be CI-12OH, CH2OCOCH3, or CH2CO2H;

(6) when R1 is

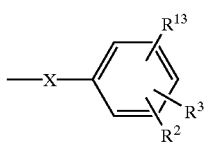

X is —OCH2—, and R13 is 2-CO2H, and R7 is H then R6 is not C2H5S;

(7) when R1 is

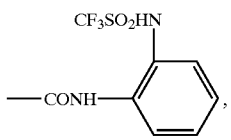

and R6 is n-hexyl then R7 and R8 are not both hydrogen;

(8) when R1 is

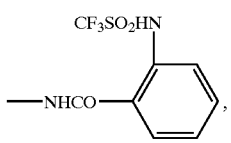

R6 is not methoxybenzyl;

(9) the R6 group is not

or CH2OH;

(10) when r=0, R1 is

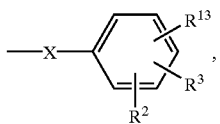

X is

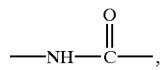

R13 is 2-NHSO2CF3, and R6 is n-propyl, then R7 and R8 are not —CO2CH3;

(11) when r=0, R1 is:

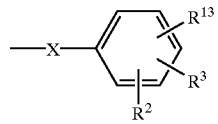

X is

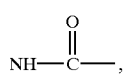

R13 is 2-COOH, and R6 is n-propyl, then R7 and R8 are not CO2CH3;

(12) when r=1, $R^1$ is:

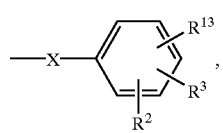

X is a single bond, $R^7$ is Cl, and $R^8$ is —CHO, then $R^{13}$ is not 3-(tetrazol-5-yl);

(13) when r=1, $R^1$ is:

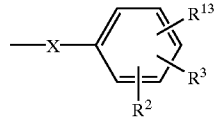

X is a single bond, $R^7$ is Cl, and $R^8$ is —CHO, then $R^{13}$ is not 4-(tetrazol-5-yl).

6. The method according to claim 5 wherein the angiotensin II receptor is selected from the group consisting of 2-Butyl-4-chloro-1-[(2'-(1H-tetrazol-5-yl)biphenyl-4-yl) methyl]-5-(hydroxymethyl)imidazole;

2-Butyl-4-chloro-1-[(2'-carboxybiphenyl-4-yl)methyl]-5-(hydroxymethyl)imidazole;

2-Butyl-4-chloro-1-[(2'-carboxybiphenyl-4-yl)methyl]-5-[(methoxy-. carbonyl)aminomethyl]imidazole;

2-Butyl-4-chloro-1-[(2'-carboxybiphenyl-4-yl)methyl]-5-[-(propoxycarbonyl)aminomethyl]imidazole;

2-Butyl-4-chloro-1-[(2'-carboxybiphenyl-4-y)methyl] imidazole-5-carboxaldehyde;

2-Butyl-1-[(2'-carboxybiphenyl-4-yl)methyl]-imidazole-5-carboxy-aldehyde;

2-(1E-Butenyl)-4-chloro-1-[(2'-carboxybiphenyl-4-yl) methyl]-5-(hydroxymethyl)imidazole;

2-(1E-Butenyl)-4-chloro-1-[(2'-carboiybiphenyl-4-yl) methyl]-imidazole-6-carboxaldehyde;

2-Propyl-4-chloro-1-[(2'-(1H-tetrazol-5-yl)biphenyl-4-yl (hydroxymethyl)imidazole;

2-Propyl-4-chloro-1[(2'-(1H-tetrazol-5-yl)biphenyl-4-yl)
methyl]-imidazole-5-carboxaldehyde;

2-Butyl-4-chloro-1-[2'-(1H-tetrazol-5-yl)biphenyl-4-yl)
methyl]-imidazole-5-carboxaldehyde;

2-(1E-Butenyl)-4-chloro-1-[(2'-(1H-tetrazol-5-yl)
bipheny 1-4-yl)methyl]-5-hydroxymethyl)imidazole;

2(1E-Butenyl)-4-chloro-1-[(2'-(1H-tetrazol-5-yl)biphenyl
-4-yl)methyl]imidazole-5-carboxaldehyde;

2-Butyl-4-chloro-1-[(2'-(1H-tetrazol-5-yl)-biphenyl-4-yl)
methyl]-imidazole-5-carboxylic acid;

2-Propyl-4-chloro-1-[(2'-(1H-totrazol-5-yl)-biphenyl-4-
yl)methyl]-imidazole-5-carboxylic acid;

2-Propyl-4-trifluoromethyl-1-[(2'-(1H-tetrazol-5-yl)
biphenyl-4-yl)methyl]imidazole-5-carboxylic acid;

2-Propyl-4-trifluoromethyl-1-[(2'-(1H-1-tetrazol-5-yl)
biphenyl-4-yl)methyl]-5-(hydroxylmethyl)imidazole;

2-Butyl-4-trifluoromethyl-1-[(2'-(1H-tetrazol-5-yl)
biphenyl-4-yl)methyl]imidazole-5-carboxylic acid;

2-Propyl-4-trifluoromethyl-1-[(2'-(carboxybiphenyl-4-yl)
methyl]-imidazole-5-carboxaldehyde;

2-Propyl-4-pentafluoroethyl-1-[(2'-(1H-tetrazol-5-yl)
biphenyl-4-yl)methyl]-5-(hydroxymethyl)imidazole;

2-Propyl-1-[(2-(1H-tetrazol-5-yl)biphenyl-4-yl)methyl]
imidazole-4,5,-dicarboxylic acid;

2-Propyl-4-pentafluoroethyl-1-[(2'-(1H-tetrazol-5-yl)
biphenyl-4-yl)methyl]imidazole-5-carboxylic acid;

2-Propyl-4-pentafluoroethyl-[2'-1H-tetrazol-5-yl)
biphenyl-4-yl)menthyl]imidazole-5-carboxaldehyde;
and or a pharmaceutically acceptable salt thereof.

7. The method according to claim 5 wherein the angiotensin II receptor antagonist compound is selected from the group consisting of:

2-butyl-4-chloro-1-[(2'-tetrazol-5-yl) biphenyl-4-ylmethyl-[5-(hydroxy-methyl]imidazole; and 2-butyl-4-chloro-1-[(2'-tetrazol-5-yl) biphenyl-4-ylmethyl-[5-(hydroxy-methyl]imidazole-5-carboxylic acid and pharmaceutically acceptable salts thereof.

8. A method for reducing proteinuria in renal transplant patients comprising administering to said patients a therapeutically effective amount of an angiotensin II receptor antagonist compound of formula I:

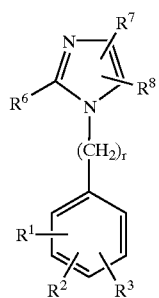

wherein:

$R^1$ is:

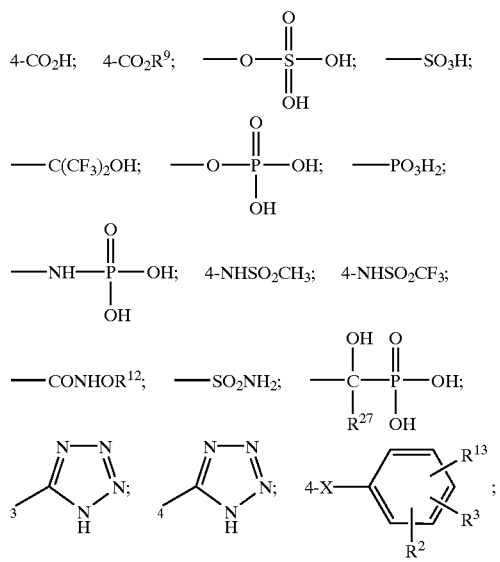

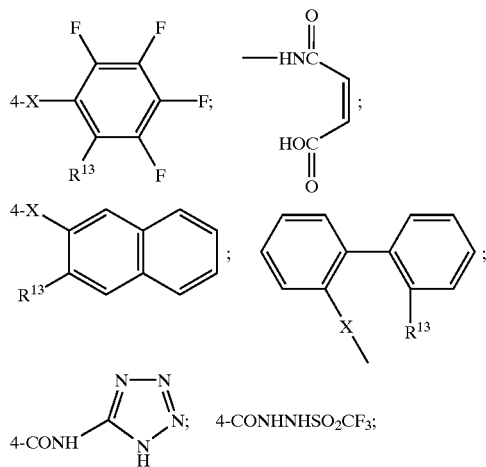

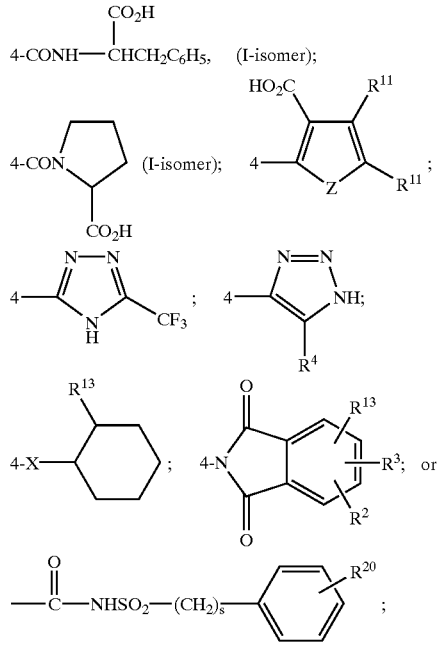

$R^2$ is H; Cl; Br; I; F; $NO_2$; CN; alkyl of 1 to 4 carbon atoms; acyloxy of 1 to 4 carbon atoms; alkoxy of 1 to 4 carbon atoms; $CO_2H$; $CO_2R^9$; $HNSO_2CH_3$; $NHSO_2CF_3$; $CONHOR^{12}$; $SO_2NH_2$;

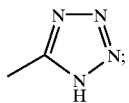

aryl; or furyl;

$R^3$ is H; Cl, Br, I or F; alkyl of 1 to 4 carbon atoms or alkoxy of 1 to 4 carbon atoms;

$R^4$ is CN, $NO_2$ or $CO_2R^{11}$, $R^5$ is H, alkyl of 1 to 6 carbon atoms, cycloalkyl of 3 to 6 carbon atoms alkenyl or alkynyl of 2 to 4 carbon atoms;

$R^6$ is alkyl of 2 to 10 carbon atoms, alkenyl or alkynyl of 3 to 10 carbon atoms or the same groups substituted with F or $CO_2R^{14}$; cycloalkyl of 3 to 8 carbon atoms, cycloalkylalkyl, of 4 to 10 carbon atoms; cycloalkylalkenyl or cycloalkylalkynyl 5 to 10 carbon atoms; $(CH_2)sZ(CH_2)MR^5$ optionally substituted with F or $CO_2R^{14}$; benzyl substituted on the phenyl ring with 1 or 2 halogens, alkoxy of 1 to 4 carbon atoms, alkyl of 1 to 4 carbon atoms or nitro;

R7 is H, F, Cl, Br, 1, $NO_2$, $C_vF_{2v}+1$, where v=1–6, $C_6F_5$; CN;

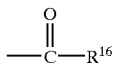

straight or branched alkyl of 1 to 6 carbon atoms; phenyl or phanylalkyl, where alkyl is 1 to 3 carbon atoms; or substituted phenyl or substituted phenylalkyl, where alkyl is 1 to 3 carbon atoms, substituted with one or two substituents selected from alkyl of 1 to 4 carbon atoms, F, Cl, Br, OH, $OCH_3$, $CF_3$, and COOR, where R is H, alkyl of 1 to 4 carbon atoms, or phenyl;

R8 is H, CN, alkyl of 1 to 10 carbon atoms, alkenyl of 3 to 10 carbon atoms, or the same groups substituted with F; phenylalkenyl wherein the aliphatic portion is 2 to 6 carbon atoms; —$(CH_2)$m-imidazol-1-yl; —$(CH_2)_m$-1,2,3-triazolyl optionally substituted with one or two group selected from $CO_2CH_3$ or alkyl of 1 to 4 carbon atoms; —$(CH_2)_s$ tetrazolyl;

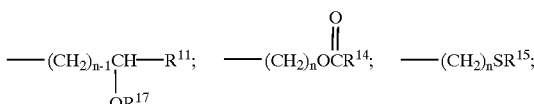

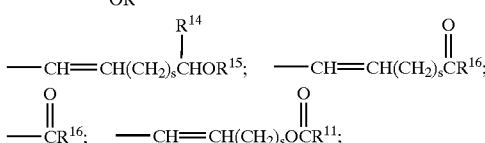

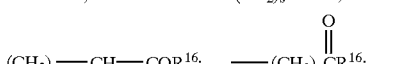

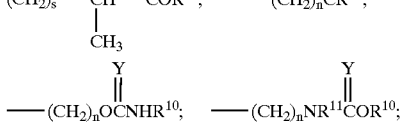

-continued

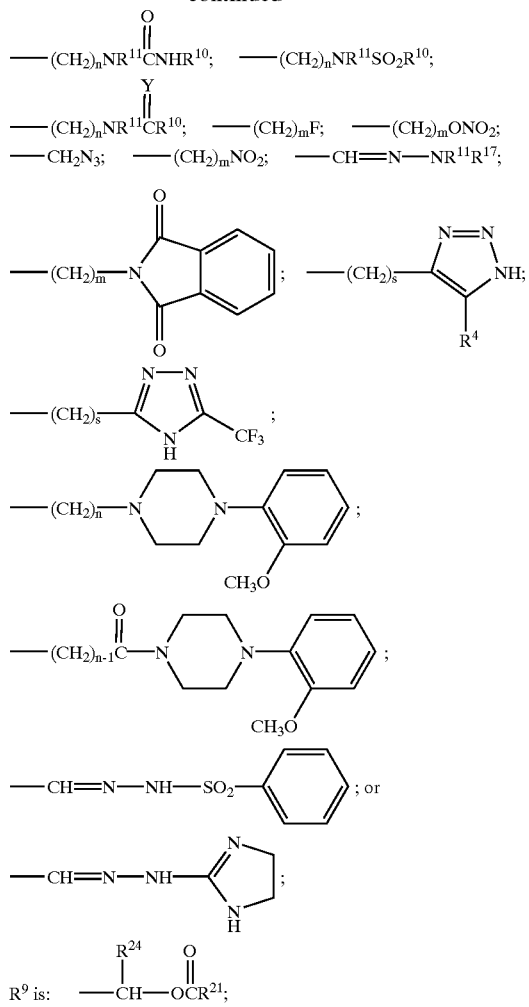

$R^9$ is: —$\overset{R^{24}}{\underset{|}{CH}}$—$O\overset{O}{\underset{\|}{C}}R^{21}$;

R10 is alkyl of 1 to 6 carbon atoms or perfluoroalkyl of 1 to 6 carbon atoms, 1-adaman 1-naphthyl, 1-(1-naphthyl)ethyl, or $(CH_2)_pC_6H_5$;

$R^{11}$ is H, alkyl of 1 to 6 carbon atoms, cycloalkyl of 3 to 6 carbon atoms, phenyl or benzyl;

$R^{12}$ is H, methyl or benzyl;

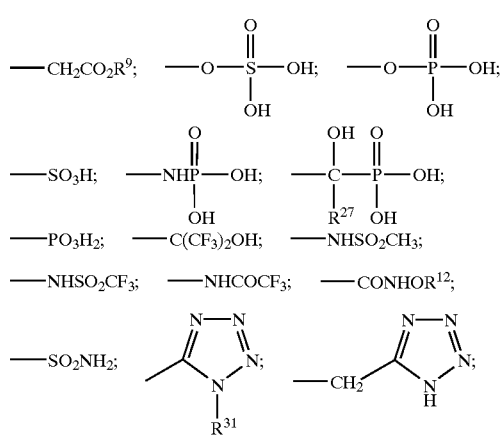

—CONH— 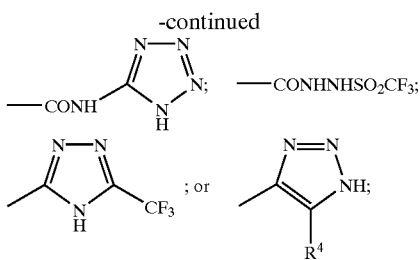 —CONHNHSO2CF3;

R14 is H, alkyl or perfluoroalkyl of 1 to 8 carbon atoms, cycloalkyl of 3 to 6 carbon atoms, phenyl or benzyl;
R15 is H, alkyl of 1 to 6 carbon atoms, cycloalkyl of 3 to 6 carbon atoms, phenyl, benzyl, acyl of 1 to 4 carbon atoms, phenacyl;
R16 is H, alkyl of 1 to 6 carbon atoms, cycloalkyl of 3 to 6 carbon atoms, $(CH_2)_p C_6 H_5$, $OR^{17}$, or $NR^{18}R^{19}$;
R17 is H, alkyl of 1 to 6 carbon atoms, cycloalkyl of 3 to 6 carbon atoms, phenyl or benzyl;
R18 and R19 independently are H, alkyl of 1 to 4 carbon atoms, phenyl, benzyl, →-methylbenzyl, or taken together with the nitrogen form a ring, of the formula

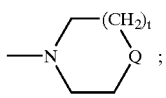

Q is NR20, O or CH2;
R20 is H, alkyl of 1–4 carbon atoms, or phenyl;
R21 is alkyl of 1 to 6 carbon atoms, —NR22R239 or

—CHCH2CO2CH3;
  NH2

R22 and R23 independently are H, alkyl of 1 to 6 carbon atoms, benzyl:, or are taken together as (Cl12)u where u is 3–6;
R24 is H, CH3 or —C6H5;
R25 is $NR^{27}R^{28}$, $OR^{28}$, NHCONH2, NHCSNH2,

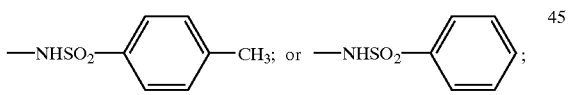

R26 is hydrogen, alkyl with from 1 to 6 carbon atoms, benzyl, or allyl;
R27 and R28 are independently hydrogen, alkyl with from 1 to 5 carbon atoms, or phenyl;
R29 and R30 are independently alkyl of 1–4 carbon atoms or taken together are —(CH2)q—;
R31 is H, alkyl or 1 to 4 carbon atoms, —CH2CH═CH2 or —CH2C6H4R32;
X is a carbon—carbon single bond, —CO—, —CH2—, —O—, —S—,
—NH—, —N(R26)—, —CON(R23)—, —NCO(R23)—,
—OCH2—, —CH2O—, —SCH2—,
—CH2S—, —NHC(R27)(R28)—, —NR23SO2—, —SO2NR23—, —CH═CH—, —CF═CF—,
—CH═CF—, —CF═CH—,
—CH2CH2—, —C(R27)(R28)NH—,
—CF2CF2—; 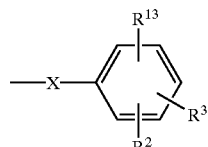 ; —CH(OR14)—;
—CH(OCOR17)—; —CH(NR25)— or 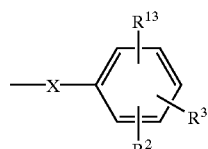 ;

Y is O or S;
Z is O, NR11 or S;
m is 1 to 5;
n is 1 to 10;
p is 0 to 3;
q is 2 to 3;
r is 0 to 2;
s is 0 to 5;
t is 0 or 1;

and pharmaceutically acceptable salts of these compounds; provided that:

(1) the R1 group is not in the ortho position;
(2) when R1 is

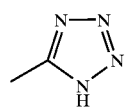

X is a single bond, and R13 is CO2H, or then R13 must be in the ortho or meta position; or when R1 and X are as above and R13 is NHSO2CF3 or NHSO2CH3, R13 must-be ortho, (3) when R1 is and X is other than a single bond, then R13 must be ortho except when X═NR23CO and R13 is NHSO2CF3 or NHSO2CH3 then R13 must be ortho, or meta;

(4) when R1 is 4-CO2H or a salt thereof, R6 cannot be S-alkyl;
(5) when R1 is 4-CO2H or a salt thereof, the substituent on the 4-position of the imidazole cannot be Cl-120H, CH2OCOCH3, or CH2CO2H;

(6) when R1 is

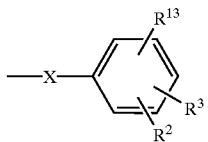

X is —OCH2—, and R13 is 2-CO2H, and R7 is H then R6 is not C2H5S;

(7) when R1 is

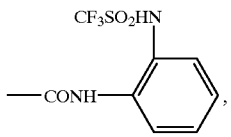

and R6 is n-hexyl then R7 and R8 are not both hydrogen;

(8) when R1 is

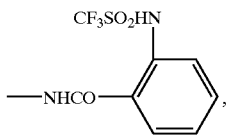

R6 is not methoxybenzyl;

(9) the R6 group is not

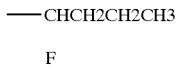

or CH2OH;

(10) when r=0, R1 is

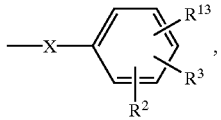

X is

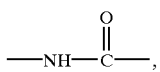

R13 is 2-NHSO2CF3, and R6 is n-propyl, then R7 and R8 are not —CO2CH3;

(11) when r=0, R1 is:

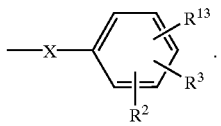

X is

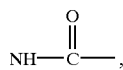

R13 is 2-COOH, and R6 is n-propyl, then R7 and R8 are not CO2CH3;

(12) when r=1, $R^1$ is:

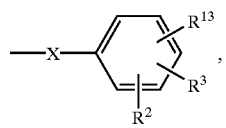

X is a single bond, $R^7$ is Cl, and $R^8$ is —CHO, then $R^{13}$ is not 3-(tetrazol-5-yl);

(13) when r=1, $R^1$ is:

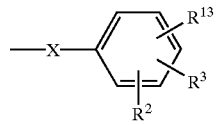

X is a single bond, $R^7$ is Cl, and $R^8$ is —CHO, then $R^{13}$ is not 4-(tetrazol-5-yl).

9. The method according to claim 8 wherein the angiotensin II receptor antagonist compound is selected from the group consisting of:

2-Butyl-4-chloro-1-[(2'-(1H-tetrazol-5-yl)biphenyl-4-yl) methyl]-5-(hydroxymethyl)imidazole;

2-Butyl-4-chloro-1-[(2'-carboxybiphenyl-4-yl)methyl]-5-(hydroxymethyl)imidazole;

2-Butyl-4-chloro-1-[(2'-carboxybiphenyl-4-yl)methyl]-5-[(methoxy-. carbonyl)aminomethyl]imidazole;

2-Butyl-4-chloro-1-[(2'-carboxybiphenyl-4-yl)methyl]-5-[(propoxycarbonyl)aminomethyl]imidazole;

2-Butyl-4-chloro-1-[(2'-carboxybiphenyl-4-yl)methyl] imidazole-5-carboxaldehyde;

2-Butyl-1-[(2'-carboxybiphenyl-4-yl)methyl]-imidazole-5-carboxy-aldehyde;

2-(1E-Butenyl)-4-chloro-1-C(2'-carboxybiphenyl-4-yl) methyl]-5-(hydroxymethyl)imidazole;

2-(1E-Butenyl)-4-chloro-1-[(2'-carboiybiphenyl-4-yl) methyl]-imidazole-6-carboxaldehyde;

2-Propyl-4-chloro-1-[(2'-(1H-tetrazol-5-yl) biphenyl-4-yl)methyl]-5-(hydroxymethyl)imidazole;

2-Propyl-4-chloro-1[(2'-(1H-tetrazol-5-yl)biphenyl-4-yl) methyl]-imidazole-5-carboxaldehyde;

2-Butyl-4-chloro-1-[2'-(1H-tetrazol-5-yl)biphenyl-4-yl) methyl]-imidazole-5-carboxaldehyde;

2-(1E-Butenyl)-4-chloro-1-[(2'-(1H-tetrazol-5-yl) bipheny 1-4-yl)methyl]-5-hydroxymethyl)imidazole;

2-(E-Butenyl)-4-chloro-1-[(2'-(1H-tetrazol-5-yl)biphenyl -4-yl)methyl]imidazole-5-carboxaldehyde;

2-Butyl-4-chloro-1-[(2'-(1H-tetrazol-5-yl)-biphenyl-4-yl) methyl]-imidazole-5-carboxylic acid;

2-Propyl-4-chloro-1-[(2'-(1H-totrazol-5-yl)-biphenyl-4-yl)methyl]-imidazole-5-carboxylic acid;

2-Propyl-4-trifluoromethyl-1-[(2'-(1H-tetrazol-5-yl) biphenyl-4-yl)methyl]imidazole-5-carboxylic acid;

2-Propyl-4-trifluoromethyl-1-[(2'-(1H-1-tetrazol-5-yl) biphenyl-4-yl)methyl]-5-(hydroxylmethyl)imidazole;

2-Butyl-4-trifluoromethyl-1-[(2'-(1H-tetrazol-5-yl) biphenyl-4-yl)methyl]imidazole-5-carboxylic acid;

2-Propyl-4-trifluoromethyl-1-[(2'-(carboxybiphenyl-4-yl) methyl]-imidazole-5-carboxaldehyde;

2-Propyl-4-pentafluoroethyl-1-[(2'-(1H-tetrazol-5-yl) biphenyl-4-yl)methyl]-5-(hydroxymethyl)imidazole;

2-Propyl-1-[(2-(1H-tetrazol-5-yl)biphenyl-4-yl)methyl] imidazole-4,5,-dicarboxylic acid;

2-Propyl-4-pentafluoroethyl-1-[(2'-(1H-tetrazol-5-yl) biphenyl-4-yl)methyl]imidazole-5-carboxylic acid;

2-Propyl-4-pentafluoroethyl-[2'-1H-tetrazol-5-yl) biphenyl-4-yl)menthyl]imidazole-5-carboxaldehyde; and or a pharmaceutically acceptable salt thereof.

10. The method according to claim 8 wherein the angiotensin II receptor antagonist compound is selected from the group consisting of:

2-butyl-4-chloro-1-[(2'-tetrazol-5-yl) biphenyl-4-ylmethyl-[5-(hydroxy-methyl]imidazole; and 2-butyl-4-chloro-1-[(2'-tetrazol-5-yl) biphenyl-4-ylmethyl-[5-(hydroxy-methyl]imidazole-5-carboxylic acid and pharmaceutically acceptable salts thereof.

11. A method for increasing the survival rate of transplant patients comprising administering to said patients a therapeutically effective amount of an angiotensin II receptor antagonist compound of formula I:

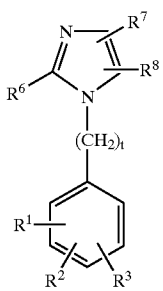

I wherein:

$R^1$ is:

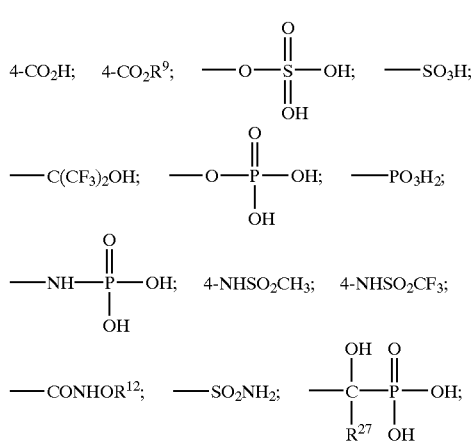

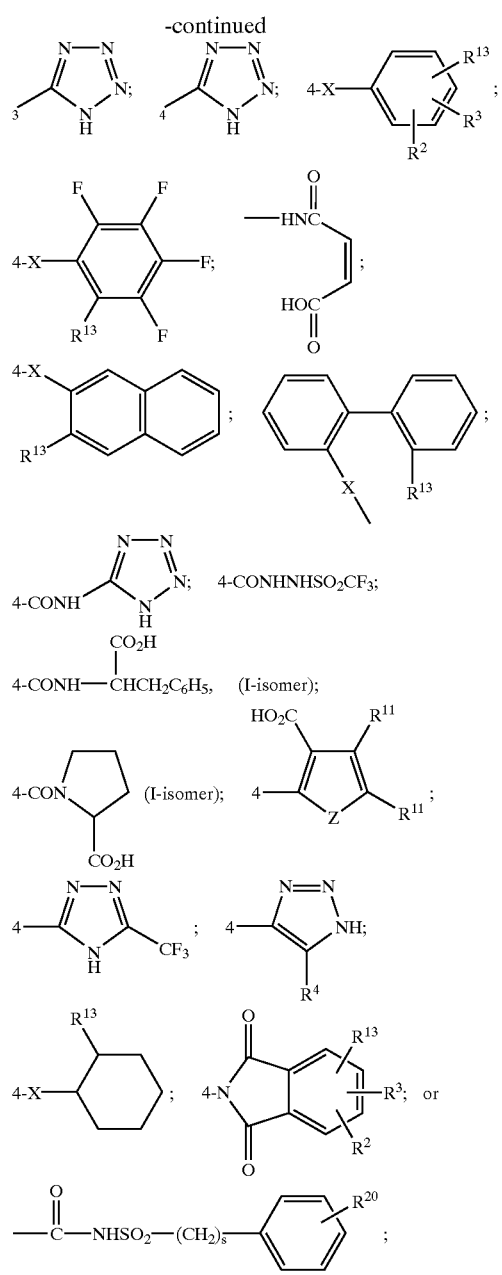

$R^2$ is H; Cl; Br; I; F; $NO_2$; CN; alkyl of 1 to 4 carbon atoms; acyloxy of 1 to 4 carbon atoms; alkoxy of 1 to 4 carbon atoms; $CO_2H$; $CO_2R^9$; $HNSO_2CH_3$; $NHSO_2CF_3$; $CONHOR^{12}$; $SO_2NH_2$;

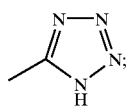

aryl; or furyl;

$R^3$ is H; Cl, Br, I or F; alkyl of 1 to 4 carbon atoms or alkoxy of 1 to 4 carbon atoms;

$R^4$ is CN, $NO_2$ or $CO_2R^{11}$, $R^5$ is H, alkyl of 1 to 6 carbon atoms, cycloalkyl of 3 to 6 carbon atoms alkenyl or alkynyl of 2 to 4 carbon atoms;

$R^6$ is alkyl of 2 to 10 carbon atoms, alkenyl or alkynyl of 3 to 10 carbon atoms or the same groups substituted with F or $CO_2R^{14}$; cycloalkyl of 3 to 8 carbon atoms, cycloalkylalkyl, of 4 to 10 carbon atoms; cycloalkylalkenyl or cycloalkylalkynyl 5 to 10 carbon atoms; $(CH_2)sZ(CH_2)MR^5$ optionally substituted with F or $CO_2R^{14}$; benzyl substituted on the phenyl ring with 1 or 2 halogens, alkoxy of 1 to 4 carbon atoms, alkyl of 1 to 4 carbon atoms or nitro;

R7 is H, F, Cl, Br, 1, $NO_2$, $C_vF_{2v}+1$, where v=1–6, $C_6F_5$; CN;

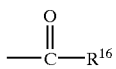

straight or branched alkyl of 1 to 6 carbon atoms; phenyl or phanylalkyl, where alkyl is 1 to 3 carbon atoms; or substituted phenyl or substituted phenylalkyl, where alkyl is 1 to 3 carbon atoms, substituted with one or two substituents selected from alkyl of 1 to 4 carbon atoms, F, Cl, Br, OH, $OCH_3$, $CF_3$, and COOR, where R is H, alkyl of 1 to 4 carbon atoms, or phenyl;

$R^8$ is H, CN, alkyl of 1 to 10 carbon atoms, alkenyl of 3 to 10 carbon atoms, or the same groups substituted with F; phenylalkenyl wherein the aliphatic portion is 2 to 6 carbon atoms; —$(CH_2)$m-imidazol-1-yl; —$(CH_2)_m$-1,2,3-triazolyl optionally substituted with one or two group selected from $CO_2CH_3$ or alkyl of 1 to 4 carbon atoms; —$(CH_2)_s$ tetrazolyl;

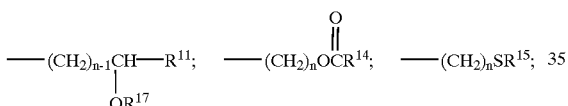

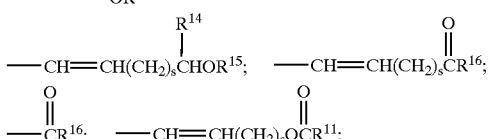

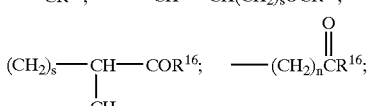

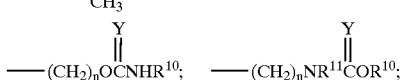

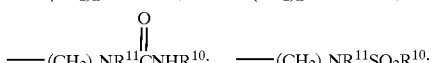

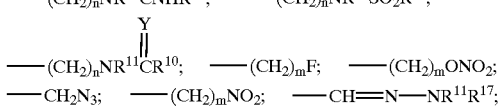

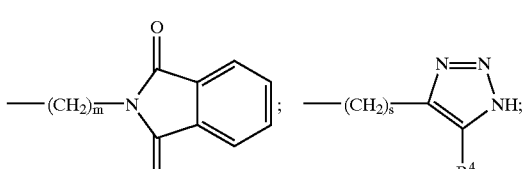

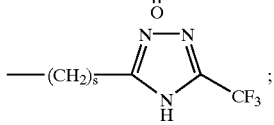

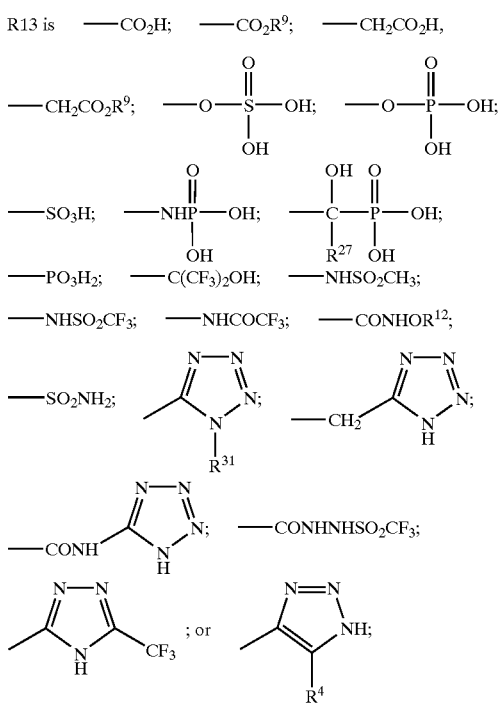

$R^{10}$ is alkyl of 1 to 6 carbon atoms or perfluoroalkyl of 1 to 6 carbon atoms, 1-adaman 1-naphthyl, 1-(1-naphthyl)ethyl, or $(CH_2)_pC_6H_5$;

$R^{11}$ is H, alkyl of 1 to 6 carbon atoms, cycloalkyl of 3 to 6 carbon atoms, phenyl or benzyl;

$R^{12}$ is H, methyl or benzyl;

$R^{14}$ is H, alkyl or perfluoroalkyl of 1 to 8 carbon atoms, cycloalkyl of 3 to 6 carbon atoms, phenyl or $R^{15}$ is H, alkyl of 1 to 6 carbon atoms, cycloalkyl of 3 to 6 carbon atoms, phenyl, benzyl, acyl of 1 to 4 carbon atoms, phenacyl;

$R^{16}$ is H, alkyl of 1 to 6 carbon atoms, cycloalkyl of 3 to 6 carbon atoms, $(CH_2)_pC_6H_5$, $OR^{17}$, or $NR^{18}R^{19}$;

$R^{17}$ is H, alkyl of 1 to 6 carbon atoms, cycloalkyl of 3 to 6 carbon atoms, phenyl or benzyl;

$R^{18}$ and $R^{19}$ independently are H, alkyl of 1 to 4 carbon atoms, phenyl, benzyl, →-methylbenzyl, or taken together with the nitrogen form a ring, of the formula

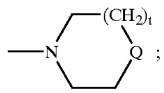

Q is NR20, O or CH2;

R20 is H, alkyl of 1–4 carbon atoms, or phenyl;

R21 is alkyl of 1 to 6 carbon atoms, —NR22R239 or —CHCH2CO2CH3; NH2

R22 and R23 independently are H, alkyl of 1 to 6 carbon atoms, benzyl, or are taken together as (C112)u where u is 3–6;

$R^{24}$ is H, $CH_3$ or —$C_6H_5$;

$R^{25}$ is $NR^{27}R^{28}$, $OR^{28}$, NHCONH$_2$, NHCSNH$_2$,

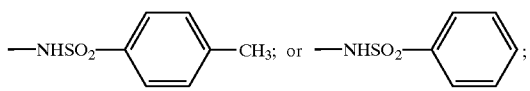

R26 is hydrogen, alkyl with from 1 to 6 carbon atoms, benzyl, or allyl;

R27 and R28 are independently hydrogen, alkyl with from 1 to 5 carbon atoms, or phenyl;

R29 and R30 are independently alkyl of 1–4 carbon atoms or taken together are —(CH2)q—;

R31 is H, alkyl or 1 to 4 carbon atoms, —CH2CH=CH2 or —CH2C6H4R32;

Y is O or S;

Z is O, NR11 or S;

m is 1 to 5;

n is 1 to 10;

p is 0 to 3;

q is 2 to 3;

r is 0 to 2;

s is 0 to 5;

t is 0 or 1;

and pharmaceutically acceptable salts of these compounds; provided that:

(1) the R1 group is not in the ortho position;

X is a carbon—carbon single bond,

—CO—, —CH2—, —O—, —S—,

—NH—, —N—, —CON—, —NCO—,
            |           |           |
            $R^{26}$    $R^{23}$    $R^{23}$

—OCH2—, —CH2O—, —SCH2—,

—CH2S—, —NHC($R^{27}$)($R^{28}$)—, —NR$^{23}$SO2—,

—SO2NR$^{23}$—, —CH=CH—, —CF=CF—,

—CH=CF—, —CF=CH—,

—CH2CH2—, —C($R^{27}$)($R^{28}$)NH—,

—CF2CF2—; 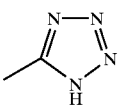 ; —CH(OR$^{14}$)—;

-continued

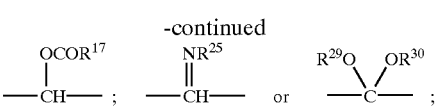

(2) when R1 is

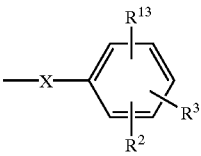

X is a single bond, and R13 is CO2H, or

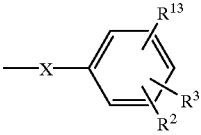

then R13 must be in the ortho or meta position; or when R1 and X are as above and R13 is NHSO2CF3 or NHSO2CH3, R13 must-be ortho, (3) when R1 is

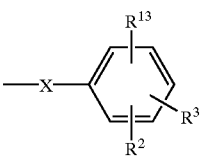

and X is other than a single bond, then R13 must be ortho except when X=NR23CO and R13 is NHSO2CF3 or NHSO2CH3 then R13 must be ortho, or meta;

(4) when R1 is 4-CO2H or a salt thereof, R6 cannot be S-alkyl;

(5) when R1 is 4-CO2H or a salt thereof, the substituent on the 4-position of the imidazole cannot be CI-120H, CH2OCOCH3, or CH2CO2H;

(6) when R1 is

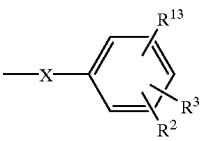

X is —OCH2—, and R13 is 2-CO2H, and R7 is H then R6 is not C2H5S;

(7) when R1 is

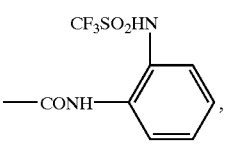

and R6 is n-hexyl then R7 and R8 are not both hydrogen;

(8) when R1 is

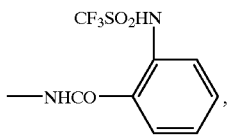

R6 is not methoxybenzyl;

(9) the R6 group is not

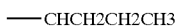

or CI-120H;

(10) when r=0, R1 is

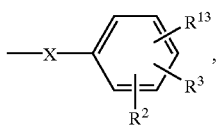

(11) when r=0, R1 is:

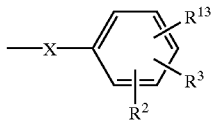

X is

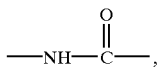

R13 is 2-NHSO$_2$CF$_3$, and R6 is n-propyl, then R$^7$ and R$^8$ are not —CO$_2$CH$_3$;

X is

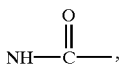

R$^{13}$ is 2-COOH, and R$^6$ is n-propyl, then R$^7$ and R$^8$ are not —CO$_2$CH$_3$;

(12) when r=1 is:

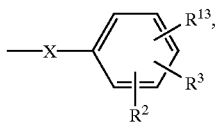

X is a single bond, R$^7$ is Cl, and R$^8$ is —CHO, then R$^{13}$ is not 3-(tetrazol-5-yl);

(13) when r=4, R$^1$ is:

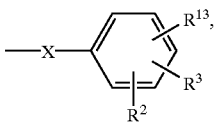

X is a single bond, R$^7$ is Cl, and R$^8$ is —CHO, then R$^{13}$ is not 4-(tetrazol-5-yl).

12. The method according to claim 11 wherien the patient is selected from renal transplant patients and heart transplant patients.

13. A method for treating and preventing chronic rejection in renal transplant patients comprising administering to said patients a therapeutically effective amount of an angiotensin II receptor antagonist compound of formula I:

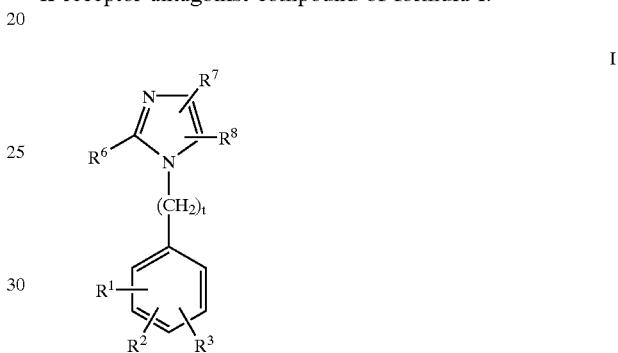

wherein:

R$^1$ is:

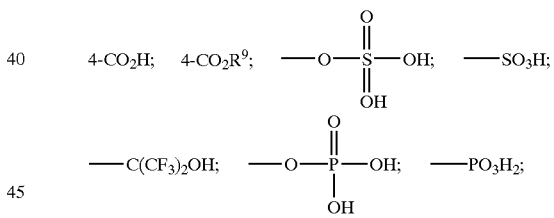

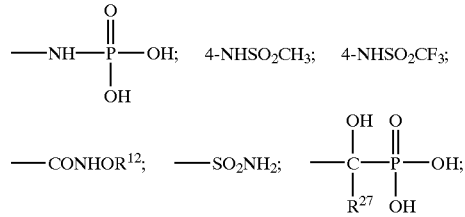

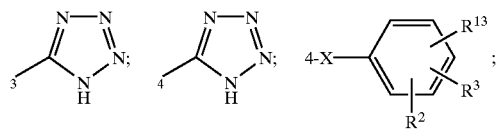

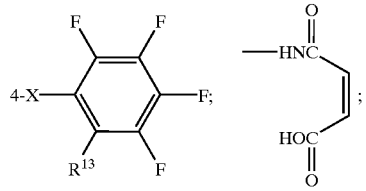

$R^2$ is H; Cl; Br; I; F; $NO_2$; CN; alkyl of 1 to 4 carbon atoms; acyloxy of 1 to 4 carbon atoms; alkoxy of 1 to 4 carbon atoms; $CO_2H$; $CO_2R^9$; $HNSO_2CH_3$; $NHSO_2CF_3$; $CONHOR^{12}$; $SO_2NH_2$;

aryl; or furyl;

$R^3$ is H; Cl, Br, I or F; alkyl of 1 to 4 carbon atoms or alkoxy of 1 to 4 carbon atoms;

$R^4$ is CN, $NO_2$ or $CO_2R^{11}$, $R^5$ is H, alkyl of 1 to 6 carbon atoms, cycloalkyl of 3 to 6 carbon atoms alkenyl or alkynyl of 2 to 4 carbon atoms;

$R^6$ is alkyl of 2 to 10 carbon atoms, alkenyl or alkynyl of 3 to 10 carbon atoms or the same groups substituted with F or $CO_2R^{14}$; cycloalkyl of 3 to 8 carbon atoms, cycloalkylalkyl, of 4 to 10 carbon atoms; cycloalkylalkenyl or cycloalkylalkynyl 5 to 10 carbon atoms; $(CH_2)_sZ(CH_2)MR^5$ optionally substituted with F or $CO_2R^{14}$; benzyl substituted on the phenyl ring with 1 or 2 halogens, alkoxy of 1 to 4 carbon atoms, alkyl of 1 to 4 carbon atoms or nitro;

R7 is H, F, Cl, Br, 1, $NO_2$, $C_vF_{2v}+1$, where v=1–6, $C_6F_5$; CN;

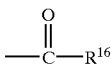

straight or branched alkyl of 1 to 6 carbon atoms; phenyl or phanylalkyl, where alkyl is 1 to 3 carbon atoms; or substituted phenyl or substituted phenylalkyl, where alkyl is 1 to 3 carbon atoms, substituted with one or two substituents selected from alkyl of 1 to 4 carbon atoms, F, Cl, Br, OH, $OCH_3$, $CF_3$, and COOR, where R is H, alkyl of 1 to 4 carbon atoms, or phenyl;

$R^8$ is H, CN, alkyl of 1 to 10 carbon atoms, alkenyl of 3 to 10 carbon atoms, or the same groups substituted with F; phenylalkenyl wherein the aliphatic portion is 2 to 6 carbon atoms; —$(CH_2)_m$-imidazol-1-yl; —$(CH_2)_m$-1,2,3-triazolyl optionally substituted with one or two group selected from $CO_2CH_3$ or alkyl of 1 to 4 carbon atoms; —$(CH_2)_s$ tetrazolyl;

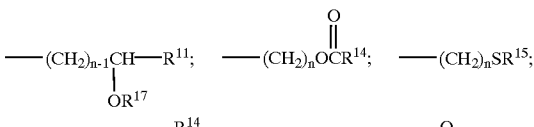
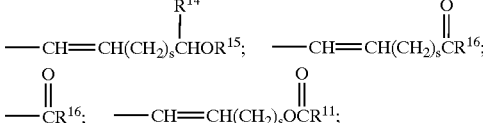
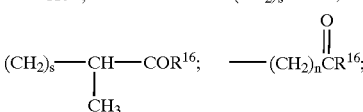
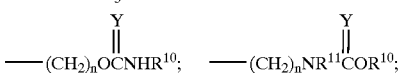
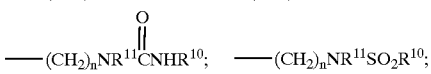
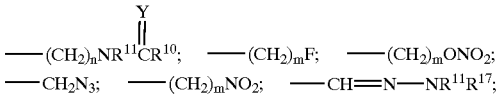
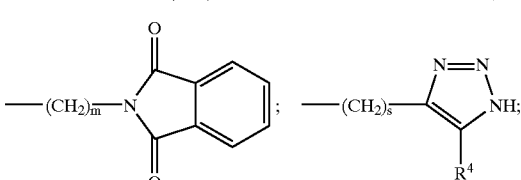
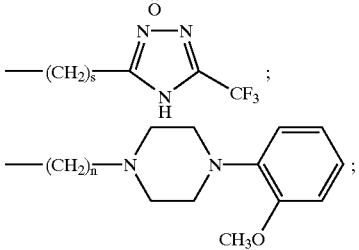
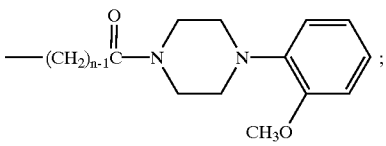

—CH=N—NH—SO$_2$—C$_6$H$_5$; or

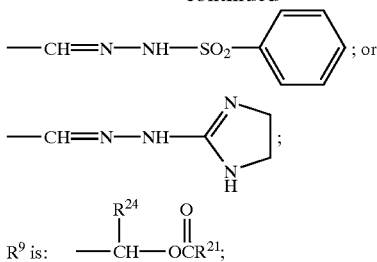

R$^9$ is: —CH(R$^{24}$)—OCR$^{21}$(=O);

R$^{10}$ is alkyl of 1 to 6 carbon atoms or perfluoroalkyl of 1 to 6 carbon atoms, 1-adaman 1-naphthyl, 1-(1-naphthyl)ethyl, or (CH$_2$)$_p$C$_6$H$_5$;
R$^{11}$ is H, alkyl of 1 to 6 carbon atoms, cycloalkyl of 3 to 6 carbon atoms, phenyl or benzyl;
R$^{12}$ is H, methyl or benzyl;

R13 is —CO$_2$H; —CO$_2$R$^9$; —CH$_2$CO$_2$H,

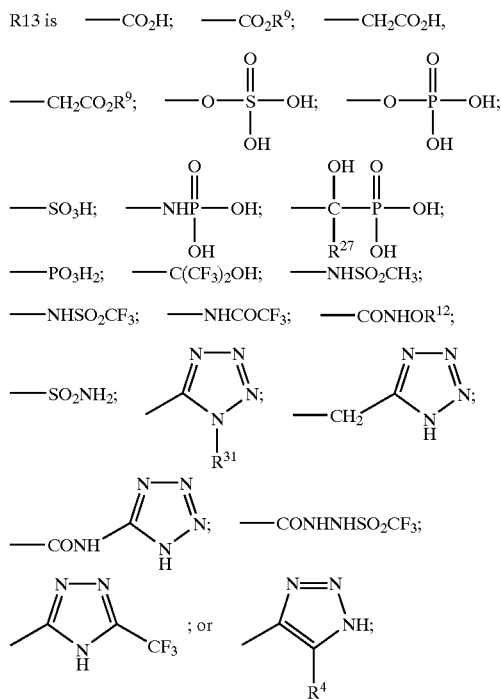

—NHSO$_2$CF$_3$; —NHCOCF$_3$; —CONHOR$^{12}$;
—SO$_2$NH$_2$; (tetrazole); (CH$_2$-tetrazole);
—CONH(tetrazole); —CONHNHSO$_2$CF$_3$;
(triazole-CF$_3$); or (triazole-R$^4$);

R$^{14}$ is H, alkyl or perfluoroalkyl of 1 to 8 carbon atoms, cycloalkyl of 3 to 6 carbon atoms, phenyl or benzyl;
R$^{15}$ is H, alkyl of 1 to 6 carbon atoms, cycloalkyl of 3 to 6 carbon atoms, phenyl, benzyl, acyl of 1 to 4 carbon atoms, phenacyl;
R$^{16}$ is H, alkyl of 1 to 6 carbon atoms, cycloalkyl of 3 to 6 carbon atoms, (CH$_2$)$_p$C$_6$H$_5$, OR$^{17}$, or NR$_{18}$R$^{19}$;
R$^{17}$ is H, alkyl of 1 to 6 carbon atoms, cycloalkyl of 3 to 6 carbon atoms, phenyl or benzyl;
R$^{18}$ and R$^{19}$ independently are H, alkyl of 1 to 4 carbon atoms, phenyl, benzyl, —→-methylbenzyl, or taken together with the nitrogen form a ring, of the formula

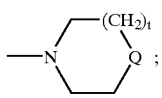

Q is NR20, O or CH2;
R20 is H, alkyl of 1–4 carbon atoms, or phenyl;
R21 is alkyl of 1 to 6 carbon atoms, —NR22R239 or —CHCH2CO2CH3; NH$_2$ R22 and R23 independently are H, alkyl of 1 to 6 carbon atoms, benzyl, or are taken together as (C1I2)u where u is 3–6;
R$^{24}$ is H, CH$_3$ or —C$_6$H$_5$;
R$^{25}$ is NR$^{27}$R$^{28}$, OR$^{28}$, NHCONH$_2$, NHCSNH$_2$,

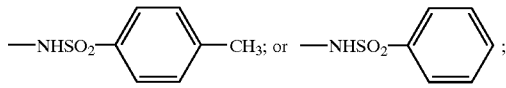

R26 is hydrogen, alkyl with from 1 to 6 carbon atoms, benzyl, or allyl;
R27 and R28 are independently hydrogen, alkyl with from 1 to 5 carbon atoms, or phenyl;
R29 and R30 are independently alkyl of 1–4 carbon atoms or taken together are —(CH2)q—;
R31 is H, alkyl or 1 to 4 carbon atoms, —CH2CH=CH2 or —CH2C6H4R32;
Y is O or S;
Z is O, NR11 or S;
m is 1 to 5;
n is 1 to 10;
p is 0 to 3;
q is 2 to 3;
r is 0 to 2;
s is 0 to 5;
t is 0 or 1;

and pharmaceutically acceptable salts of these compounds; provided that:

(1) the R1 group is not in the ortho position;
X is a carbon—carbon single bond, —CO—, —CH$_2$—, —O—, —S—,
—NH—, —N(R$^{26}$)—, —CON(R$^{23}$)—, —NCO(R$^{23}$)—,
—OCH$_2$—, —CH$_2$O—, —SCH$_2$—,
—CH$_2$S—, —NHC(R$^{27}$)(R$^{28}$)—, —NR$^{23}$SO$_2$—,
—SO$_2$NR$^{23}$—, —CH=CH—, —CF=CF—,
—CH=CF—, —CF=CH—,
—CH$_2$CH$_2$—, —C(R$^{27}$)(R$^{28}$)NH—, —CF$_2$CF$_2$—; 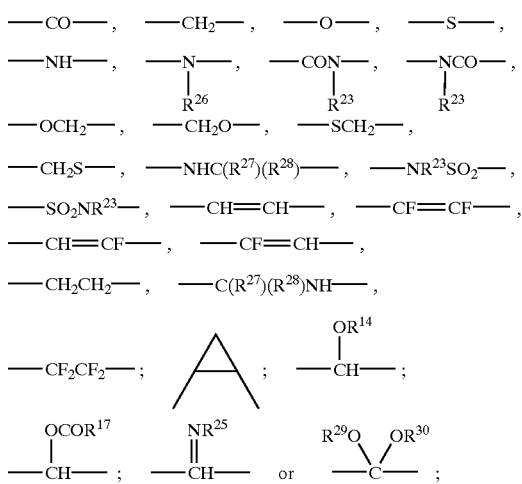

(2) when R1 is

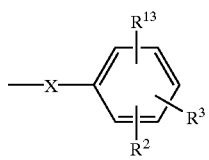

X is a single bond, and R13 is CO2H, or

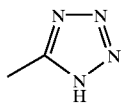

then R13 must be in the ortho or meta position; or when R1 and X are as above and R13 is NHSO2CF3 or NHSO2CH3, R13 must-be ortho, (3) when R1 is

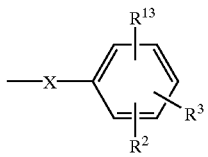

and X is other than a single bond, then R13 must be ortho except when X=NR23CO and R13 is NHSO2CF3 or NHSO2CH3 then R13 must be ortho, or meta;

(4) when R1 is 4-CO2H or a salt thereof, R6 cannot be S-alkyl;

(5) when R1 is 4-CO2H or a salt thereof, the substituent on the 4-position of the imidazole cannot be CI-120H, CH2OCOCH3, or CH2CO2H;

(6) when R1 is

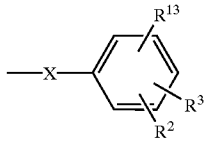

X is —OCH2—, and R13 is 2CO2H, and R7 is H then R6 is not C2H5S;

(7) when R1 is

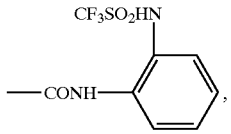

and R6 is n-hexyl then R7 and R8 are not both hydrogen;

(8) when R1 is

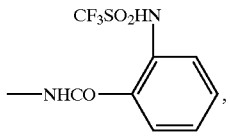

R6 is not methoxybenzyl;

(9) the R6 group is not

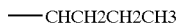

or CI-120H;

(10) when r=0, R1 is

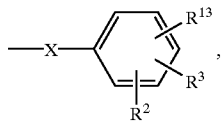

(11) when r=0, R1 is:

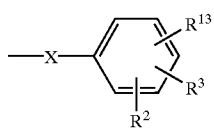

X is

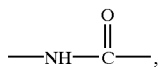

$R^{13}$ is 2-NHSO$_2$CF$_3$, and $R^6$ is n-propyl, then $R^7$ aid $R^8$ are not —CO2CH$_3$;

X is

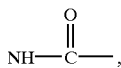

$R^{13}$ is 2-COOH and $R^6$ is n-propyl, then $R^7$ and $R^8$ are not —CO$_2$CH$_3$;

(12) when r=1 is:

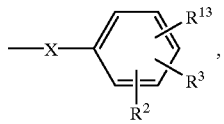

X is a single bond, $R^7$ is Cl, and $R^8$ is —CHO, then $R^{13}$ is not 3-(tetrazol-5-yl);

(13) when r=4, $R^1$ is:

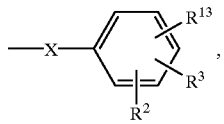

X is a single bond, $R^7$ is Cl, and $R^8$ is —CHO, then $R^{13}$ is not 4-(tetrazol-5-yl).

14. A method for reducing proteinuria in renal transplant patients comprising administering to said patients a therapeutically effective amount of an angiotensin II receptor antagonist compound of formula I:

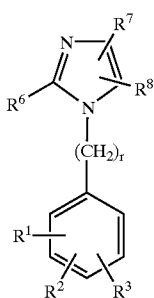

wherein:

R¹ is:

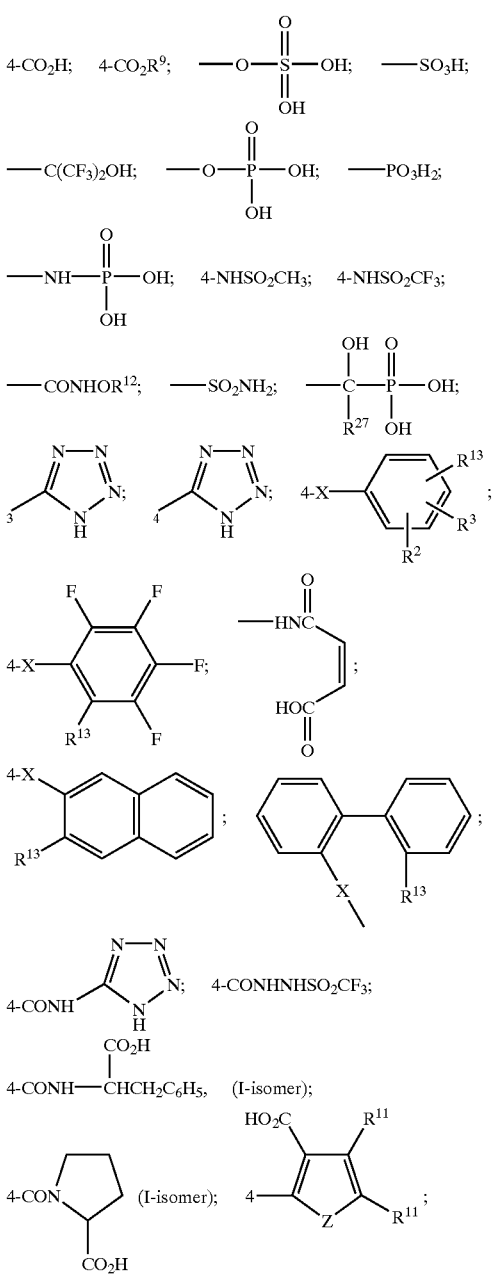

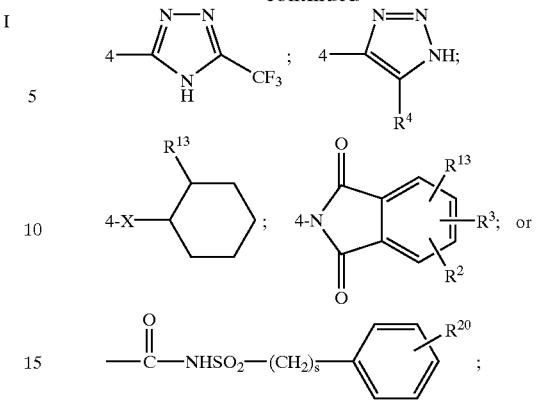

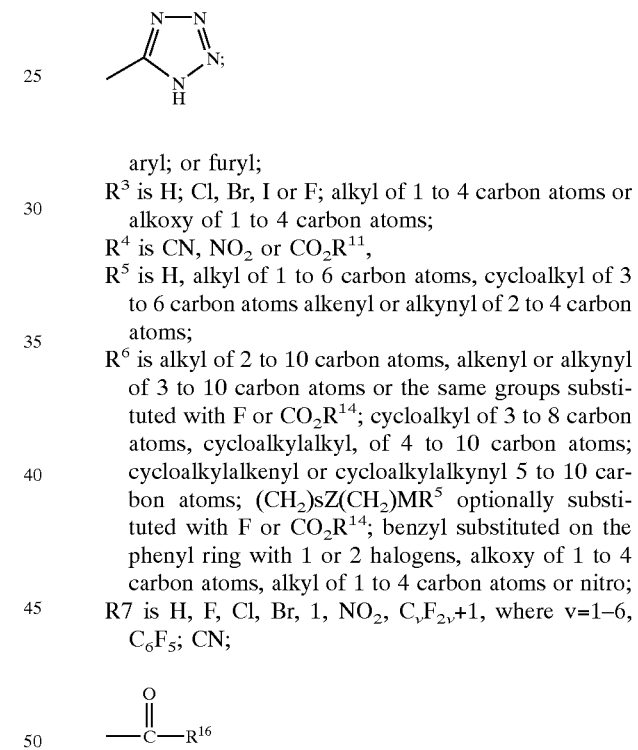

$R^2$ is H; Cl; Br, I; F; $NO_2$; CN; alkyl of 1 to 4 carbon atoms; acyloxy of 1 to 4 carbon atoms; alkoxy of 1 to 4 carbon atoms; $CO_2H$; $CONHOR^{12}$; $SO_2NH_2$;

aryl; or furyl;

$R^3$ is H; Cl, Br, I or F; alkyl of 1 to 4 carbon atoms or alkoxy of 1 to 4 carbon atoms;

$R^4$ is CN, $NO_2$ or $CO_2R^{11}$, $R^5$ is H, alkyl of 1 to 6 carbon atoms, cycloalkyl of 3 to 6 carbon atoms alkenyl or alkynyl of 2 to 4 carbon atoms;

$R^6$ is alkyl of 2 to 10 carbon atoms, alkenyl or alkynyl of 3 to 10 carbon atoms or the same groups substituted with F or $CO_2R^{14}$; cycloalkyl of 3 to 8 carbon atoms, cycloalkylalkyl, of 4 to 10 carbon atoms; cycloalkylalkenyl or cycloalkylalkynyl 5 to 10 carbon atoms; $(CH_2)sZ(CH_2)MR^5$ optionally substituted with F or $CO_2R^{14}$; benzyl substituted on the phenyl ring with 1 or 2 halogens, alkoxy of 1 to 4 carbon atoms, alkyl of 1 to 4 carbon atoms or nitro;

R7 is H, F, Cl, Br, 1, $NO_2$, $C_vF_{2v}+1$, where v=1–6, $C_6F_5$; CN;

$$-\overset{O}{\underset{}{C}}-R^{16}$$

straight or branched alkyl of 1 to 6 carbon atoms; phenyl or phanylalkyl, where alkyl is 1 to 3 carbon atoms; or substituted phenyl or substituted phenylalkyl, where alkyl is 1 to 3 carbon atoms, substituted with one or two substituents selected from alkyl of 1 to 4 carbon atoms, F, Cl, Br, OH, $OCH_3$, $CF_3$, and COOR, where R is H, alkyl of 1 to 4 carbon atoms, or phenyl;

$R^8$ is H, CN, alkyl of 1 to 10 carbon atoms, alkenyl of 3 to 10 carbon atoms, or the same groups substituted with F; phenylalkenyl wherein the aliphatic portion is 2 to 6 carbon atoms; $-(CH_2)m$-imidazol-1-yl; $-(CH_2)_m$-1,2,3-triazolyl optionally substituted with one or two group selected from $CO_2CH_3$ or alkyl of 1 to 4 carbon atoms; $-(CH_2)_s$ tetrazolyl;

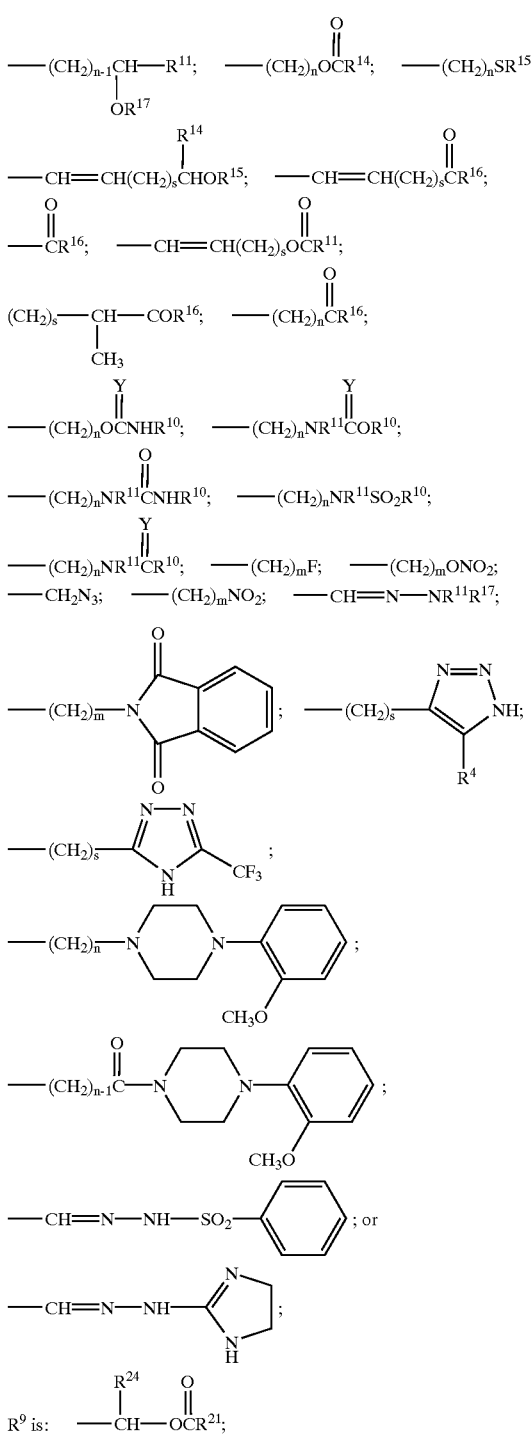

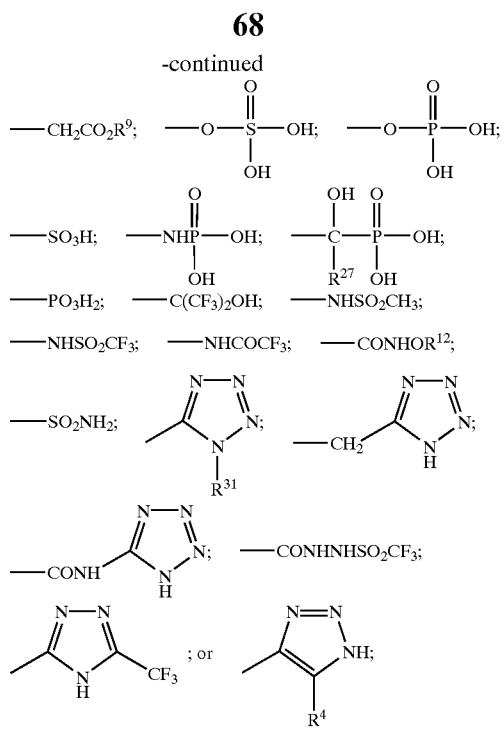

$R^{14}$ is H, alkyl or perfluoroalkyl of 1 to 8 carbon atoms, cycloalkyl of 3 to 6 carbon atoms, phenyl or benzyl;

$R^{15}$ is H, alkyl of 1 to 6 carbon atoms, cycloalkyl of 3 to 6 carbon atoms, phenyl, benzyl, acyl of I to 4 carbon atoms, phenacyl;

$R^{16}$ is H, alkyl of 1 to 6 carbon atoms, cycloalkyl of 3 to 6 carbon atoms, $(CH_2)_pC_6H_5$, $OR^{17}$, or $NR^{18}R^{19}$;

$R^{17}$ is H, alkyl of 1 to 6 carbon atoms, cycloalkyl of 3 to 6 carbon atoms, phenyl or benzyl;

$R^{18}$ and $R^{19}$ independently are H, alkyl of 1 to 4 carbon atoms, phenyl, benzyl, →-methylbenzyl, or taken together with the nitrogen form a ring, of the formula

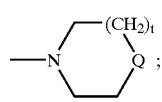

Q is NR20, O or CH2;

R20 is H, alkyl of 1–4 carbon atoms, or phenyl;

R21 is alkyl of 1 to 6 carbon atoms, —NR22R239 or —CHCH2CO2CH3; NH2

R22 and R23 independently are H, alkyl of 1 to 6 carbon atoms, benzyl, or are taken together as (C112)u where u is 3–6;

$R^{24}$ is H, O or —$C_6H_5$;

$R^{25}$ is $N^{27}R^{28}$, $OR^{28}$, $NHCONH_2$, $NHCSNH_2$,

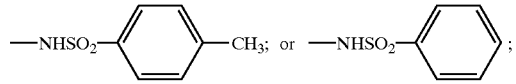

R26 is hydrogen, alkyl with from 1 to 6 carbon atoms, benzyl, or allyl;

R27 and R28 are independently hydrogen, alkyl with from 1 to 5 carbon atoms, or phenyl;

R29 and R30 are independently alkyl of 1–4 carbon atoms or taken together are —(CH2)q—;

R31 is H, alkyl or 1 to 4 carbon atoms, —CH2CH=CH2 or —CH2C6H4R32;

Y is O or S;
Z is O, NR11 or S;
m is 1 to 5;
n is 1 to 10;
p is 0 to 3;
q is 2 to 3;
r is 0 to 2;
s is 0 to 5;
t is 0 or 1;
and pharmaceutically acceptable salts of these compounds; provided that:

(1) the R1 group is not in the ortho position;
X is a carbon—carbon single bond,

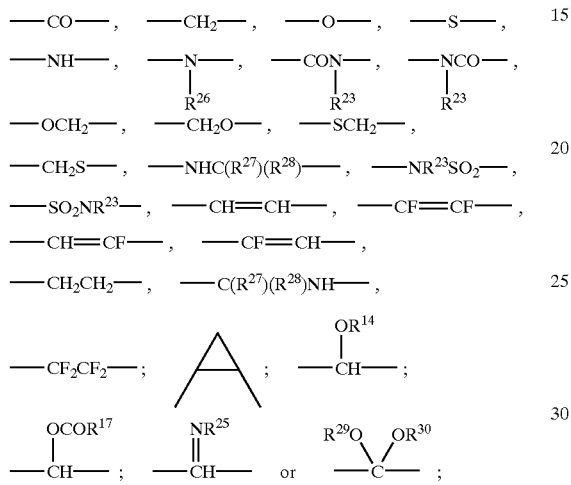

(2) when R1 is

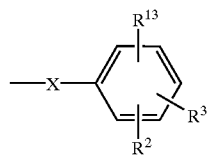

X is a single bond, and R13 is CO2H, or

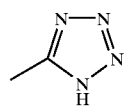

then R13 must be in the ortho or meta position; or when R1 and X are as above and R13 is NHSO2CF3 or NHSO2CH3, R13 must-be ortho, (3) when R1 is

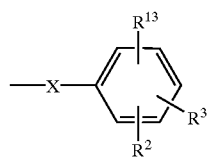

and X is other than a single bond, then R13 must be ortho except when X=NR23CO and R13 is NHSO2CF3 or NHSO2CH3 then R13 must be ortho, or meta;

(4) when R1 is 4-CO2H or a salt thereof, R6 cannot be S-alkyl;

(5) when R1 is 4-CO2H or a salt thereof, the substituent on the 4-position of the imidazole cannot be CI-120H, CH2OCOCH3, or CH2CO2H;

(6) when R1 is

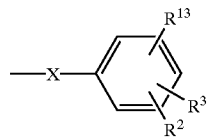

X is —OCH2—, and R13 is 2-CO2H, and R7 is H then R6 is not C2H5S;

(7) when R1 is

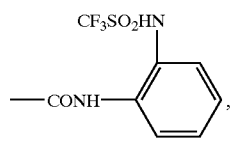

and R6 is n-hexyl then R7 and R8 are not both hydrogen;

(8) when R1 is

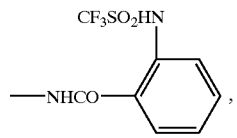

R6 is not methoxybenzyl;

(9) the R6 group is not

or CI-120H;

(10) when r=0, R1 is

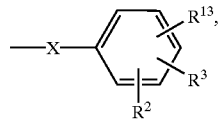

(11) when r=0, R1 is:

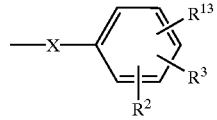

X is $$-NH-\overset{O}{\underset{\|}{C}}-,$$

$R^{13}$ is 2-NHSO$_2$CF$_3$, and R$^6$ is n-propyl, then R$^7$ a R$^8$ are not —CO$_2$CH$_3$;

X is $$NH-\overset{O}{\underset{\|}{C}}-,$$

$R^{13}$ is 2-COOR, and R$^6$ is n-propyl, then R$^7$ and R$^8$ are not —CO$_2$CH$_3$;

(12) when r=1 is:

$$-X-\langle\text{phenyl with } R^{13}, R^3, R^2\rangle$$

X is a single bond, R$^7$ is Cl, and R$^8$ is —CHO, then R$^{13}$ is not 3-(tetrazol-5-yl);

(13) when r=4, R$^1$ is:

$$-X-\langle\text{phenyl with } R^{13}, R^3, R^2\rangle$$

X is a single bond, R$^7$ is Cl, and R$^8$ is —CHO, then R$^{13}$ is not 4-(tetrazol-5-yl).

15. A method for increasing the survival rate of transplant patient comprising administering to said patients a therapeutically effective amount of an angiotensin II receptor antagonist compound selected from the group consisting of:

2-Butyl-4-chloro-1-[(2'-(1H-tetrazol-5-yl)biphenyl-4-yl) methyl]-5-(hydroxymethyl) imidazole;

2-Butyl-4-chloro-1-[(2'-carboxybiphenyl-4-yl)methyl]-5-(hydroxymethyl)imidazole;

2-Butyl-4-chloro-1-[(2'-carboxybiphenyl-4-yl)methyl]-5-(methoxycarbonyl)aminomethyl]imidazole;

2-Butyl-4-chloro-1-[(2'-carboxybiphenyl-4-yl)methyl]-5-[(propoxycarbonyl)aminomethy]imidazole;

2-Butyl-4-chloro-1-[(2'-carboxybiphenyl-4-yl)methyl] imidazole-5-carboxaldehyde;

2-Butyl-1-[(2'-carboxybiphenyl-4-yl)methyl]-imidazole-5-carboxy-aldehyde;

2-(1E-Butenyl)-4-chloro-1-[(2'-carboxybiphenyl-4-yl) methyl]-5-(hydroxymethyl)imidazole;

2-(1E-Butenyl)-4-chloro-1-[(2'-carboiybiphenyl-4-yl) methyl]-imidazole-6-carboxaldehyde;

2-Propyl-4-chloro-1-[(2'-(1H-tetrazol-5-yl)biphenyl-4-yl) methyl]-5-(hydroxymethyl)imidazole;

2-Propyl-4-chloro-1[(2'-(1H-tetrazol-5-yl)biphenyl-4-yl) methyl]-imidazole-5-carboxaldehyde;

2-Butyl-4-chloro-1-[2'-(1H-tetrazol-5-yl) biphenyl-4-yl) methyl]-imidazole-5-carboxaldehyde;

2-(1E-Butenyl)-4-chloro-1-[(2'-(1H-tetrazol-5-yl) bipheny 1-4-yl)methyl]-5-hydroxymethyl)imidazole;

2(1E-Butenyl)-4-chloro-1-[(2'-(1H-tetrazol-5-yl)biphenyl-4-yl)methyl]imidazole-5-carboxaldehyde;

2-Butyl-4-chloro-1-[(2'-(1H-tetrazol-5-yl)-biphenyl-4-yl) methyl]-imidazole-5-carboxylic acid;

2-Propyl-4-chloro-1-[(2'-(1H-totrazol-5-yl)-biphenyl-4-yl)methyl]-imidazole-5-carboxylic acid;

2-Propyl-4-trifluoromethyl-1-[(2-(1H-tetrazol-5-yl) biphenyl-4-yl)methyl]imidazole-5-carboxylic acid;

2-Propyl-4-trifluoromethyl-1-[(2'-(1H-1-tetrazol-5-yl) biphephenyl-4-yl)methyl]-5-(hydroxylmethyl) imidazole;

2-Butyl-4-trifluoromethyl-1-[(2'-(1H-tetrazol-5-yl) biphenyl-4-yl)methyl]imidazole-5-carboxylic acid;

2-Propyl-4-trifluoromethyl-1-[(2-(carboxybiphenyl-4-yl) methyl]-imidazole-5-carboxaldehyde;

2-Propyl-4-pentafluoroethyl-1-[(2'-(1H-tetrazol-5-yl) biphenyl-4-yl)methyl]-5-(hydroxymethyl) imidazole;

2-Propyl-1-[(2-(1H-tetrazol-5-yl)biphenyl-4-yl)methyl] imidazole-4,5,-dicarboxylic acid;

2-Propyl-4-pentafluoroethyl-1-[(2'-(1H-tetrazol-5-yl) biphenyl-4-ylmethyl]imidazole-5-carboxylic acid;

2-Propyl-4-pentafluoroethyl-[(2'-(1H-tetrazol-5-yl) biphenyl-4-yl)methyl]imidazole-5-carboxaldehyde; and or a pharmaceutically acceptable salt thereof.

16. The method according to claim 15 wherein the transplant patient is a renal transplant patient or a heart transplant patient.

17. The method according to claim 15 wherein the angiotensin II receptor antagonist compound is selected from the group consisting of 2-butyl-4-chloro-1-[(2'-tetrazol-5-yl) biphenyl-4-ylmethyl-[5-(hydroxy-methyl]imidazole; and 2-butyl-4-chloro-1-[(2'-tetrazol-5-yl) biphenyl-4-ylmethyl-[5-(hydroxy-methyl]imidazole-5-carboxylic acid and pharmaceutically acceptable salts thereof.

18. A method for treating and preventing chronic rejection in renal transplant patients comprising administering to said patients a therapeutically effective amount of an angiotensin II receptor antagonist compound selected from the group consisting of:

2-Butyl-4-chloro-1-[(2'-(1H-tetrazol-5-yl)biphenyl-4-yl) methyl]-5-(hydroxymethyl) imidazole;

2-Butyl-4-chloro-1-[(2'-carboxybiphenyl-4-yl)methyl]-5-(hydroxymethyl)imidazole;

2-Butyl-4-chloro-1-[(2-carboxybiphenyl-4-yl)methyl]5-(methoxycarbonyl)aminomethyl]imidazole;

2-Butyl-4-chloro-1-[(2'-carboxybiphenyl-4-yl)methyl]-5-[(propoxycarbonyl)aminomethyl]imidazole;

2-Butyl-4-chloro-1-[(2'-carboxybiphenyl-4-yl)methyl] imidazole-5-carboxaldehyde;

2-Butyl-1-[(2'-carboxybiphenyl-4-yl)methyl]-imidazole-5-carboxy-aldehyde;

2-(1E-Butenyl)-4-chloro-1-[(2'-carboxybiphenyl-4-yl) methyl]-5-(hydroxymethyl)imidazole;

2-(1E-Butenyl)-4-chloro-1-[(2'-carboiybiphenyl-4-yl) methyl]-imidazole-6-carboxaldehyde;

2-Propyl-4-chloro-1-[(2'-(1H-tetrazol-5-yl)biphenyl-4-yl) methyl]-5-(hydroxymethyl)imidazole;

2-Propyl-4-chloro-1[(2'-(1H-tetrazol-5-yl)biphenyl-4-yl) methyl]-imidazole-5-carboxaldehyde;

2-Butyl-4-chloro-1-[2'-(1H-tetrazol-5-yl) biphenyl-4-yl) methyl]-imidazole-5-carboxaldehyde;

2-(1E-Butenyl)-4-chloro-1-[(2'-(1H-tetrazol-5-yl) bipheny 1-4-yl)methyl]-5-hydroxymethyl) imidazole;

2(1E-Butenyl)-4-chloro-1-[(2'-(1H-tetrazol-5-yl)biphenyl-4-yl)methyl]imidazole-5-carboxaldehyde;

2-Butyl-4-chloro-1-[(2'-(1H-tetrazol-5-yl)-biphenyl-4-yl)methyl]-imidazole-5-carboxylic acid;

2-Propyl-4-chloro-1-[(2'-(1H-totrazol-5-yl)-biphenyl-4-yl)methyl]-imidazole-5-carboxylic acid;

2-Propyl-4-trifluoromethyl-1-[(2'-(1H-tetrazol-5-yl) biphenyl-4-yl)methyl]imidazole-5-carboxylic acid;

2-Propyl-4-trifluoromethyl-1-[(2'-(1H-1-tetrazol-5-yl) biphenyl-4-yl)methyl]-5-(hydroxylmethyl)imidazole;

2-Butyl-4-trifluoromethyl-1-[(2'-(1H-tetrazol-5-yl) biphenyl-4-yl)methyl]imidazole-5-carboxylic acid;

2-Propyl-4-trifluoromethyl-1-[(2'-(carboxybiphenyl-4-yl) methyl]-imidazole-5-carboxaldehyde;

2-Propyl-4-pentafluoroethyl-1-[(2'-(1H-tetrazol-5-yl) biphenyl-4-yl)methyl]-5-(hydroxymethyl)imidazole;

2-Propyl-1-[(2-(1H-tetrazol-5-yl)biphenyl-4-yl) methyl] imidazole-4,5,-dicarboxylic acid;

2-Propyl-4-pentafluoroethyl-1-[(2'-(1H-tetrazol-5-yl) biphenyl-4-yl)methyl]imidazole-5-carboxylic acid;

2-Propyl-4-pentafluoroethyl-[(2'-(1H-tetrazol-5-yl) biphenyl-4-yl)methyl]imidazole-5-carboxaldehyde; and or a pharmaceutically acceptable salt thereof.

19. The method according to claim 18 wherein the angiotensin II receptor antagonist compound is selected from the group consisting of 2-butyl-4-chloro-1-[(2'-tetrazol-5-yl)biphenyl-4-ylmethyl-[5-(hydroxy-methyl]imidazole; and 2-butyl-4-chloro-1-[(2'-tetrazol-5-yl)biphenyl-4-ylmethyl-[5-(hydroxy-methyl]imidazole-5-carboxylic acid and pharmaceutically acceptable salts thereof.

20. A method for reducing proteinuria in renal transplant patients comprising administering to said patients a therapeutically effective amount of an angiotensin II receptor antagonist compound selected from the group consisting of:

2-Butyl-4-chloro-1-[(2'-(1H-tetrazol-5-yl)biphenyl-4-yl)methyl]-5-(hydroxymethyl)imidazole;

2-Butyl-4-chloro-1-[(2'-carboxybiphenyl-4-yl)methyl]-5-(hydroxymethyl)imidazole;

2-Butyl-4-chloro-1-[(2'-carboxybiphenyl-4-yl)methyl]-5-[(methoxycarbonyl)aminomethyl]imidazole;

2-Butyl-4-chloro-1-[(2'-carboxybiphenyl-4-yl)methyl]-5-[lpropoxycarbonyl)aminomethyl]imidazole;

2-Butyl-4-chloro-1-[(2'-carboxybiphenyl-4-yl)methyl] imidazole-5-carboxaldehyde;

2-Butyl-[(2'-carboxybiphenyl-4-yl)methyl]-imidazole-5-carboxy-aldehyde;

2-(1E-Butenyl)-4-chloro-1-[(2'-carboxybiphenyl-4-yl) methyl]-5-(hydroxymethyl)imidazole;

2-(1E-Butenyl)-4-chloro-1-[(2'-carboiybiphenyl-4-yl) methyl]-imidazole-6-carboxaldehyde;

2-Propyl-4-chloro-1-[(2'-(1H-tetrazol-5-yl)biphenyl-4-yl) methyl]-5-(hydroxymethyl)imidazole;

2-Propyl-4-chloro-1[(2'-(1H-tetrazol-5-yl)biphenyl-4-yl) methyl]-imidazole-5-carboxaldehyde;

2-Butyl-4-chloro-1-[2-(1H-tetrazol-5-yl)biphenyl-4-yl) methyl3-imidazole-5-carboxaldehyde;

2-(1E-Butenyl)-4-chloro-1-[(2'-(1H-tetrazol-5-yl) bipheny 1-4-yl)methyl]-5-hydroxymethyl)imidazole;

2(1E-Butenyl)-4-chloro-1-[(2'-(1H-tetrazol-5-yl)biphenyl-4-yl)methyl]imidazole-5-carboxaldehyde;

2-Butyl-4-chloro-1-[(2'-(1H-tetrazol-S-yl)-biphenyl-4-yl) methyl]-imidazole-5-carboxylic acid;

2-Propyl-4-chloro-1-[(2'-(1H-totrazol-5-yl)-biphenyl-4-yl)methyl]-imidazole-5-carboxylic acid;

2-Propyl-4-trifluoromethyl-1-[(2'-(1H-tetrazol-5-yl) biphenyl-4-yl)methyl]imidazole-5-carboxylic acid;

2-Propyl-4-trifluoromethyl-1-[(2'-(1H-1-tetrazol-5-yl) biphenyl-4-yl)methyl]-5-(hydroxylmethyl)imidazole;

2-Butyl-4-trifluoromethyl-1-[(2'-(1H-tetrazol-5-yl) biphenyl-4-yl)methyl]imidazole-5-carboxylic acid;

2-Propyl-4-trifluoromethyl-1-[(2'-(carboxybiphenyl-4-yl) methyl]-imidazole-5-carboxaldehyde;

2-Propyl-4-pentafluoroethyl-1-[(2'-(1H-tetrazol-5-yl) biphenyl-4-yl)methyl]-5-(hydroxymethyl)imidazole;

2-Propyl-1-[(2-(1H-tetrazol-5-yl)biphenyl-4-yl) methyl] imidazole-4,5,-dicarboxylic acid;

2-Propyl-4-pentafluoroethyl-1-[(2'-(1H-tetrazol-5-yl) biphenyl-4-yl)methyl]imidazole-5-carboxylic acid;

2-Propyl-4-pentafluoroethyl-[(2-(1H-tetrazol-5-yl) biphenyl-4-yl)methyl]imidazole-5-carboxaldehyde; and or a pharmaceutically acceptable salt thereof.

21. The method according to claim 20 wherein the angiotensin II receptor antagonist compound is selected from the group consisting of 2-butyl-4-chloro-1-[(2'-tetrazol-5-yl) biphenyl-4-ylmethyl-[5-(hydroxy-methyl]imidazole; and 2-butyl-4-chloro-1-[(2'-tetrazol-5-yl) biphenyl-4-ylmethyl-[5-(hydroxy-methyl]imidazole-5-carboxylic acid and pharmaceutically acceptable salts thereof.

* * * * *

UNITED STATES PATENT AND TRADEMARK OFFICE
CERTIFICATE OF CORRECTION

PATENT NO.    : 6,576,652 B2
DATED         : June 10, 2003
INVENTOR(S)   : Giuseppe Remuzzi It is certified that error appears in the above-identified patent and that said Letters Patent is hereby corrected as shown below:

<u>Title page,</u>
Item [63], after "abandoned", insert -- which is the national stage under 35 U.S.C. §371 of international application PCT/IT98/00259, filed Sep. 30, 1998 --

Signed and Sealed this

Eighteenth Day of November, 2003

JAMES E. ROGAN
*Director of the United States Patent and Trademark Office*